US012697361B2

(12) United States Patent
Vile et al.

(10) Patent No.: US 12,697,361 B2
(45) Date of Patent: Aug. 4, 2026

(54) METHODS AND MATERIALS FOR TREATING CANCER

(71) Applicant: Mayo Foundation for Medical Education and Research, Rochester, MN (US)

(72) Inventors: Richard G. Vile, Rochester, MN (US); Laura Evgin, Vancouver (CA); Amanda L. Huff, Rochester, MN (US); Christopher B. Driscoll, Waltham, MA (US); Timothy J. Kottke, Oronoco, MN (US); Jason M. Tonne, Rochester, MN (US); Jill M. Thompson, Kasson, MN (US); Brady N. Zell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 456 days.

(21) Appl. No.: 18/027,768

(22) PCT Filed: Sep. 23, 2021

(86) PCT No.: PCT/US2021/051712
§ 371 (c)(1),
(2) Date: Mar. 22, 2023

(87) PCT Pub. No.: WO2022/066877
PCT Pub. Date: Mar. 31, 2022

(65) Prior Publication Data
US 2024/0009257 A1 Jan. 11, 2024

Related U.S. Application Data

(60) Provisional application No. 63/082,297, filed on Sep. 23, 2020.

(51) Int. Cl.
| | |
|---|---|
| *A61K 35/766* | (2015.01) |
| *A61K 38/08* | (2019.01) |
| *A61K 39/00* | (2006.01) |
| *A61P 35/00* | (2006.01) |
| *C07K 7/06* | (2006.01) |
| *C12N 7/00* | (2006.01) |
| *C12N 15/86* | (2006.01) |

(52) U.S. Cl.
CPC ............ *A61K 35/766* (2013.01); *A61K 38/08* (2013.01); *A61K 39/001192* (2018.08); *A61P 35/00* (2018.01); *C07K 7/06* (2013.01); *C12N 7/00* (2013.01); *C12N 15/86* (2013.01); *C12N 2760/20221* (2013.01); *C12N 2760/20232* (2013.01); *C12N 2760/20243* (2013.01)

(58) Field of Classification Search
None
See application file for complete search history.

(56) References Cited

U.S. PATENT DOCUMENTS

| | | |
|---|---|---|
| 2004/0033942 A1 | 2/2004 | Jackson et al. |
| 2012/0010142 A1 | 1/2012 | Burnett, Jr. et al. |
| 2012/0220047 A1 | 8/2012 | Seifried et al. |
| 2020/0206286 A1 | 7/2020 | Peng et al. |

FOREIGN PATENT DOCUMENTS

| | | | |
|---|---|---|---|
| CA | 2614311 A1 | 1/2007 | |
| WO | WO 2004/061413 A2 | 7/2004 | |
| WO | WO 2013/158263 A1 | 10/2013 | |
| WO | WO 2018/064460 A1 | 4/2018 | |
| WO | WO-2019191681 A1 * | 10/2019 | ......... A61K 39/3955 |
| WO | WO 2019/246528 A1 | 12/2019 | |
| WO | WO 2021/072284 A2 | 4/2021 | |

OTHER PUBLICATIONS

Kottke, Timothy; et al; "Oncolytic virotherapy induced CSDE1 neo-antigenesis restricts VSV replication but can be targeted by immunotherapy" Nature Communications, Dec. 2021 (Year: 2021).*
Guo, Ao-Xiang; et al; "The role of CSDE1 in translational reprogramming and human diseases" Cell Communication and Signaling, 18, 2020 (Year: 2020).*
Alonso-Camino et al., "The profile of tumor antigens which can be targeted by immunotherapy depends upon the tumor's anatomical site," Mol. Ther., Nov. 2014, 22(11):1936-1948.
Alvarez-Breckenridge et al., "Pharmacologic and Chemical Adjuvants in Tumor Virotherapy," Chem. Rev., Jul. 2009, 109(7):3125-3140.
Anderson et al., "Internal initiation of translation from the human rhinovirus-2 internal ribosome entry site requires the binding of Unr to two distinct sites on the 5' untranslated region," J. Gen. Virol., Nov. 2007, 88(Pt 11):3043-3052.
Boichard et al., "High expression of PD-1 ligands is associated with kataegis mutational signature and APOBEC3 alterations," Oncoimmunology, Jan. 2017, 6(3):e1284719.
Boisgerault et al., "Functional cloning of recurrence-specific antigens identifies molecular targets to treat tumor relapse," Mol. Ther., Aug. 2013, 21(8):1507-1516.

(Continued)

*Primary Examiner* — David W Berke-Schlessel
(74) *Attorney, Agent, or Firm* — Fish & Richardson P.C.

(57) ABSTRACT

This document provides methods and materials for treating cancer. For example, methods and materials for using oncolytic viruses (e.g., replication-competent vesicular stomatitis viruses) to treat cancer are provided. Replication-competent oncolytic viruses (e.g., replication-competent oncolytic vesicular stomatitis viruses), nucleic acid molecules encoding a replication-competent oncolytic virus (e.g., replication-competent oncolytic vesicular stomatitis virus), methods for making replication-competent oncolytic viruses (e.g., replication-competent oncolytic vesicular stomatitis viruses), methods for using replication-competent oncolytic viruses (e.g., replication-competent oncolytic vesicular stomatitis viruses) to treat cancer, cancer neoantigens, nucleic acids encoding a cancer neoantigen, and methods for stimulating immune cells (e.g., cytotoxic T lymphocytes) to kill cancer cells also are provided.

17 Claims, 47 Drawing Sheets

Specification includes a Sequence Listing.

(56) References Cited

OTHER PUBLICATIONS

Boussadia et al., "Unr is required in vivo for efficient initiation of translation from the internal ribosome entry sites of both rhinovirus and poliovirus," J. Virol., Mar. 2003, 77(6):3353-3359.

Bridle et al., "Vesicular stomatitis virus as a novel cancer vaccine vector to prime antitumor immunity amenable to rapid boosting with adenovirus," Mol. Ther., Oct. 2009, 17(10):1814-1821.

Burns et al., "APOBEC3B is an enzymatic source of mutation in breast cancer," Nature, Feb. 2013, 494(7437):366-370.

Carlson et al., "Establishment, maintenance and in vitro and in vivo applications of primary human glioblastoma multiforme (GBM) xenograft models for translational biology studies and drug discovery," Curr. Protoc. Pharmacol., Mar. 2011, Chapter 14(14):Unit 14.16.

Cescon et al., "APOBEC3B expression in breast cancer reflects cellular proliferation, while a deletion polymorphism is associated with immune activation," Proc. Natl. Acad. Sci. USA, Mar. 2015, 112(9):2841-2846.

Chen et al., "The preferred nucleotide contexts of the AID/APOBEC cytidine deaminases have differential effects when mutating retrotransposon and virus sequences compared to host genes," PLoS One, Mar. 2017, 13(3):e1005471.

Chou et al., "B-Myb Induces APOBEC3B Expression Leading to Somatic Mutation in Multiple Cancers," Sci. Rep., Mar. 7, 2017:44089.

ClinicalTrials.gov [online], "Modified Virus VSV-IFNbetaTYRP1 in Treating Patients With Stage III-IV Melanoma," NCT03865212, last updated Jan. 9, 2024, retrieved from URL<https://www.clinicaltrials.gov/study/NCT03865212>, 14 pages.

ClinicalTrials.gov [online], "Ph I/II Trial of Systemic VSV-IFNβ-NIS in Combination With Checkpoint Inhibitor Therapy in Patients With Select Solid Tumors," NCT03647163, last updated Apr. 2, 2025, retrieved from URL<https://www.clinicaltrials.gov/study/NCT03647163>, 18 pages.

ClinicalTrials.gov [online], "Viral Therapy in Treating Patient With Refractory Liver Cancer or Advanced Solid Tumors," NCT01628640, last updated Jan. 27, 2025, retrieved from URLhttps://www.clinicaltrials.gov/study/NCT01628640>, 13 pages.

Conticello et al., "Evolution of the AID/APOBEC family of polynucleotide (deoxy)cytidine deaminases," Mol. Biol. Evol., Feb. 2005, 22(2):367-377.

Diaz et al., "Oncolytic immunovirotherapy for melanoma using vesicular stomatitis virus," Cancer Res., Mar. 2007, 67(6):2840-2848.

Driscoll et al., "APOBEC3B-mediated corruption of the tumor cell immunopeptidome induces heteroclitic neoepitopes for cancer immunotherapy," Nat. Commun., Feb. 2020, 11(1):790.

Durham et al., "Oncolytic VSV Primes Differential Responses to Immuno-oncology Therapy," Mol. Ther., Aug. 2017, 25(8):1917-1932.

Errington et al., "Fusogenic membrane glycoprotein-mediated tumour cell fusion activates human dendritic cells for enhanced IL-12 production and T-cell priming," Gene Ther., Jan. 2006, 13(2):138-149.

Evgin et al., "Suboptimal T-cell therapy drives a tumor cell mutator phenotype that promotes escape from first-line treatment," Cancer Immunol. Res., May 2019, 7(5):828-840.

Extended European Search Report in European Appln. No. 21873411.9, mailed on Jul. 2, 2025, 17 pages.

Galivo et al., "Interference of CD40L-mediated tumor immunotherapy by oncolytic vesicular stomatitis virus," Hum. Gene Ther., Apr. 2010, 21(4):439-450.

Galivo et al., "Single-cycle viral gene expression, rather than progressive replication and oncolysis, is required for VSV therapy of B16 melanoma," Gene Ther., Feb. 2010, 17(2):158-170.

Gatenby et al., "The Evolution and Ecology of Resistance in Cancer Therapy," Cold Spring Harb. Perspect. Med., Mar. 2018, 8(3):a033415 [retracted article].

GenBank Accession No. AF235001.1, "Mus musculus sodium iodide symporter NIS mRNA, complete cds," Feb. 1, 2001, 2 pages.

GenBank Accession No. AF380353.1, "Mus musculus sodium iodide symporter mRNA, complete cds," Jun. 5, 2001, 2 pages.

GenBank Accession No. BC105047.1, "*Homo sapiens* solute carrier family 5 (sodium iodide symporter), member 5, mRNA (cDNA clone MGC:132707 Image:8144050), complete cds," Jul. 21, 2006, 3 pages.

GenBank Accession No. BC105049.1, "*Homo sapiens* solute carrier family 5 (sodium iodide symporter), member 5, mRNA (cDNA clone MGC:132709 Image:8144052), complete cds," Jul. 21, 2006, 3 pages.

GenBank Accession No. BC119395.1, "Mus musculus interferon beta 1, fibroblast, mRNA (cDNA clone MGC:155711 Image:8734144), complete cds," Aug. 9, 2006, 2 pages.

GenBank Accession No. BC119397.1, "Mus musculus interferon beta 1, fibroblast, mRNA (cDNA clone MGC:155713 Image:8734146), complete cds," Aug. 9, 2006, 2 pages.

GenBank Accession No. NC_001560.1, "Vesicular stomatitis Indiana virus, complete genome," Aug. 13, 2018, 8 pages.

GenBank Accession No. NM_000453.2, "*Homo sapiens* solute carrier family 5 member 5 (SLC5A5), mRNA," Nov. 10, 2018, 6 pages.

GenBank Accession No. NM_002176.2, "*Homo sapiens* interferon, beta 1, fibroblast (IFNB1), mRNA," May 11, 2014, 3 pages.

GenBank Accession No. NM_007158.6, "*Homo sapiens* cold shock domain containing E1 (CSDE1), transcript variant 2, mRNA," Aug. 27, 2019, 5 pages.

GenBank Accession No. NM_010510.1, "Mus musculus interferon beta 1, fibroblast (Ifnb1), mRNA," Aug. 21, 2019, 3 pages.

GenBank Accession No. NM_019127.1, "Rattus norvegicus interferon beta 1 (Ifnb1), mRNA," Apr. 19, 2019, 3 pages.

GenBank Accession No. NM_052983.2, "Rattus norvegicus solute carrier family 5 member 5 (Slc5a5), mRNA," Aug. 6, 2019, 6 pages.

GenBank Accession No. NM_053248.2, "Mus musculus solute carrier family 5 (sodium iodide symporter), member 5 (Slc5a5), mRNA," Feb. 18, 2019, 6 pages.

GenBank Accession No. NM_214410.1, "Sus scrofa solute carrier family 5 member 5 (SLC5A5), mRNA," May 20, 2017, 3 pages.

GenBank Accession No. XM_524154.4, "Predicted: Pan troglodytes solute carrier family 5 (sodium/iodide cotransporter), member 5 (SLC5A5), transcript variant X1, mRNA," Mar. 20, 2018, 3 pages.

GenBank Accession No. XM_541946.6, "Predicted: Canis lupus familiaris solute carrier family 5 member 5 (SLC5A5), transcript variant X1, mRNA," Sep. 5, 2017, 2 pages.

GenBank Accession No. XM_581578.8, "Predicted: Bos taurus solute carrier family 5 (sodium/iodide cotransporter), member 5 (SLC5A5), transcript variant X1, mRNA," Dec. 30, 2014, 2 pages.

Goel et al., "Radioiodide imaging and radiovirotherapy of multiple myeloma using VSV(Delta51)-NIS, an attenuated vesicular stomatitis virus encoding the sodium iodide symporter gene," Blood, Oct. 2007, 110(7):2342-2350.

Harris et al., "Retroviral restriction by APOBEC proteins," Nat. Rev. Immunol., Nov. 2004, 4(11):868-877.

Henderson et al., "APOBEC-mediated cytosine deamination links PIK3CA helical domain mutations to human papillomavirus-driven tumor development," Cell Rep., Jun. 2014, 7(6):1833-1841.

Hogquist et al., "T cell receptor antagonist peptides induce positive selection," Cell, Jan. 1994, 76(1):17-27.

Hu et al., "Epstein-Barr Virus Infection of Mammary Epithelial Cells Promotes Malignant Transformation," EBioMedicine, Jul. 9, 2016:148-160.

Huff et al., "APOBEC3 Mediates Resistance to Oncolytic Viral Therapy," Mol. Ther. Oncolytics, Aug. 11, 2018:1-13.

Ilett et al., "Prime-boost using separate oncolytic viruses in combination with checkpoint blockade improves anti-tumour therapy," Gene Ther., Jan. 2017, 24(1):21-30.

International Preliminary Report on Patentability in International Appln. No. PCT/US2021/051712, mailed on Apr. 6, 2023, 14 pages.

International Search Report and Written Opinion in International Appln. No. PCT/US2021/051712, mailed on Feb. 7, 2022, 19 pages.

Janelle et al., "The strength of the T cell response against a surrogate tumor antigen induced by oncolytic VSV therapy does not correlate with tumor control," Mol. Ther., Jun. 2014, 22(6):1198-1210.

(56) References Cited

OTHER PUBLICATIONS

Jenks et al., "Safety studies on intrahepatic or intratumoral injection of oncolytic vesicular stomatitis virus expressing interferon-beta in rodents and nonhuman primates," Hum. Gene Ther., Apr. 2010, 21(4):451-462.

Ju Lee et al., "A post-transcriptional program coordinated by CSDE1 prevents intrinsic neural differentiation of human embryonic stem cells," Nat. Commun., Nov. 2017, 8(1):1456.

Kaluza et al., "Adoptive T cell therapy promotes the emergence of genomically altered tumor escape variants," Int. J. Cancer, Aug. 2012, 131(4):844-854.

Kaluza et al., "Adoptive Transfer of Cytotoxic T Lymphocytes Targeting Two Different Antigens Limits Antigen Loss and Tumor Escape," Hum. Gene Ther., Jun. 2012, 23(10):1054-1064.

Kelly et al., "Attenuation of vesicular stomatitis virus encephalitis through microRNA targeting," J. Virol., Feb. 2010, 84(3):1550-1562.

Kottke et al. "Subversion of NK-cell and TNFα Immune Surveillance Drives Tumor Recurrence," Cancer Immunol. Res., Oct. 2017, 5(11):1029-1045.

Kottke et al., "Broad Antigenic Coverage Induced by Viral cDNA Library-based Vaccination Cures Established Tumors," Nat. Med., Jun. 2011, 17(7):854-859.

Kottke et al., "Detecting and targeting tumor relapse by its resistance to innate effectors at early recurrence," Nat. Med., Dec. 2013, 19(12):1625-1631.

Kottke et al., "Subversion of NK-cell and TNFα Immune Surveillance Drives Tumor Recurrence," Cancer Immunol. Res., Nov. 2017, 5(11):1029-1045.

Kottke et al., "Vaccination against a neoepitope whose expression is driven by acquired resistance to oncolytic virotherapy prevents VSV-resistant tumour recurrence," Presented at Proceedings of the 5th CRI-CIMT-EATI-AACR International Cancer Immunotherapy Conference, Translating Science into Survival, Sep. 25-28, 2019, 30 pages.

Law et al., "The DNA cytosine deaminase APOBEC3B promotes tamoxifen resistance in ER-positive breast cancer," Sci/ Adv., Oct. 2016, 2(10):e1601737.

Leonard et al., "APOBEC3G Expression Correlates with T-Cell Infiltration and Improved Clinical Outcomes in High-grade Serous Ovarian Carcinoma," Clin. Cancer Res., Sep. 2016, 22(18):4746-4755.

Leonard et al., "The PKC/NF-κB Signaling Pathway Induces APOBEC3B Expression in Multiple Human Cancers," Cancer Res., Nov. 2015, 75(21):4538-4547.

MacMillan et al., "APOBEC3 inhibition of mouse mammary tumor virus infection: the role of cytidine deamination versus inhibition of reverse transcription," J. Virol., May 2013, 87(9):4808-4817.

Martinez-Useros et al., "UNR/ CSDE1 Expression Is Critical to Maintain Invasive Phenotype of Colorectal Cancer through Regulation of c-MYC and Epithelial-to-Mesenchymal Transition," J. Clin. Med., Apr. 2019, 8(4):560.

Maruyama et al., "Classical NF-κB pathway is responsible for APOBEC3B expression in cancer cells," Biochem. Biophys. Res. Commun., Sep. 2016, 478(3):1466-1471.

Mcgranahan et al., "Allele-Specific HLA Loss and Immune Escape in Lung Cancer Evolution," Cell, Nov. 2017, 171(6):1259-1271. e11.

McGranahan et al., "Biological and therapeutic impact of intratumor heterogeneity in cancer evolution," Cancer Cell, Jan. 2015, 27(1):15-26.

Mehta et al., "IFN-α and Lipopolysaccharide Upregulate APOBEC3 mRNA through Different Signaling Pathways," J. Immunol., Oct. 2012, 189(8):4088-4103.

Merrick et al., "Immunosuppressive effects of radiation on human dendritic cells: reduced IL-12 production on activation and impairment of naive T-cell priming," Br. J. Cancer, Apr. 2005, 92(8):1450-1458.

Mertz et al., "Risks at the DNA Replication Fork: Effects upon Carcinogenesis and Tumor Heterogeneity," Genes, Jan. 2017, 8(1):46.

Mihailovich et al., "Eukaryotic cold shock domain proteins: highly versatile regulators of gene expression," Bioessays, Feb. 2010, 32(2):109-118.

Muto et al., "Identification and analysis of host proteins that interact with the 3'-untranslated region of tick-borne encephalitis virus genomic RNA," Virus Res., Apr. 2018, 249:52-56.

Nair et al., "Biochemical and biological studies of mouse APOBEC3," J. Virol., Apr. 2014, 88(7):3850-3860.

Obuchi et al., "Development of recombinant vesicular stomatitis viruses that exploit defects in host defense to augment specific oncolytic activity," J. Virol., Aug. 2003, 77(16):8843-8856.

Overwijk et al., "gp100/pmel 17 is a murine tumor rejection antigen: induction of "self"-reactive, tumoricidal T cells using high-affinity, altered peptide ligand," J. Exp. Med., Jul. 1998, 188(2):277-286.

Partial Supplementary European Search Report in European Appln. No. 21873411.9, mailed on Apr. 7, 2025, 17 pages.

Pulido et al., "Using virally expressed melanoma cDNA libraries to identify tumor-associated antigens that cure melanoma," Nat. Biotechnol., Mar. 2012, 30(4):337-343.

Rambow et al., "Identification of differentially expressed genes in spontaneously regressing melanoma using the MeLiM swine model," Pigment Cell Melanoma Res., Apr. 2008, 21(2):147-161.

Roberts et al., "An APOBEC cytidine deaminase mutagenesis pattern is widespread in human cancers," Nat. Genet., Sep. 2013, 45(9):970-976.

Saibil et al., "Targeting T cell activation in immuno-oncology," Curr. Oncol., Apr. 2020, 27(Suppl 2):S98-S105.

Sanchez-Perez et al., "Synergy of adoptive T-cell therapy with intratumoral suicide gene therapy is mediated by host NK cells," Gene Ther., Jul. 2007, 14(13):998-1009.

Schmid et al., "Evidence for a TCR Affinity Threshold Delimiting Maximal CD8 T Cell Function," J. Immunol., May 2010, 184(9):4936-4946.

Schnell et al., "Foreign glycoproteins expressed from recombinant vesicular stomatitis viruses are incorporated efficiently into virus particles," Proc. Natl. Acad. Sci. USA, Oct. 1996, 93(21):11359-11365.

Schumacher et al., "Cancer Neoantigens," Annu. Rev. Immunol., Apr. 2019, 37:173-200.

Schumacher et al., "Neoantigens in cancer immunotherapy," Science, Apr. 2015, 348(6230):69-74.

Shi et al., "Combining Oncolytic Viruses With Cancer Immunotherapy: Establishing a New Generation of Cancer Treatment," Front. Immunol., Apr. 11, 2020:683.

Shi et al., "Structural basis for targeted DNA cytosine deamination and mutagenesis by APOBEC3A and APOBEC3B," Nat. Struct. Mol. Biol., Feb. 2017, 24(2):131-139.

Shim et al., "Inhibitory Receptors Induced by VSV Viroimmunotherapy Are Not Necessarily Targets for Improving Treatment Efficacy," Mol. Ther., Apr. 2017, 25(4):962-975.

Slansky et al., "Peptide mimotopes alter T cell function in cancer and autoimmunity," Semin. Immunol., Feb. 2020, 47:101395.

Smid et al., "Breast cancer genome and transcriptome integration implicates specific mutational signatures with immune cell infiltration," Nat. Commun., Sep. 7, 2016:12910.

Stankova et al., "Optimizing Cancer Treatment Using Game Theory: A Review," JAMA Oncol., Jan. 2019, 5(1):96-103.

Stojdl et al., "Exploiting tumor-specific defects in the interferon pathway with a previously unknown oncolytic virus," Nat. Med., Jul. 2000, 6(7):821-825.

Stojdl et al., "VSV strains with defects in their ability to shutdown innate immunity are potent systemic anti-cancer agents," Cancer Cell, Oct. 2003, 4(4):263-275.

Swanton et al., "APOBEC Enzymes: Mutagenic Fuel for Cancer Evolution and Heterogeneity," Cancer Discov., Jul. 2015, 5(7):704-712.

Takeda et al., "IFN-γ is required for cytotoxic T cell-dependent cancer genome immunoediting," Nat. Commun., Feb. 8, 2017:14607.

Triqueneaux et al., "RNA binding specificity of Unr, a protein with five cold shock domains," Nucleic Acids Res., Apr. 1999, 27(8):1926-1934.

(56) References Cited

OTHER PUBLICATIONS

Venkatesan et al., "Perspective: APOBEC mutagenesis in drug resistance and immune escape in HIV and cancer evolution," Ann. Oncol., Mar. 2018, 29(3):563-572.

Vile et al., "A100 / Vaccination against a neoepitope whose expression is driven by acquired resistance to oncolytic virotherapy prevents VSV-resistant tumour recurrence," Abstract, Presented at Proceedings of the 5th CRI-CIMT-EATI-AACR International Cancer Immunotherapy Conference, Translating Science into Survival, Sep. 25-28, 2019, Abstracts Book, pp. 41-42.

Vile et al., "Generation of an anti-tumour immune response in a non-immunogenic tumour: HSVtk-killing in vivo stimulates a mononuclear cell infiltrate and a Th1-like profile of intratumoural cytokine expression," Int. J. Cancer, Apr. 1997, 71(2):267-274.

Vile et al., "Systemic Gene Therapy of Murine Melanoma Using Tissue Specific Expression of the HSVtk Gene Involves an Immune Component," Cancer Res., Dec. 1994, 54(23):6228-6234.

Walker et al., "APOBEC family mutational signatures are associated with poor prognosis translocations in multiple myeloma," Nat. Commun., Apr. 6, 2015:6997.

Wei et al., "Fundamental Mechanisms of Immune Checkpoint Blockade Therapy," Cancer Discov., Sep. 2018, 8(9):1069-1086.

Willmon et al., "Expression of IFN-β Enhances Both Efficacy and Safety of Oncolytic Vesicular Stomatitis Virus for Therapy of Mesothelioma," Cancer Res., Oct. 2009, 69(19):7713-7720.

Willmon et al., "Vesicular stomatitis virus-induced immune suppressor cells generate antagonism between intratumoral oncolytic virus and cyclophosphamide," Mol. Ther., Jan. 2011, 19(1):140-149.

Wolchok et al., "Safety and immunogenicity of tyrosinase DNA vaccines in patients with melanoma," Mol. Ther., Nov. 2007, 15(11):2044-2050.

Wongthida et al., "Activating systemic T-cell immunity against self tumor antigens to support oncolytic virotherapy with vesicular stomatitis virus," Hum. Gene Ther., Nov. 2011, 22(11):1343-1353.

Wongthida et al., "Type III IFN Interleukin-28 Mediates the Antitumor Efficacy of Oncolytic Virus VSV in Immune-Competent Mouse Models of Cancer," Cancer Res., Jun. 2010, 70(11):4539-4549.

Wongthida et al., "VSV oncolytic virotherapy in the B16 model depends upon intact MyD88 signaling," Mol. Ther., Jan. 2011, 19(1):150-158.

Wurth et al., "UNR/CSDE1 Drives a Post-transcriptional Program to Promote Melanoma Invasion and Metastasis," Cancer Cell, Nov. 2016, 30(5):694-707.

Yarchoan et al., "Targeting neoantigens to augment antitumour immunity," Nat. Rev. Cancer, Apr. 2017, 17(4):209-222.

Zaidi et al., "Mutated BRAF Emerges as a Major Effector of Recurrence in a Murine Melanoma Model After Treatment With Immunomodulatory Agents," Mol. Ther., May 2015, 23(5):845-856.

* cited by examiner

B16 Parental
Exclusively GATCC (WT)

T T T G A T C C

B16 -VSV-GFP ESC
Predominantly GATTC (MUT)
Minority GATCC (WT)

T T T G A T T C

B16TK-GCV 21d ESC
Exclusively GATCC (WT)

T T T G A T C C

B16 -VSV-mIFNβ ESC ESC
Exclusively GATTC (MUT)

T T T G A T T C

B16 -shRNA mAPOBEC3-
VSV-GFP ESC
Exclusively GATCC (WY)

T T T G A T C C

B16-shRNA mAPOBEC3-
VSV-mIFNβ ESC
Exclusively GATCC (WT)

T T T G A T C C

Hep3B Parental
Exlusively GATCC (WT)

T T T G A T C C

Hep3B-VSV-GFP ESC
Predominantly GATCC (WT)
Minority GATTC (MUT)

T T T G A T C C

Hep3B-VSV-hIFNβ ESC
Exclusively GATTC (MUT)

T T T G A T T C

Experiment 1
Hep3B VSV-hIFNβ-
CSDE1$^{WT}$ ESC
Experiment 2
Hep3B VSV-hIFNβ-
CSDE1$^{WT}$ ESC
T T T G A T T C
T T T G A T C C
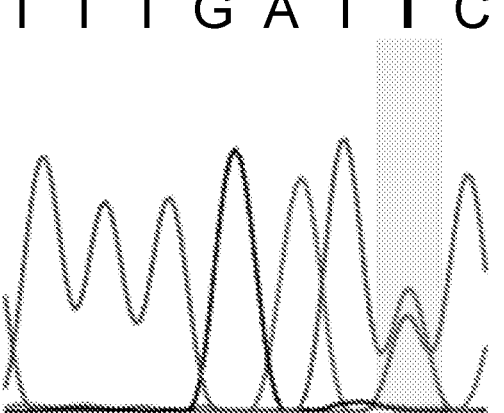
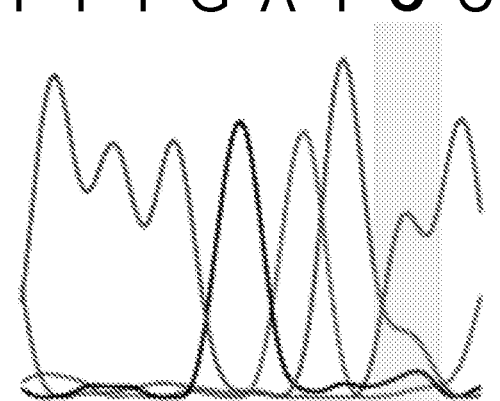
FIG. 3D

MSFDRNLLHNNGHNGYPNGTSAALRETGVIEKLLTSYGFIQCSERQARLFFHCSQYNGNLQDLKVGDDVEFEVSSDRRTG
KPIAVKLVKIKQEILPEERMNGQEVFYLTYTPEDVEGNVQLETGDKINFVIDNNKHTGAVSARNIMLLKKKQARCQGVVC
AMKEAFGFIERGDVVREIFFHYSEFKGDIETLQFGDDVEFTIKDRNGREVATDVRLLPQGTVIFEDISIEHFEGTVIKVI
PKVPSKNQNDPLPGRIKVDFVIPKEIPFGDKDTKSKVTLLEGDHVRENISTDRRDKLERATNIEVLSNTFQFTNEAREMG
VIAAMRDGFGFIKCVDRDVRMFFHFSEILDGNQLHIADEVEFTVVPDMLSAQRNHAIRIKKLPKGTVSFHSHSDHRFLGT
VEKEATFSNPKTTSPNKGKEKRAEDGIIAYDDCGVKLTIAFQAKDVEGSTSPQIGDKVEFSISDKQRPGQQVATCVRLLG
RNSNSKRLLGYVATLKDNFGFIETANHDKEIFFHYSEFSGDVDSLELGDMVEYSLSKGKGNKVSAERVNKTHSVNGITEE
ADPTTYSGKVIRPLRSVDPTQTEYQGMTEIVEEGDMKGEVYPFGTVGMANKGDCLQKGESVKFQLCVLGQNAQTMAYNIT
PLRRATVECVKDQFGFINYEVGDSKKLFHVKEVQDGIELQAGDEVEFSVILMQRTGKCSACNVWRVCEGPKAVAAPRPD
RLVNPLKNITLDDASAPRLMVLRQPRGPDNSMGFGAERKIRQAGVID (SEQ ID NO:2)

FIG. 7

ATGAGCTTTGATCAACCTTCTCCACAACAATGGGTACCCAATGGTACTTCAGCAGCACTTCGTGAAACTG
GGGTTATTGGAAAAACTCTTGACCTCTTTACGGATTCATTCAGTGTTCAGAACGCAAGCTAGACTTTTCTTCCACTGTTCACA
ATATAAATGGCAACCTCCAAGACTTAAAAGTAGGAGATGATGTTGAAGTATCATCTGACCGGAGGACTGGGAAACCT
ATTGCTATTAAATTGGTGAAGATAAAACCAGAATACATCCTGAAGACGAACGGAAGTTGTGTGCGCTGTTCCTC
ACAACTTAGAGAGTAAAATCTCCAGCTGCCCCGGGTCAGAGTCCAACAGGGAGTGTATGCTACGAACGTAATGGGAAGTATT
TTATCTGACTTACACCTCTGAGAGATGTGGAAGGGAATGTTCAGGAAACTGGAAACTGGAAAAAGAAGAAATTAACTTTGTAATTGATAAC
AATAAACACACTGGTGCTCGTAAGTGCTCGTAATATTATGCTGTGTTGTAAAAGAAGCAGGCTCGCTGTCAAGGAGTAGTTGTG
CCATGAAGGAGGCGGTTTGGCTTTATCGAAAGAGGGTGATGTTGTAAAGAGAGATATTCTTTCACTATAGTGAATTTAAAGGTGA
CCTAGAAAACCCTACAGCCTGAGATGACTGGAATTCACACAATCAAGGACAACAGAAATGGTAAAGAAGTTGCAACAGATGTCAGA
CTATTGCCTCAAGGAACAGTCATTTTGAGATATCAGCATTTGAAGGACTGTAACAAAGTTATCCCAAAAG
TACCCAGTAAAAAACCAGAAATGACCCATTGCCCAGGACGAATCAAAGTTGACTTTGTGATTCCTAAAGAACTTCCCTTTGGAGA
CAAAGACAACAAAATCCAACATAGAGGTTGACCCCTGCTGGAAGGTGACCATGTTAGGTTTAATATTTCAACACAGACCGACGTGACAAATTG
GAACGAGCAACCAACATAGAGGTTCTATCAAATACATTTCAGTTCACTAATGAAGCCAGAGAGATGGGTGTGATTGCTGCCA
TGAGAGATGGTTTTGGTTTCATCAAGTGTGTGGATCGTGATGCTCGTATGTTCTTCCACTTCAGTGAGATTCTAGATGGGGAA
CCAGCTCCCACATTGCAGATGAAGTAGAGTTACTGTGGTTCCTGATATGCTCCTCCAAAGAAATCATGCTATTAGGATT
AAAAAACTTCCCAAGGGCCACGGTTTCATTCCATTCCCATTCCAGATCATCGTTTTCTGGGCACCGTAGAAAAAAGAAGCCACTT
TTTCCAATCCTAAAACTACAAGCCCAAATAAAGGCAAAGACAAGGAGGCAAAGATGGCATTATAGCTTATGACGACTGTGG
GGTGAAACTGACGATTGCTCTTTTCAAGGCCAAGGATGTGAAGGATCTACTTCTCCTCAAATAGGAGATAAGGTTGAATTTAGT
ATTAGTGACAAACAGAGGCCTGGACAGCAGATTGCAACTTGCGGAGACTTTTAGGTCGTAATTCTAACTCCAAACGTCTCTT
GGGTTATGTGTGGCCAACTCTGAAAAGATAATTTGGATTTATAGAAACAGCTAATCATGATAAGGAAATATTTTCCACTATAGT
GAGTTCTCTGGTGATGTTGATAGCCTGGAACTGGGAGACATGGTTGAATACAGCTTGTTGTCCAAAGGCAATAAAGTCA
GTGCTGAGAAAGTAAACAAAGCCCACTGAGTCAGTGATGATTACTGAGGAAGCTAATCCACCATCTACTTCTGGTAAAGTCAT
TCGCCCCTCTGAGAGGTGTTGATCCAACACAGATTACCAAGGAATGATTGTGGAGGAGGGGGATATGAAAGGT
GAAGTGTATCCTTTTGGCATAGTTGGGATGGCCAACAAAAGGGGATTGCCTACAGAAAGGGAGAGTGTCAAGTTCCAGTTGT
GTGTACTTGGCCAAAATGCACAACAACTATGGCCTACACAACATCACACCCCCTTCGTAGGGCTACTGTGGAGTGTGTGAAGATCA
GTTTGGCTTTATTAACTATGAAGTAGGAGATAGGAGATAGCAAGAAGAGTCTCTGGAAAGTGAAGAAGTCGGTTGAGCTA
CAGGCAGGAGATGAGGTGGAAATTCAGTGGAATTCCTTAATCAGCGCACTGGGGAGTGCCTGTAATGTCTGGCGAGTCT
GTGAAGGCCCCAAAGCTGTTGCAATCGCCGGTTGGTCAATCAGACCTGCCTAAAGAACATCACCCTGGATGATGCCAG
TGCTCCACGTCTAATGGTTCTTCGTCGTGCAGATAACTCAATGGGATTTGGTGCAGAAGAAGATCCGTCAA
GCTGGTGGTGTCATTGACTAA (SEQ ID NO:3)

FIG. 8

IGR wild type (SEQ ID NO:10)

Passage 5 Virus recovered from Hep3B

IGR C-U Mutant
>90%

(SEQ ID NO:12)

Passage 5 Virus recovered from Hep3B-csde1^{C-T}

IGR C-U Mutant
>90%

(SEQ ID NO:12)

Passage 5 Virus recovered from
Hep3B VSV-IFN-ß ESC

IGR C-U Mutant
>30%

(SEQ ID NO:10)

Virus recovered from Hep3B tumor
which escaped VSV-IFN-ß in vivo

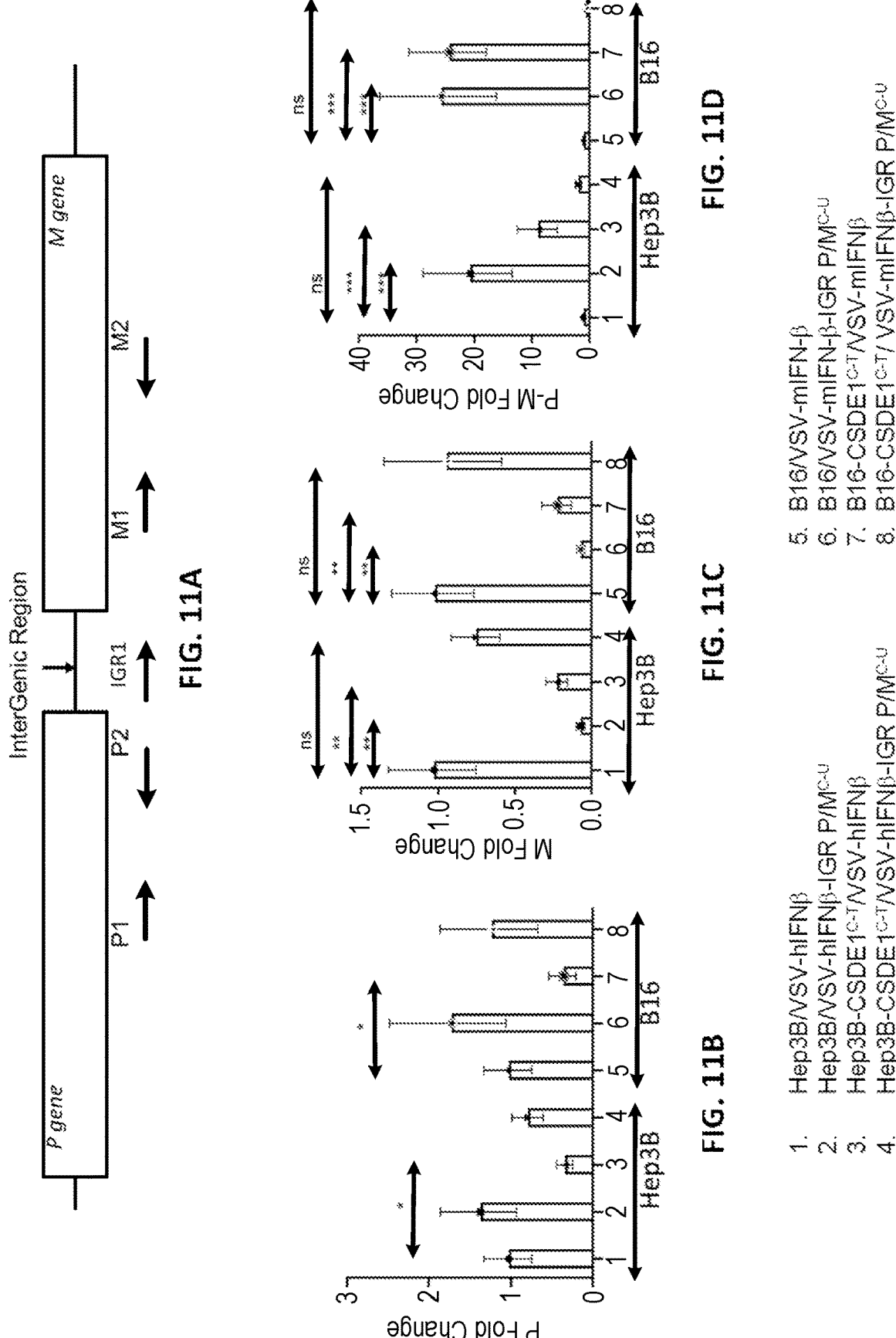

1. Hep3B/VSV-hIFNβ
2. Hep3B/VSV-hIFNβ-IGR P/M$^{C-U}$
3. Hep3B-CSDE1$^{C-T}$/VSV-hIFNβ
4. Hep3B-CSDE1$^{C-T}$/VSV-hIFNβ-IGR P/M$^{C-U}$

5. B16/VSV-mIFN-β
6. B16/VSV-mIFN-β-IGR P/M$^{C-U}$
7. B16-CSDE1$^{C-T}$/VSV-mIFNβ
8. B16-CSDE1$^{C-T}$/VSV-mIFNβ-IGR P/M$^{C-U}$

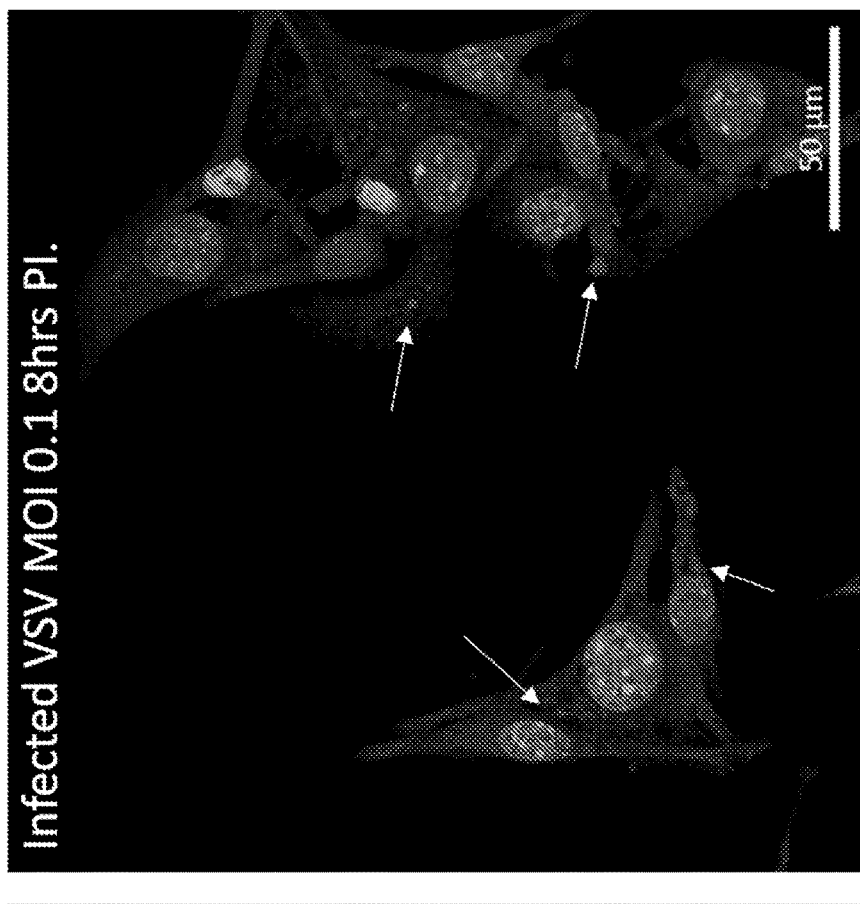
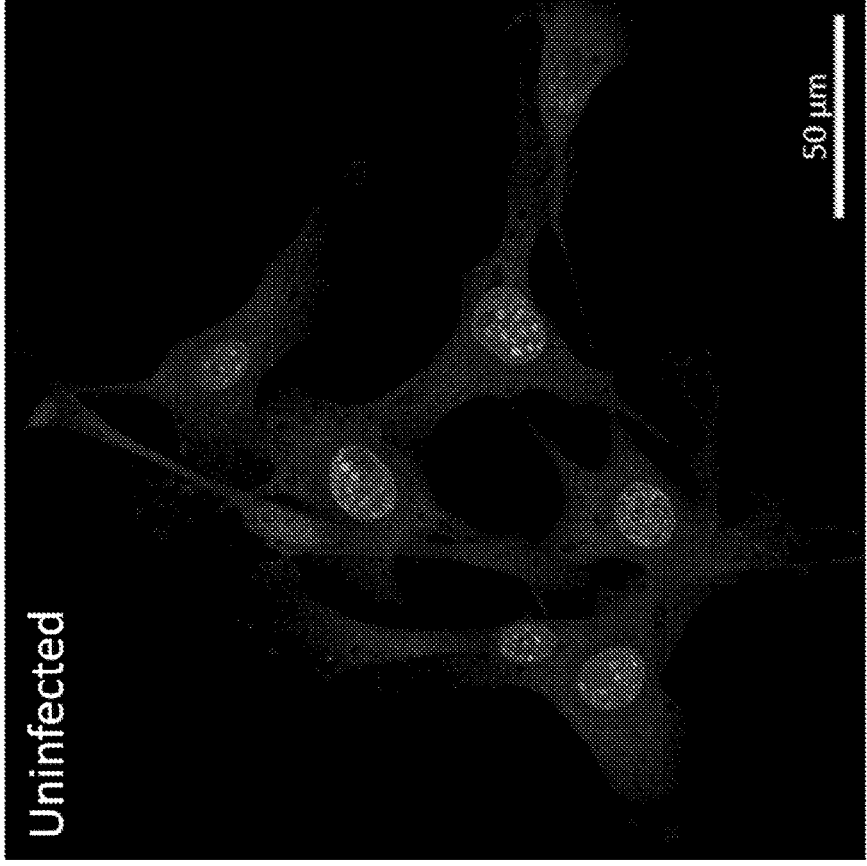
FIG. 13

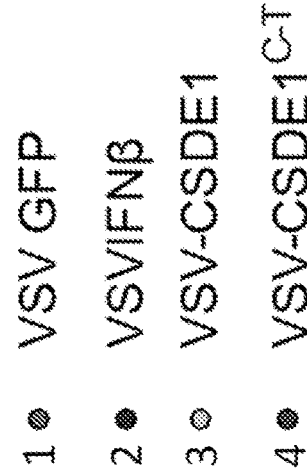
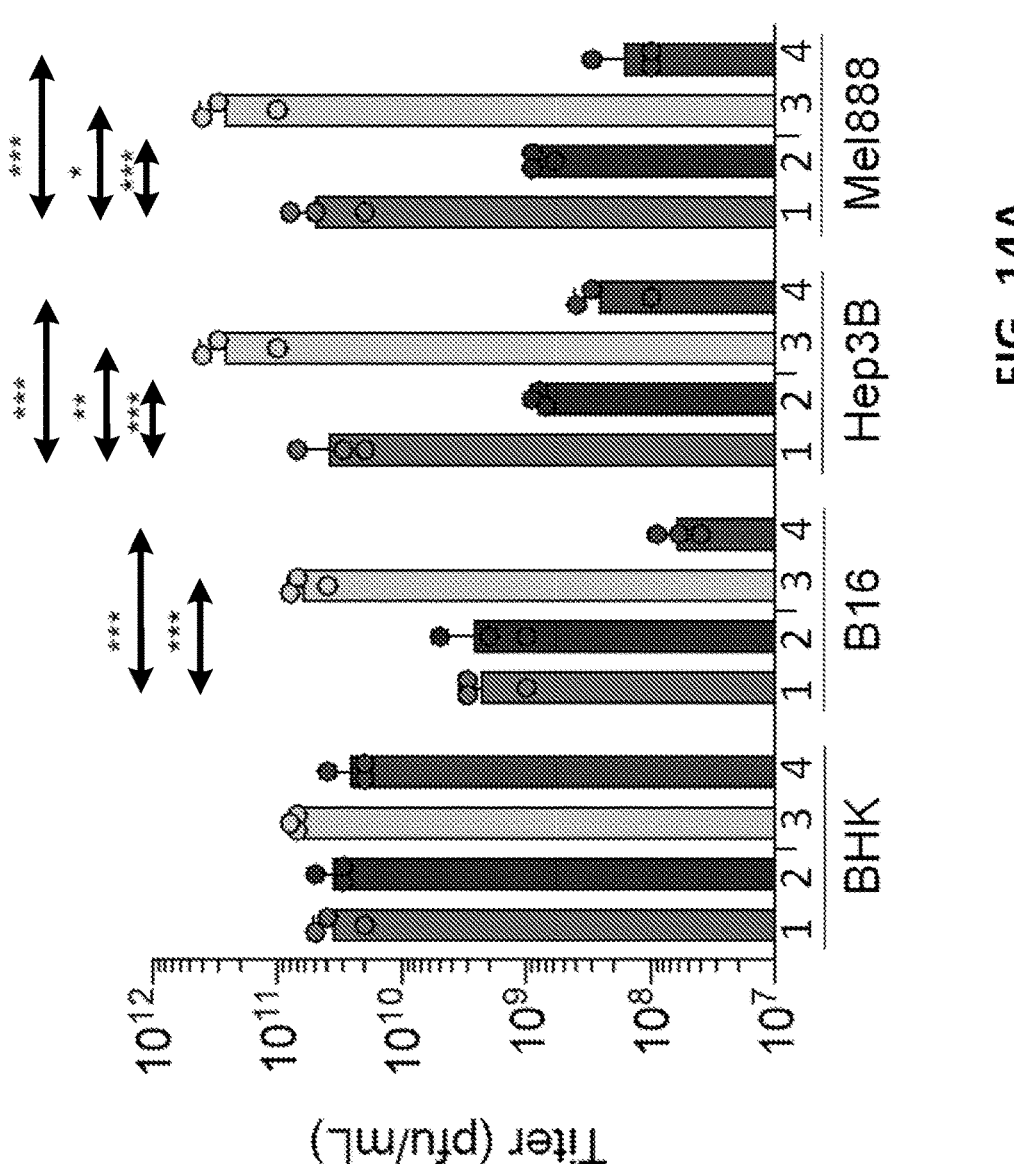
FIG. 14A

Expt 1:
Hep3B VSV-IFN-ß-
CSDE1<sup>WT</sup> ESC
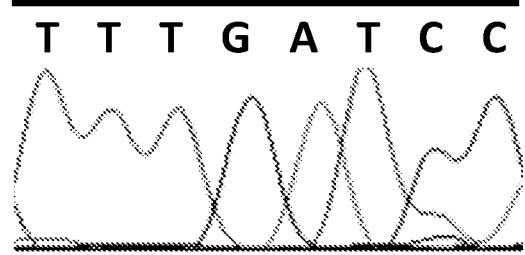
Expt 2:
Hep3B VSV-IFN-β-
CSDE1<sup>WT</sup> ESC
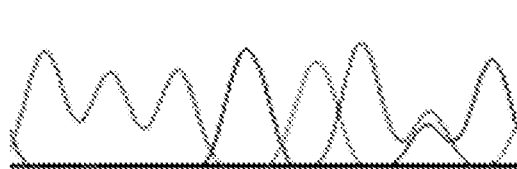
FIG. 14C

```
AAAATACAGATCACATTATTCACAATTATGGTTATTCTCAGATGTCTTATCCATAGACTTCATTGGACCATTCTCTATTCCACCACCCTCT
TGCAAATCCTATACAAGCCATTTTATCTGGGAAAGATAAGAATGAGTTGAGAGAGCTGGCAAATCTTTCTTCATTGCTAAGATCAGGAGAG
GGGTGGGAAGACATACATGTGAAATTCTTCACCAAGGACATATTATTGTGTCCAGAGGGAAATCAGACATGCTTGCAAGTTCGGGATTGCTAA
GGATAATAATAAAGACATGAGCATGAGCTATCCCCCTTGGGGAAGGGAATCCAGAGGGACAATTACAACAATCCCTGTTTATTATACGACCACCCTT
ACCCAAAGATGCTAGAGATGCCTCCAAGAATCCAAAATCCCCTGCTGTCCGGAATCAGGTTGGGCCAATTACCAACTGGCGCTCATTATAAA
ATTCGGAGTATATTACATGGAATGGGAATCCATTACACAGGGACTTCTTGAGTTGTGGACACGGGCTCCGGAGGGATGACTGCTGCATTACTACG
AGAAAATGTGCATAGCAGAGAGAATATTCAATAGTCTGTTAGAATTATCAGGGTGAAACATGTTGGGAATATCCATCTGACTTATGTGACCCCAGTGCCC
TAGAAACTTTAGGAGGAGGAGATAAATCGAGATGTGTAAATGGTGAAACATGTTGGGAATTAATGTAATGTAATTGATTAATTGATTGAGATATGGAAGTTCGGGATTCCTCTACTAGCCTGAAAAT
TATTTCCTCCGACTCAAAGCAGGCTTGGGGCTTCAAATTGATTTTCAAATTGATTGGATGAGCAAGGAGTTTAATCTACAAGACTTATGGAACATATATTTGTGAGACCG
AAAAGAATGCAGTAACAATCCTTGGTCCCATGTCCCATGTCCAAGACGGTCGACTTAGTTCAAACAGAATTAGTAGTTCTCAAACGTCTGAAGTATAT
ATGGTATGTAAAGGTTTGAAGAAATTAATCGATGAACCAATCCCGATTGGTCTTCCATCAATGAATCCTGAAAAAACCTGTACGCATTCCA
GTCATCAGAACAGGAGAATTGCCAGAGCAAAGAAGGTTAGTACATACTTTACCTGACAGTATTCCCTCCCAATTCATTCCTGATCCTTTTG
TAAACATTGAGACTATGCTACAAATATTCGGAGTACCCACGGGTGTCTCATCGCGGCTGCCTAAAATCATCTGATAGACCTGCAGATTTA
TTGACCATTAGCCTTTTTTATATGGCGATTATATCGTATTATAAACATCATCAGAGTAGGACCGATACCTCCGAACCCCCATCAGA
TGGAATTGCACAAAATGTGGGGATCGCTATAACTGGTATAAGCTTTTGGCTGAGTTTGATGGAGAAGACATTCCACTATATCAACAGTGTT
TAGCAGTTATCCAGCAATCATTCCCGATTAGGTGGGAGGCTGTTTCAGTAAAAGGAGGATACAAGCAGAAGTGGAGTACTAGAGGTGATGGG
CTCCCAAAAGATACCCGAATTTCAGACTCCTTGGCCCCAATCGGGAACTGGATCAGATCTCTGGAATTGGTCCGAATTGGTCGTCTAAA
TCCATTCAATGAGATCTTGTTCAATCAGCTATGTCTACAGTGATAATCATTTGAAATGGTCAAATTGCCAAGAAACACAGGAATGATTG
AATGGATCAATAGACGAATTTCAAAAGAAGAGACCGGTCTATACTGATGTTGAAGAGTGACCTACACGAGGAAAAACTCTTGGAGAGATTAAAAA
ATCATGAGGAGACTCCAAACTTTAAGTATGAAAAAAACTTTGATCCTTAAGACCCTCTTGTGGTTTTTATTTTTATCTCGTGGTTTGTGGTCT
TCGT (SEQ ID NO:16)
```

METHODS AND MATERIALS FOR TREATING CANCER

CROSS-REFERENCE TO RELATED APPLICATIONS

This application is a National Stage application under 35 U.S.C. § 371 of International Application No. PCT/US2021/051712 having an International Filing Date of Sep. 23, 2021, which claims benefit of priority from U.S. Provisional Application No. 63/082,297, filed on Sep. 23, 2020. The disclosure of the prior application is considered part of (and is incorporated by reference in) the disclosure of this application.

STATEMENT AS TO FEDERALLY SPONSORED RESEARCH

This invention was made with government support under CA210964 awarded by the National Institutes of Health. The government has certain rights in the invention.

SEQUENCE LISTING

This application contains a Sequence Listing that has been submitted electronically as an ASCII text file named 07039-1998WO1.txt. The ASCII text file, created on Sep. 22, 2021, is 29.7 kilobytes in size. The material in the ASCII text file is hereby incorporated by reference in its entirety.

TECHNICAL FIELD

This document relates to methods and materials for treating cancer. For example, this document provides methods and materials for using oncolytic viruses (e.g., replication-competent vesicular stomatitis viruses) to treat cancer. In some embodiments, this document provides replication-competent oncolytic viruses (e.g., replication-competent oncolytic vesicular stomatitis viruses), nucleic acid molecules encoding a replication-competent oncolytic virus (e.g., replication-competent oncolytic vesicular stomatitis virus), methods for making replication-competent oncolytic viruses (e.g., replication-competent oncolytic vesicular stomatitis viruses), and methods for using replication-competent oncolytic viruses (e.g., replication-competent oncolytic vesicular stomatitis viruses) to treat cancer. This document also provides cancer neoantigens, nucleic acids encoding a cancer neoantigen, and methods for stimulating immune cells (e.g., cytotoxic T lymphocytes) to kill cancer cells.

BACKGROUND INFORMATION

Many different oncolytic viruses can be used to treat cancer. One example is the vesicular stomatitis virus (VSV), which is a member of the Rhabdoviridae family. The VSV genome is a single molecule of negative-sense RNA that encodes five major polypeptides: a nucleocapsid (N) polypeptide, a phosphoprotein (P) polypeptide, a matrix (M) polypeptide, a glycoprotein (G) polypeptide, and a viral polymerase (L) polypeptide.

Escape from frontline cancer therapy is a major cause of treatment failure in cancer patients (Swanton et al., *Cancer Discov.*, 5(7):704-12 (2015); McGranahan et al., *Cancer Cell.*, 27(1):15-26 (2015); Stankova et al., *JAMA Oncol.*, 5(1):96-103 (2019); and Gatenby et al., *Cold Spring Harb. Perspect Med.*, 8(3) (2018)). Thus, a common clinical observation is that, irrespective of the type of treatment, a subset of patients initially develop promising clinical responses, followed by aggressive recurrence resulting in uncontrolled, lethal, tumor growth. Hence, strategies that reduce treatment failure through tumor escape would be highly significant.

SUMMARY

This document provides methods and materials for treating cancer. For example, this document provides replication-competent oncolytic viruses (e.g., replication-competent oncolytic vesicular stomatitis viruses), nucleic acid molecules encoding a replication-competent oncolytic virus (e.g., replication-competent oncolytic vesicular stomatitis virus), methods for making replication-competent oncolytic viruses (e.g., replication-competent oncolytic vesicular stomatitis viruses), and methods for using replication-competent oncolytic viruses (e.g., replication-competent oncolytic vesicular stomatitis viruses) to treat cancer. This document also provides cancer neoantigens, nucleic acids encoding a cancer neoantigen, and methods for stimulating immune cells (e.g., cytotoxic T lymphocytes) to kill cancer cells.

As described herein, cancer cells can escape the therapeutic effects of frontline or initial therapies such as oncolytic therapies by promoting mutagenesis of the cancer cell genome. As also described herein, one particular genomic mutation that repeatedly allows different types of cancer cells to escape treatment against the cancer is a C13T nucleic acid substitution in a cold shock domain-containing protein E1 (CSDE1) nucleic acid. This C13T nucleic acid substitution results in a P5S amino acid substitution in the CSDE1 polypeptide and creates a neoantigen (e.g., a neoantigen such as a class I and/or class II epitope that includes the P5S position or that includes a MSFDSNLLH (SEQ ID NO:1) sequence for mice or humans) that can be successfully targeted to kill those escaping cancer cells. For example, replication-competent oncolytic viruses (e.g., replication-competent oncolytic vesicular stomatitis viruses) can be designed to express a polypeptide that includes the P5S-containing neoantigen (e.g., a full length $CSDE1^{P5S}$ polypeptide or a fragment thereof that starts with amino acid residue 1, 2, 3, 4, or 5 of a $CSDE1^{P5S}$ polypeptide and extends to amino acid residue 100, 75, 50, 25, 20, 15, or 10 of a $CSDE1^{P5S}$ polypeptide) and used both as an oncolytic treatment against the cancer and as a vaccine treatment to induce a CSDE1-specific, anti-cancer immune response (e.g., a T cell response such as a CTL response) against cancer cells (e.g., cancer cells expressing a $CSDE1^{P5S}$ polypeptide and/or a wild-type CSDE1 polypeptide). In some cases, a fragment of a $CSDE1^{P5S}$ polypeptide can start with amino acid residue 1 and extend to amino acid residue 9 of a $CSDE1^{P5S}$ polypeptide)

In some cases, a full length $CSDE1^{P5S}$ polypeptide or a fragment thereof that includes P5S (e.g., a fragment that starts with amino acid residue 1, 2, 3, 4, or 5 of a $CSDE1^{P5S}$ polypeptide and extends to amino acid residue 100, 75, 50, 25, 20, 15, or 10 of a $CSDE1^{P5S}$ polypeptide), or nucleic acid encoding a full length $CSDE1^{P5S}$ polypeptide or a fragment thereof that includes P5S, can be used as described herein to induce a CSDE1-specific, anti-cancer immune response (e.g., a T cell response such as a CTL response) against cancer cells (e.g., cancer cells expressing a $CSDE1^{P5S}$ polypeptide and/or a wild-type CSDE1 polypeptide).

In general, one aspect of this document features a method for treating cancer in a mammal. The method comprises (or consists essentially of or consists of) administering, to the mammal, (a) a replication-competent oncolytic virus and (b) a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5S) or nucleic acid encoding the polypeptide. The mammal can be a human. The virus can be a vesicular stomatitis virus. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The method can comprise administering the polypeptide. The method can comprise administering the nucleic acid. The cancer can be selected from the group consisting of skin cancer, liver cancer, and kidney cancer.

In another aspect, this document features a replication-competent oncolytic virus comprising (or consisting essentially of or consisting of) nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5 S) or a nucleic acid sequence that is a template for the nucleic acid. The virus can be selected from the group consisting of a vesicular stomatitis virus, an adenovirus, and a herpesvirus. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide.

In another aspect, this document features a substantially pure polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1.

In another aspect, this document features a nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The nucleic acid can be a plasmid or viral vector.

In another aspect, this document features a composition comprising (a) a polypeptide and (b) an adjuvant, wherein the polypeptide comprises (or consists essentially of or consists of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The adjuvant can be selected from the group consisting of aluminum compound (e.g., amorphous aluminum hydroxyphosphate sulfate (AAHS), aluminum hydroxide, aluminum phosphate, or potassium aluminum sulfate (Alum)), monophosphoryl lipid A (MPL), oil in water emulsion composed of squalene, and cytosine phosphoguanine (CpG).

In another aspect, this document features a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human MS polypeptide.

In another aspect, this document features a composition comprising a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human NIS polypeptide.

In another aspect, this document features a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for treating cancer. The method comprises (or consists essentially of or consists of) administering a virus to a mammal comprising cancer cells, wherein the number of cancer cells within the mammal is reduced following the administration. The mammal can be a human. The virus can be:

(i) a replication-competent oncolytic virus comprising nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5 S) or a nucleic acid sequence that is a template for the nucleic acid. The virus can be selected from the group consisting of a vesicular stomatitis virus, an adenovirus, and a herpesvirus. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide, or (ii) a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human MS polypeptide.

In another aspect, this document features a method for treating cancer. The method comprises (or consists essentially of or consists of) administering a polypeptide to a mammal comprising cancer cells, wherein the number of cancer cells within the mammal is reduced following the administration. The mammal can be a human. The polypeptide can comprise (or consist essentially of or consist of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The nucleic acid can be a plasmid or viral vector.

In another aspect, this document features a method for treating cancer. The method comprises (or consists essentially of or consists of) administering a nucleic acid to a mammal comprising cancer cells, wherein the number of cancer cells within the mammal is reduced following the administration. The mammal can be a human. The nucleic acid can be:

(i) a nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The nucleic acid can be a plasmid or viral vector; or (ii) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for treating cancer. The method comprises (or consists essentially of or consists of) administering a composition to a mammal comprising cancer cells, wherein the number of cancer cells within the mammal is reduced following the administration. The mammal can be a human. The composition can be:

(i) a composition comprising (a) a polypeptide and (b) an adjuvant, wherein the polypeptide comprises (or consists essentially of or consists of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The adjuvant can be selected from the group consisting of aluminum compound (e.g., amorphous aluminum hydroxyphosphate sulfate (AAHS), aluminum hydroxide, aluminum phosphate, or potassium aluminum sulfate (Alum)), monophosphoryl lipid A (MPL), oil in water emulsion composed of squalene, and cytosine phosphoguanine (CpG); or (ii) a composition comprising a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human MS polypeptide.

In another aspect, this document features a method for increasing survival of a mammal having cancer. The method comprises (or consists essentially of or consists of) administering a virus to the mammal. The mammal can be a human. The virus can be:

(i) a replication-competent oncolytic virus comprising nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5 S) or a nucleic acid sequence that is a template for the nucleic acid. The virus can be selected from the group consisting of a vesicular stomatitis virus, an adenovirus, and a herpesvirus. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide; or (ii) a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human MS polypeptide.

In another aspect, this document features a method for increasing survival of a mammal having cancer. The method comprises (or consists essentially of or consists of) administering a polypeptide to the mammal. The mammal can be a human. The polypeptide comprises (or consists essentially of or consists of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1.

In another aspect, this document features a method for increasing survival of a mammal having cancer. The method comprises (or consists essentially of or consists of) administering a nucleic acid to the mammal. The mammal can be a human. The nucleic acid can be:

(i) a nucleic acid encoding a polypeptide comprising (or consisting essentially of or consisting of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The nucleic acid can be a plasmid or viral vector; or (ii) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for increasing survival of a mammal having cancer. The method comprises (or consists essentially of or consists of) administering a composition to the mammal. The mammal can be a human. The composition can be:

(i) a composition comprising (a) a polypeptide and (b) an adjuvant, wherein the polypeptide comprises (or consists essentially of or consists of) the amino acid sequence set forth in SEQ ID NO:1 (or the amino acid sequence of a CSDE1$^{P5S}$ polypeptide that is at least 9 amino acids in length and includes P5S). The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The polypeptide can comprise a cell penetrating amino acid sequence. The cell penetrating amino acid sequence can be selected from Table 1. The adjuvant can be selected from the group consisting of aluminum compound (e.g., amorphous aluminum hydroxyphosphate sulfate (AAHS), aluminum hydroxide, aluminum phosphate, or potassium aluminum sulfate (Alum)), monophosphoryl lipid A (MPL), oil in water emulsion composed of squalene, and cytosine phosphoguanine (CpG); or (ii) a composition comprising a replication-competent vesicular stomatitis virus comprising an RNA molecule, wherein the RNA molecule comprises (or consists essentially of or consists of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:1 (or the amino acid sequence of a CSDE1$^{P5S}$ polypeptide that is at least 9 amino acids in length and includes P5S), and a nucleic acid sequence that is a template for a positive sense transcript encoding a VSV L polypeptide. The polypeptide can be a full length CSDE1$^{P5S}$ polypeptide. The polypeptide can comprise less than 100 amino acid residues. The polypeptide can comprise less than 50 amino acid residues. The polypeptide can comprise less than 25 amino acid residues. The polypeptide can comprise less than 100 amino acid residues of a full length CSDE1$^{P5S}$ polypeptide. The polypeptide can comprise less than 50 amino acid residues of a full length CSDE1$^{P5S}$ polypeptide. The polypeptide can comprise less than 25 amino acid residues of a full length CSDE1$^{P5S}$ polypeptide. The RNA molecule can comprise a nucleic acid sequence that is a template for a positive sense transcript encoding a interferon-β polypeptide. The interferon-β polypeptide can be a human interferon-β polypeptide. The RNA molecule can comprise a nucleic acid sequence that is a template for a positive sense transcript encoding a NIS polypeptide. The NIS polypeptide can be a human MS polypeptide.

In another aspect, this document features a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The virus can comprise an antigen or nucleic acid encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The virus can comprise an antigen or nucleic acid encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The RNA molecule can comprise a nucleic acid sequence that is a template for a positive sense transcript encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a composition comprising (or consisting essentially of) a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The virus can comprise an antigen or nucleic acid encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a composition comprising (or consisting essentially of) a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The virus can comprise an antigen or nucleic acid encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a composition comprising (or consisting essentially of) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The RNA molecule can comprise a nucleic acid sequence that is a template for a positive sense transcript encoding an antigen. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a composition comprising (or consisting essentially of) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for treating cancer in a mammal, where the method comprises (or consists essentially of or consists of) administering, to the mammal, (a) a replication-competent oncolytic virus and (b) a polypeptide comprising (or consisting essentially of or consisting of) the amino acid sequence set forth in SEQ ID NO:2 or a fragment thereof, or nucleic acid encoding the polypeptide or the fragment thereof. The mammal can be a human. The virus can be a vesicular stomatitis virus. The virus can comprise the polypeptide comprising the amino acid sequence set forth in SEQ ID NO:2. The virus can comprise the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The polypeptide can comprise a cell penetrating amino acid sequence. The cell penetrating amino acid sequence can be selected from Table 1. The method can comprise administering the polypeptide. The method can comprise administering the nucleic acid. The cancer can be selected from the group consisting of skin cancer, liver cancer, and kidney cancer.

In still another aspect, this document features a method for treating cancer, where the method comprises (or consists essentially of or consists of) administering a virus to a mammal comprising cancer cells, where the number of cancer cells within the mammal is reduced following the administration. The mammal can be a human. The virus can be:

(i) a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2, or (ii) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2.

In another aspect, this document features a method for treating cancer, where the method comprises (or consists essentially of or consists of) administering a nucleic acid to a mammal comprising cancer cells, where the number of cancer cells within the mammal is reduced following the administration. The mammal can be a human. The nucleic acid can be:

> (i) a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or
>
> (ii) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for treating cancer, where the method comprises (or consists essentially of or consists of) administering a composition to a mammal comprising cancer cells, where the number of cancer cells within the mammal is reduced following the administration. The mammal can be a human. The composition can be:

> (i) a composition comprising (or consisting essentially of) a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or > (ii) a composition comprising (or consisting essentially of) a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or
>
> (iii) a composition comprising (or consisting essentially of) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2, or
>
> (iv) a composition comprising (or consisting essentially of) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for increasing survival of a mammal having cancer, where the method comprises (or consists essentially of or consists of) administering a virus of to the mammal. The mammal can be a human. The virus can be:

(i) a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2, or (ii) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2.

In another aspect, this document features a method for increasing survival of a mammal having cancer, where the method comprises (or consists essentially of or consists of) administering a nucleic acid to the mammal. The mammal can be a human. The nucleic acid can be:

(i) a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or (ii) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In yet another aspect, this document features a method for increasing survival of a mammal having cancer, where the method comprises (or consists essentially of or consists of)

administering a composition to the mammal. The mammal can be a human. The composition can be:

(i) a composition comprising (or consisting essentially of) a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or (ii) a composition comprising (or consisting essentially of) a nucleic acid encoding a replication-competent oncolytic virus comprising (or consisting essentially of or consisting of) (a) a polypeptide comprising (or consisting essentially of or consisting of) the amino acid sequence set forth in SEQ ID NO:2 or a fragment thereof, or (b) nucleic acid encoding the polypeptide or a nucleic acid sequence that is a template for the nucleic acid. The nucleic acid can be a plasmid or viral vector. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid, or (iii) a composition comprising (or consisting essentially of) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2, or (iv) a composition comprising (or consisting essentially of) a nucleic acid molecule comprising (or consisting essentially of or consisting of) a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, and a nucleic acid sequence that is a template for a positive sense transcript encoding a VSV L polypeptide. The nucleic acid strand can comprise the nucleic acid sequence that is a template for a positive sense transcript encoding a polypeptide comprising the amino acid sequence set forth in SEQ ID NO:2. The nucleic acid strand can comprise the nucleic acid sequence that is a template for a positive sense transcript encoding a polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The nucleic acid strand can comprise a nucleic acid sequence that is a template for a positive sense transcript encoding a interferon-β polypeptide. The interferon-β polypeptide can be a human interferon-β polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for inducing an immune response in a mammal, where the method comprises (or consists essentially of) administering a virus to the mammal. The mammal can be a human. The virus can be:

(i) a replication-competent oncolytic virus comprising (or consisting essentially of or consisting of) (a)(1) a polypeptide comprising (or consisting essentially of or consisting of) the amino acid sequence set forth in SEQ ID NO:2 or a fragment thereof and (a)(2) an antigen, or (b)(1) nucleic acid encoding the polypeptide or a nucleic acid sequence that is a template for the nucleic acid and (b)(2) nucleic acid encoding the antigen. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen, or (ii) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, a nucleic acid sequence that is a template for a positive sense transcript encoding a VSV L polypeptide, and a nucleic acid sequence that is a template for a positive sense transcript encoding an antigen. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a method for inducing an immune response in a mammal, where the method comprises (or consists essentially of or consists of) administering a nucleic acid encoding a virus to the mammal. The mammal can be a human. The virus can be:

(i) a replication-competent oncolytic virus comprising (or consisting essentially of or consisting of) (a)(1) a polypeptide comprising (or consisting essentially of or consisting of) the amino acid sequence set forth in SEQ ID NO:2 or a fragment thereof and (a)(2) an antigen, or (b)(1) nucleic acid encoding the polypeptide or a nucleic acid sequence that is a template for the nucleic acid and (b)(2) nucleic acid encoding the antigen. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen, or (ii) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, a nucleic acid sequence that is a template for a positive sense transcript encoding a VSV L polypeptide, and a nucleic acid sequence that is a template for a positive sense transcript encoding an antigen. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

In another aspect, this document features a method for inducing an immune response in a mammal, where the method comprises (or consists essentially of or comprises) administering to the mammal (i) a composition comprising (or consisting essentially of) a virus, or (ii) a composition comprising (or consisting essentially of) a nucleic acid encoding the virus. The mammal can be a human. The virus can be:

(i) a replication-competent oncolytic virus comprising (or consisting essentially of or consisting of) (a)(1) a polypeptide comprising (or consisting essentially of or consisting of) the amino acid sequence set forth in SEQ ID NO:2 or a fragment thereof and (a)(2) an antigen, or (b)(1) nucleic acid encoding the polypeptide or a nucleic acid sequence that is a template for the nucleic acid and (b)(2) nucleic acid encoding the antigen. The virus can be a vesicular stomatitis virus, an adenovirus, or a herpesvirus. The virus can comprise the polypeptide comprising the amino acid sequence set forth in SEQ ID NO:2, or the polypeptide comprising the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The virus can comprise the nucleic acid. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen, or (ii) a replication-competent vesicular stomatitis virus comprising (or consisting essentially of or consisting of) an RNA molecule, where the RNA molecule comprises (or consists of or consists essentially of) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a polypeptide comprising the amino acid sequence set forth in SEQ ID NO:2 or a fragment thereof, a nucleic acid sequence that is a template for a positive sense transcript encoding a VSV L polypeptide, and a nucleic acid sequence that is a template for a positive sense transcript encoding an antigen. The RNA molecule can comprise the nucleic acid sequence that is a template for a positive sense transcript encoding the polypeptide comprising the amino acid sequence set forth in SEQ ID NO:2. The RNA molecule can comprise the nucleic acid sequence that is a template for a positive sense transcript encoding the fragment of SEQ ID NO:2. The fragment of SEQ ID NO:2 can comprise at least 750 amino acid residues of SEQ ID NO:2. The fragment of SEQ ID NO:2 can comprise at least 700 amino acid residues of SEQ ID NO:2. The antigen can be from a virus or a bacteria. The antigen can be from a SARS-CoV-2 virus, an influenza virus, an EBOLA virus, a yellow fever virus, a dengue virus, a coronavirus, a measles virus, a mumps virus, or a rubella virus. The antigen can be from an *Escherichia* species, a *Salmonella* species, a *Mycobacterium* species, a *Clostridium* species, a *Bacillus* species, or a *Leptospira* species. The antigen can be a SARS-CoV-2 antigen. The antigen can be a SARS-CoV-2 SPIKE protein antigen, a SARS-CoV-2 M protein antigen, a SARS-CoV-2 N protein antigen, an influenza NP protein antigen, an influenza M1 protein antigen, an influenza NS1 protein antigen, an Ebola NP protein antigen, an Ebola GP protein antigen, an Ebola VP35 protein antigen, an Ebola VP40 protein antigen, a yellow fever NS1 protein antigen, a dengue virus NS1 protein antigen, a coronavirus spike protein antigen, a coronavirus M protein antigen, a coronavirus N protein antigen, a measles virus F protein antigen, a measles virus H protein antigen, a mumps nucleocapsid protein antigen, a rubella virus E1 spike protein antigen, a rubella virus E2 spike protein antigen, a rubella virus C protein antigen, an *Escherichia coli* O antigen, a *Mycobacterium tuberculosis* glfT2 antigen, a *Mycobacterium tuberculosis* fas antigen, a *Mycobacterium tuberculosis* iniB antigen, a *Clostridium tatanis* tetanus toxoid antigen, a *Bacillus anthracis* anthrax toxin antigen, a *Leptospira* species LipL21 antigen, a *Leptospira* species LipL41 antigen, or a *Leptospira* species LipL32 antigen.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1J. Escape from VSV-IFN-β selects for the CSDE1$^{C-T}$ mutation. B16 murine melanoma or Hep3B human HCC cells were infected (MOI 0.01) for 21 days. Surviving cells were pooled, and genomic DNA prepared. Sanger sequencing of CSDE1 is shown for: (FIG. 1A) Parental, uninfected B16 showing a homogenous population of wild type CSDE1 sequence; (FIG. 1B) B16-VSV-GFP-ESC showing a mixed population of escape cells with either wild type ATCC or mutated ATTC sequence; (FIG. 1C) B16 cells stably expressing the HSVtk suicide gene and selected in GCV for 21 days; (FIG. 1D) B16-VSV-IFN-β-ESC showing a nearly homogenous population of escape cells with mutated ATTC sequence; (FIGS. 1E and 1F) B16 cells stably expressing shRNA against APOBEC3 selected for escape from VSV-GFP (FIG. 1E) or VSV-IFNβ (FIG. 1F); (FIG. 1G) Parental, uninfected Hep3B; (FIG. 1H) Hep3B-VSV-GFP-ESC; and (FIG. 1I) Hep3B-VSV-IFNβ-ESC. (FIG. 1J) Mice bearing s.c. Mel888 human melanoma tumors treated with i.t. VSV-hIFNβ were excised upon escape from treatment, genomic DNA prepared, and Sanger sequencing used to characterize the CSDE1 gene as shown. Four of four excised, VSV-hIFNβ-escaped tumors had mixed populations of CSDE1$^{WT}$ and CSDE1$^{C-T}$ tumor cells at ratios close to 1:1. Results were representative of multiple (>5) separate experiments (FIGS. 1A-1D); three separate experiments (FIGS. 1E and 1F) and (FIGS. 1G-1I); and four separate escape tumors (FIG. 1J).

(FIGS. 2B-2D) 48 hours following transfection with siRNA as in (FIG. 2A), Hep3B cells were infected with VSV-GFP (MOI 0.1). 48 hours (FIG. 2B) or 96 hours (FIG. 2C) later, viral titers were determined by plaque assay, and (FIG. 2D) the number of surviving cells was counted at 96 hours post infection. Representative of two separate experiments. (FIG. 2E) B16, B16-CSDE1$^{C-T}$ or B16-CSDE1$^{WT}$ over-expressing cells were infected with VSV-IFN-β at a MOI of 0.1. 24, 48, and 72 hours later, viral titers were measured on BHK cells by plaque assay. Representative of multiple experiments. (FIG. 2F) Parental Hep3B cells, or pooled populations of Hep3B over-expressing wild type CSDE1$^{WT}$, or mutant CSDE1$^{C-T}$, were infected with VSV-IFN-β (MOI 0.1) (3 wells/group). 48 hours later, (Passage 1) supernatants were assayed for infectious titers on the same cells on which the virus was passaged. Virus was recovered every 48 hours (Passages 2-5), and the titer similarly determined. Representative of three separate experiments. (FIG. 2G) Stock VSV-IFN-β virus, or VSV-IFN-β that had been passaged 5 times through Hep3B parental or Hep3B-CSDE1$^{C-T}$ cells as in (FIG. 2F) had their titers determined on either Hep3B parental cells or on Hep3B-CSDE1$^{C-T}$ cells. Representative of two separate experiments. Means±SD of 3 technical replicates are shown. P-values were determined using a one way (FIGS. 2B, 2C, and 2D) or two-way (FIGS. 2E, 2G, and 2F) ANOVA with a Tukey multiple comparisons post-test on log transformed data. Statistical significance set at p<0.05, ns>0.05.

FIGS. 3A-3D. CSDE1 expressed from the virus enhances replication. (FIG. 3A) Viruses expressing CSDE1$^{WT}$ and CSDE1$^{C-T}$ were constructed and validated by Western Blot for expression of CSDE1. Stars indicate clones that were used in subsequent experiments. (FIG. 3B) BHK (hamster), B16 (mouse), Hep3B and Mel888 (human) cell lines were infected with VSV-GFP, VSV-hIFN-β, VSV-CSDE1$^{WT}$ or VSV-CSDE1$^{C-T}$ at an MOI of 3 (triplicate wells per cell line). 48 hours later, the titer was determined on BHK cells by plaque assay. Representative of multiple experiments. (FIG. 3C) Murine B16 or human Hep3B cells were infected (MOI 0.01) with VSV-IFNβ, VSV-IFN-β-CSDE1$^{WT}$ or with VSV-IFN-β-CSDE1$^{C-T}$ viruses (using species matched IFNβ genes) for 21 days. Surviving cells were pooled and counted. (FIG. 3D) Hep3B cells were infected (MOI 0.01) with the VSV-hIFN-β-CSDE1$^{WT}$ virus for 21 days. Surviving cells were pooled, and genomic DNA prepared. Sanger sequencing of CSDE1 is shown for two independent experiments. In these experiments, as well as in two other experiments, a mixed population of mutated and un-mutated cells were selected. Means±SD of 3 technical replicates are shown. P-values were determined using a two way (FIG. 3B) or one-way (FIG. 3C) ANOVA with a Tukey multiple comparisons post-test on log transformed data. Statistical significance set at p<0.05, ns>0.05.

(FIG. 4A) C57Bl/6 mice bearing 10-day B16 tumors were injected i.t. with PBS, VSV-mIFNβ, VSV-mIFNβ-CSDE1$^{WT}$ or VSV-mIFNβ-CSDE1$^{C-T}$. (FIG. 4B) Splenocytes harvested at day 30 were re-stimulated with VSV-N-specific immunodominant peptide (N$_{52-59}$), SIIN-FEKL (SEQ ID NO:14) peptide from OVA, or with B16 cells over-expressing CSDE1$^{WT}$ or CSDE1$^{C-T}$, or with B16 or B16ova cells (E:T 10:1) for 72 hours. Supernatants were assayed for IFN-γ. Representative of two separate experiments. (FIGS. 4C and 4D) Mice were injected with viruses as in (FIG. 4A) with added groups (3 mice/group) which received no ICB, or anti-PD-1 antibody i.p. at days 10, 12, and 14 or at days 14, 17, and 21. 24 hours after the last injection of virus (day 22), or earlier if tumor>1.0 cm diameter (PBS groups), tumors were dissociated and assayed for (FIG. 4C) IL-12 or (FIG. 4D) TNF-α by ELISA (normalized by protein concentration in whole tumor lysates as pg/mL protein). (FIG. 4E) C57Bl/6 mice with 10-day B16 tumors were injected i.t. with PBS, VSV-mIFNβ, VSV-mIFNβ-CSDE1$^{WT}$ or with VSV-mIFNβ-CSDE1$^{C-T}$ (10$^7$ pfu/injection) followed by anti-PD-1 antibody (n=8/group). (FIG. 4F) Kaplan-Meier survival for groups in (FIG. 4E). P-values were determined using the Log-rank Mantel Cox test. For multiple comparisons using the Bonferroni correction, overall statistical significance threshold was set at α=0.05 (3 comparisons at p<0.0125 (4 comparisons)). Representative of two separate experiments. (FIG. 4G) C57Bl6 mice with 10-day B16 tumors were injected i.t. with (column 1) PBS, (2) VSV-mIFNβ, (3) VSV-mIFNβ-CSDE1$^{WT}$ or (4) VSV-mIFNβ-CSDE1$^{C-T}$ (10$^7$ pfu/injection) on days 10, 11, and 12. On day 13, tumors were excised, and virus measured by plaque assay on BHK cells. Representative of two separate experiments. Each symbol in (FIG. 4B), (FIG. 4C), (FIG. 4D), and (FIG. 4G) represents a mouse (n=3/group). Means±SD are shown. ND, not detected (below limit of detection). P-values were determined using a two-way (FIG. 4B) or one-way ANOVA (FIGS. 4C, 4D, and 4G) with a Tukey multiple comparisons post-test. Statistical testing was performed on log transformed data in (FIG. 4G). Statistical significance set at p<0.05 for (FIG. 4B), (FIG. 4C), (FIG. 4D), and (FIG. 4G).

(FIG. 5A) In vitro IL-4/GM-CSF matured murine DC were transfected with nothing, CSDE1$^{WT}$ or CSDE1$^{C-T}$ expression plasmids and 48 hours later administered as vaccines with i.t. treatments with VSV-mIFN-β and anti-PD1. (FIG. 5B) On day 40, spleens and LN were assayed for IFN-γ following in vitro re-stimulation with live B16 cells or with live B16 cells stably expressing CSDE1$^{C-T}$. WT: DC vaccines expressing wild type CSDE1; * DC vaccine expressing mutated CSDE1$^{C-T}$. (FIG. 5C) C57Bl/6 mice with 10-day B16 tumors were injected i.t. with PBS or with VSV-mIFN-β, (10$^7$ pfu/injection) and i.p. with unloaded DC (DC), DC vaccine expressing wild type CSDE1 (DC-CSDE1$^{WT}$) or with DC vaccine expressing mutated CSDE1$^{C-T}$ (CSDE1$^{C-T}$) followed by anti-PD-1 (n=8/group) as shown in (FIG. 5A). Kaplan-Meier survival for groups is shown. Representative of two separate experiments. P-values were determined using the Log-rank Mantel Cox test. For multiple comparisons using the Bonferroni correction, overall statistical significance threshold was set at α=0.05 (3 comparisons at p<0.0167). (FIG. 5D) Mice were injected as in (FIG. 5A) (3 mice/grp). 24 hours after the last injection of virus (day 22), or earlier if tumor size exceeded 1.0 cm diameter in the PBS groups, tumors were excised and assayed for IL-12 or TNF-α by ELISA (normalized by protein concentration in whole tumor cell lysates and expressed as pg/mL protein). Representative of two separate experiments. Each symbol in (FIG. 5B) and (FIG. 5D) represents a mouse (n=2 or 3/group). Means±SD are shown. ND, not detected (below limit of detection). P-values were determined using a two-way ANOVA (FIG. 5B) with a Tukey multiple comparisons post-test. Statistical significance set at p<0.05 for (FIG. 5B).

(FIG. 6A) Human CD3+ T cells activated in vitro with anti-CD3 and anti-CD28 antibodies and co-cultured with CD14$^+$-matured DC (same donor PBMC) were cultured with different Hep3B cell lysates. Lysates were re-added on days 3 and 5. On day 7, CD3+ T cells were isolated and co-cultured with autologous DC and the same Hep3B cell lysates (E:T 10:1). (FIG. 6B) 72 hours later, supernatants were assayed for IFN-γ. Means±SD of 3 technical replicates from 3 donors. (FIG. 6C) 10$^4$ target cells (Hep3BP parental or Hep3B-VSV-hIFN-β 21d ESC) were treated for 24 hours with hIFN-γ before being co-cultured with 10$^5$ T cells primed/expanded on either Hep3BP or Hep3B-VSV-hIFNβ-21d-ESC cells as in (FIG. 6A). A further 10$^5$ T cells were added after 48 hours. At 120 hours post co-culture, wells were washed ×3 with PBS, and surviving adherent cells counted. (FIG. 6D) NetMHC4.0% Rank of the predicted affinity of the un-mutated CSDE1$^{WT}$ 9-mer, MSFDPNLLH (SEQ ID NO:17), and its CSDE1$^{C-T}$ mutated counterpart 9-mer, MSFDSNLLH (SEQ ID NO:18), compared to 400,000 random natural peptides for HLA subtypes. Strong binders defined as % rank <0.5, and weak binders with % rank <2 (cbs.dtu.dk/services/NetMHC/). (FIG. 6E) Human CD3+ T cells activated in vitro and co-cultured with autologous DC were cultured with Hep3BP or Hep3B-VSV-hIFNβ-ESC lysates, or with DC transfected 48 hours previously with 10 μg pcDNA3.1-CSDE1$^{WT}$ or pcDNA3.1-CSDE1$^{C-T}$ plasmids. Lysates, or transfected DC, were re-added on day 5. On day 7, isolated CD3+ T cells were co-cultured with DC and the same Hep3B cell lysates or with similarly transfected DC (E:T 10:1). 72 hours later, supernatants were assayed for IFN-γ. Means±SD of 3 technical replicates from two donors. ND, not detected (below limit of detection). P-values were determined using a one-way (FIG. 6B) or two-way (FIG. 6C) ANOVA with a Tukey multiple comparisons post-test. Statistical testing was performed on log transformed data in (FIG. 6C). Statistical significance set at p<0.05, ns>0.05.

FIG. 7 is an amino acid sequence listing for a human CSDE1 polypeptide (SEQ ID NO:2).

FIG. 8 is a nucleic acid sequence listing that encodes a wild-type mouse CSDE1 polypeptide (SEQ ID NO:3). The C at position 13 (bold, underlined, enlarged) is a wild-type nucleotide that can be mutated to a T in cancer cells escaping treatment.

FIGS. 10A-10E. VSV-IFNβ was passaged 5 times through Hep3B or Hep3B-CSDE1$^{C-T}$ cells. Sanger sequence was obtained for the IGR between the P and M genes (FIG. 10A) from virus populations passaged through: (FIG. 10B) Hep3B (a homogenous population of wt sequence), (FIG. 10C) Hep3B-CSDE1$^{C-T}$ cells, or (FIG. 10D) Hep3B-VSV-IFNβ-21d-ESC cells (largely homogenous for point mutation C-U); and (FIG. 10E) virus population from a Hep3B tumor in a SCID mouse that escaped VSV-IFNβ (a heterogenous population of wt and mutant IGR P/M viruses).

FIGS. 11A-11I. CSDE1 regulates viral M RNA. HepB3, HepB3-CSDE1$^{C-T}$, B16, or B16-CSDE1$^{C-T}$ cells were infected with VSV viruses (VSV-IFNβ or VSV-IFNβ-IGR P/M$^{C-U}$) (MOI 3). Lanes: 1. Hep3BNSV-hIFNβ; 2: Hep3BNSV-hIFNβ-IGR P/M$^{C-U}$; 3: Hep3B-CSDE1$^{C-T}$/VSV-hIFNβ; 4. Hep3B-CSDE1$^{C-T}$/VSV-hIFNβ-IGR P/M$^{C-U}$; 5. B16/VSV-mIFNβ; 6: B16NSV-mIFNβ-IGR P/M$^{C-U}$; 7: B16-CSDE1$^{C-T}$/VSV-mIFNβ; 8. B16-CSDE1$^{C-T}$/VSV-mIFNβ-IGR P/M$^{C-U}$. Six (6) hours later, qrtPCR was used to assess levels of (FIG. 11B) viral P RNA (primers P1 and P2); (FIG. 11C) viral M RNA (M1 and M2); or (FIG. 11D) viral P-M RNA (P/M IGR-M specific primers IGR1 and M2). Primer locations are indicated in FIG. 11A. Data plotted are representative of 3 experiments. Levels of G, L, and G-L RNA also were measured using primers G1 and G2 (FIG. 11F), L1 and L2 (FIG. 11G), and G1 and L2 (FIG. 11H); primer locations are indicated in FIG. 11E. RNA levels were normalized to expression in Hep3B or B16 infected with VSV-hIFNβ. (FIG. 11I) Hep3B parental cells (Hep3B) (lanes 1-3), or Hep3B cells engineered to overexpress CSDE1$^{wt}$ (Hep3B-CSDE1$^{wt}$) (lanes 4 and 5) or mutated CSDE1$^{P5S}$ (Hep3B-CSDE1$^{C-T}$) (lanes 6 and 8) proteins, or Hep3B selected in vitro for resistance to VSV-IFNβ oncolysis for 21 days (Hep3B-VSV-IFNβ-ESC) (lanes 7 and 9), were infected with VSV-IFNβ (lanes 2, 5, 6, and 7), or VSV-IFNβ-IGR P/M$^{C-U}$ (lanes 3, 4, 8, and 9) (MOI 3). Cells were harvested at 6 or 18 hours post infection, and viral M protein was measured by Western Blot.

FIG. 13. VSV infection is associated with concentration of CSDE1 in cytoplasmic compartments. Immunofluorescence of CSDE1 in uninfected B16 cells (left) and in B16 cells infected with VSV 8 hours previously at an MOT 0.1 (right). Arrows indicate possible areas of cytoplasmic concentration of CSDE1 that were only observed in infected cells, which may represent cytoplasmic compartments associated with VSV synthesis.

Figure 14B:
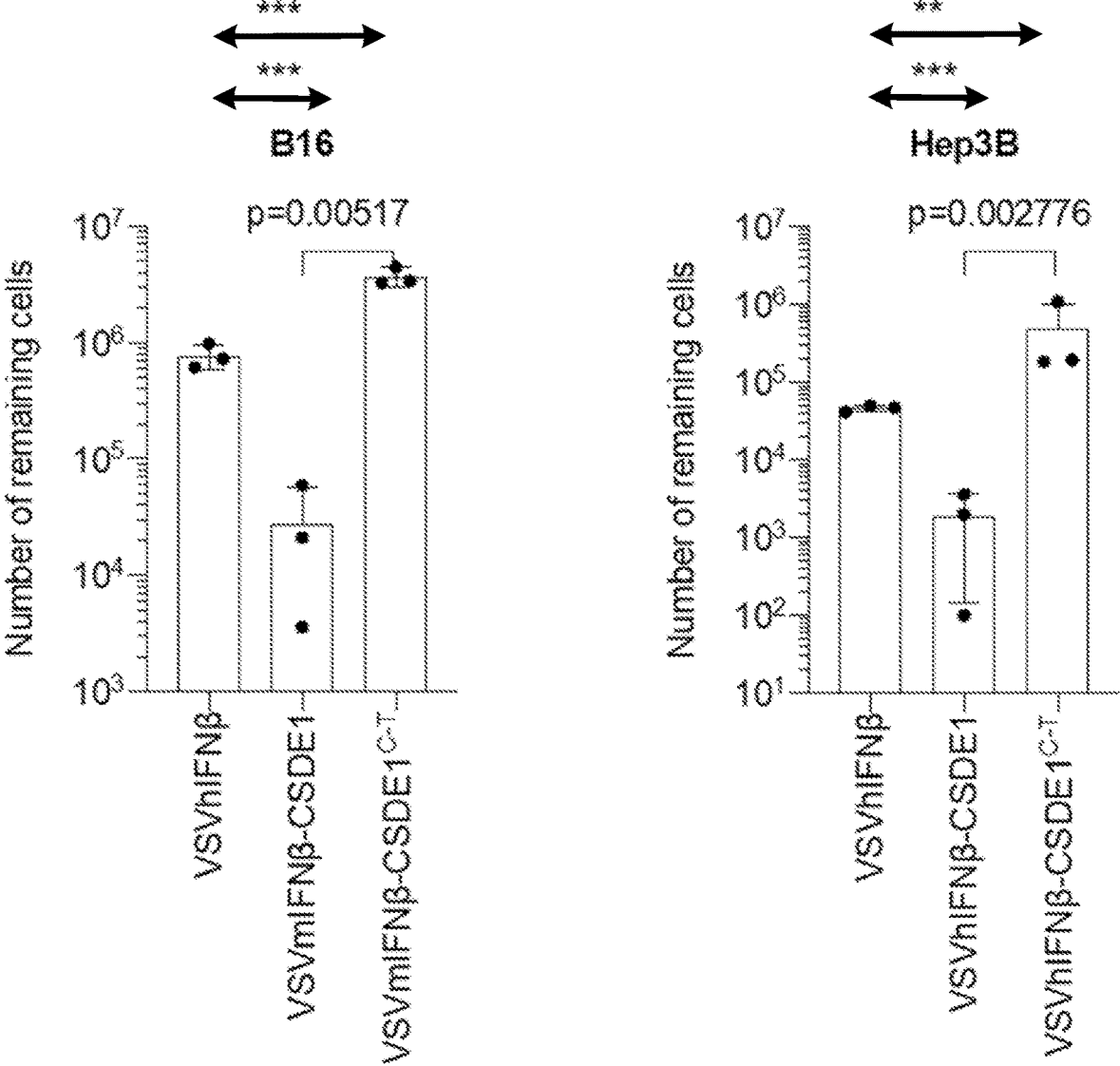

FIGS. 14A-14C. CSDE1 expressed from the virus enhances replication. (FIG. 14A) BHK, B16, Hep3B and Mel888 cell lines were infected with VSV-GFP, VSV-hIFNβ, VSV-CSDE1$^{WT}$ or VSV-CSDE1$^{P5S}$ (MOI 3) (triplicate wells). After 48 hours, virus was titered on BHK cells by plaque assay. *P≤0.05; P≤0.01; *P≤0.001. (FIG. 14B) B16 or Hep3B cells were infected (MOI 0.01) with VSV-IFNβ, VSV-IFNβ-CSDE1$^{WT}$, or VSV-IFNβ-CSDE1$^{P5S}$ (species matched IFNβ) for 21 days. Surviving cells were counted. (FIG. 14C) Hep3B cells were infected (MOI 0.01) with VSV-hIFNβ-CSDE1$^{WT}$ for 21 days. Sanger sequencing of CSDE1 from surviving cells is shown (2 independent experiments; mean±SD of 3 technical replicates). P-values were determined using a two way (FIG. 14A) or one-way (FIG. 14B) ANOVA with a Tukey multiple comparisons post-test (log transformed data). Statistical significance p<0.05, ns>0.05.

Figure 15A:
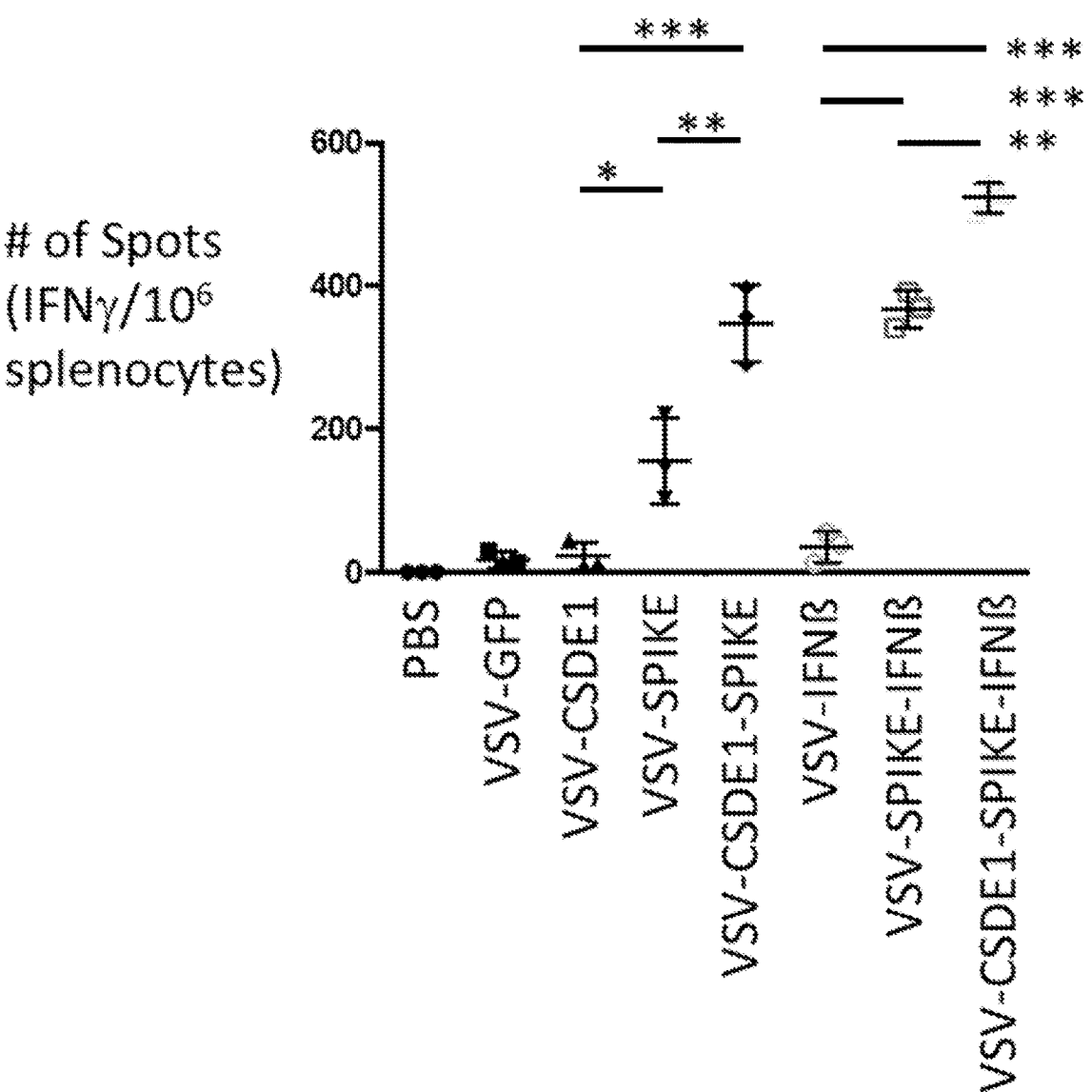
Figure 15B:
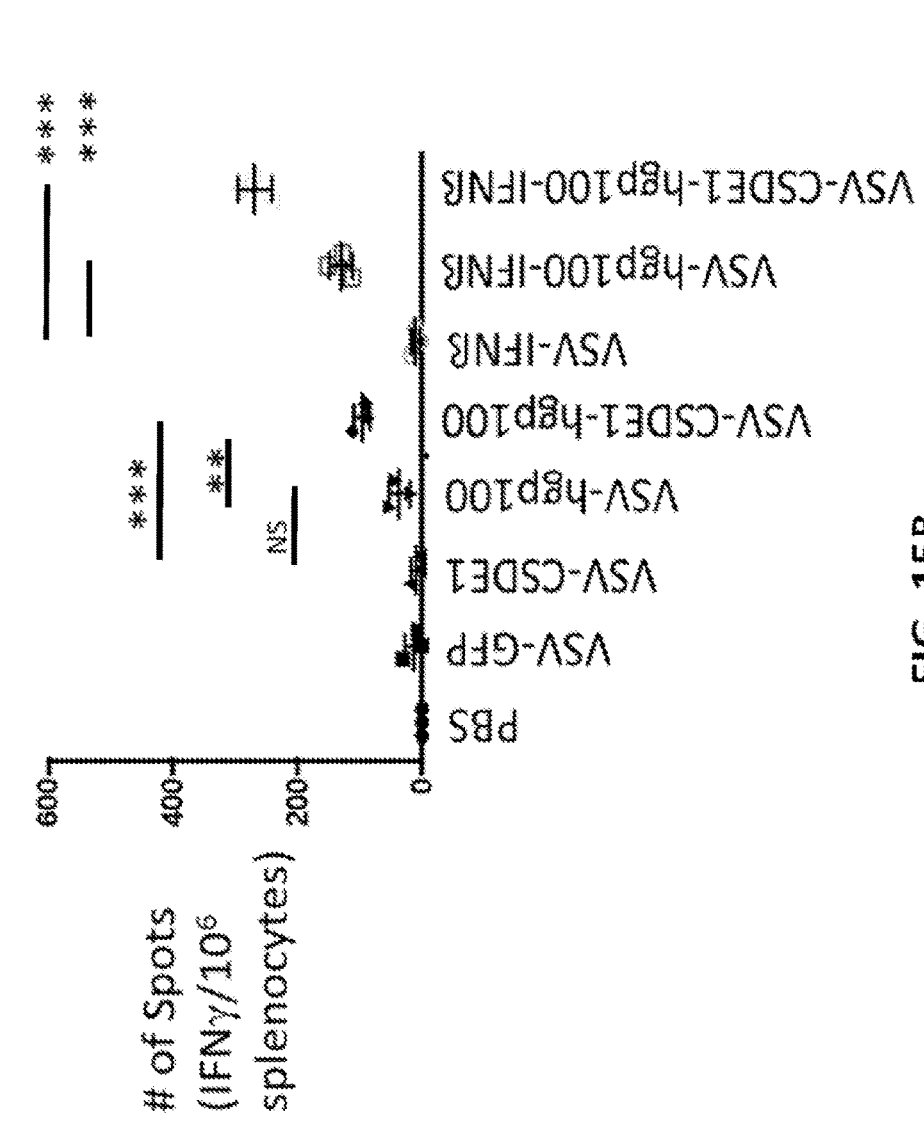

FIGS. 15A and 15B. CSDE1-expressing VSV generate higher frequency T cell responses. (FIG. 15A) ACEII transgenic mice were vaccinated (3 mice/group) with PBS, VSV-GFP, VSV-CSDE1, VSV-SPIKE, VSV-CSDE1-SPIKE, VSV-IFNβ, VSV-SPIKE-IFNβ, or VSV-CSDE1 (CSDE1 between the N and P genes; SPIKE between the M and G genes; IFNβ between the G and L genes) (10$^7$ pfu, IM). After 10 days, 10$^6$ splenocytes were re-stimulated in vitro in IFNγ ELISPOT wells with 10 μg total of 2 combined pools of peptides, consisting of 15-mer sequences with an 11 amino acid (aa) overlap, covering aa 689-895 (PEPTIVA-TOR® SARS-CoV-2 Prot_S+, Miltenyi) and the N-terminal S1 domain (PEPTIVATOR® SARS-CoV-2 Prot_S1, Miltenyi) of the Spike glycoprotein. The number of spots per well was plotted, using biological triplicates. (FIG. 15B) C57Bl/6 mice were vaccinated (3 mice/group) as described for FIG. 15A with vectors expressing the hgp100 cDNA (10$^7$ pfu, IM) and splenocytes were re-stimulated with the H-2Db-restricted human gp10025-33 (KVPRNQDWL hgp100 peptide). *P≤0.05; P≤0.01; *P≤0.001.

Figure 16:
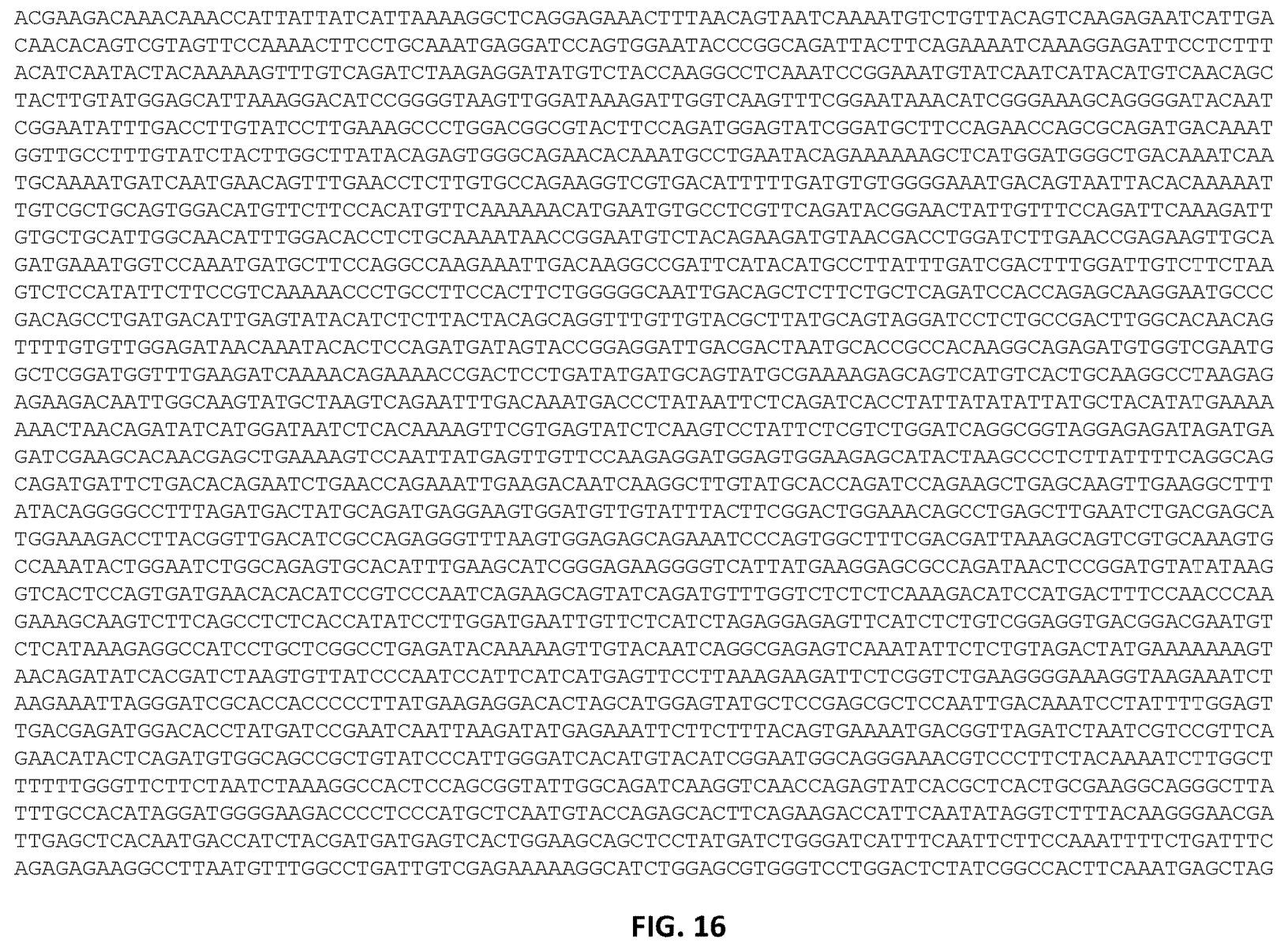
Figure 16:
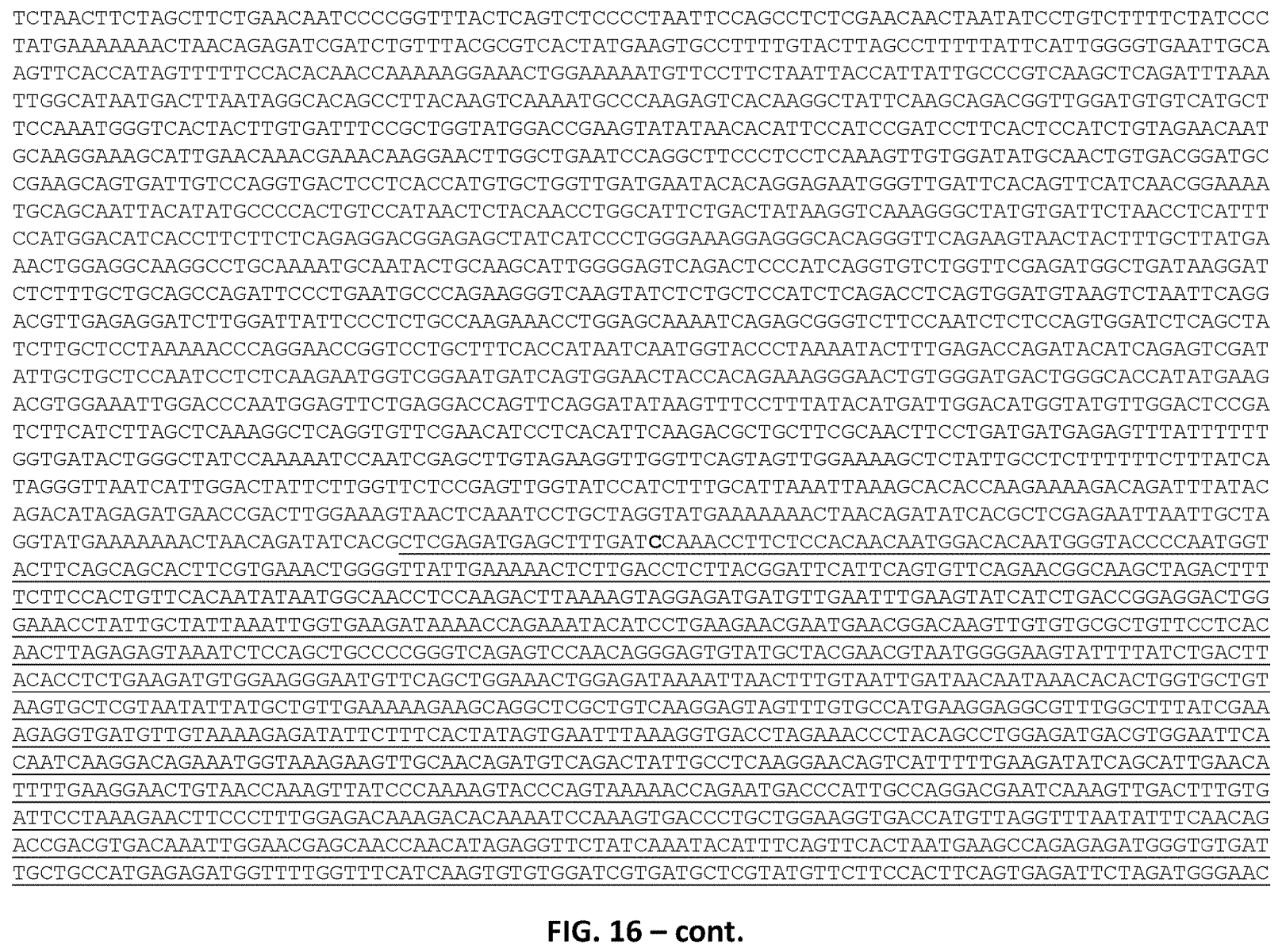
Figure 16:
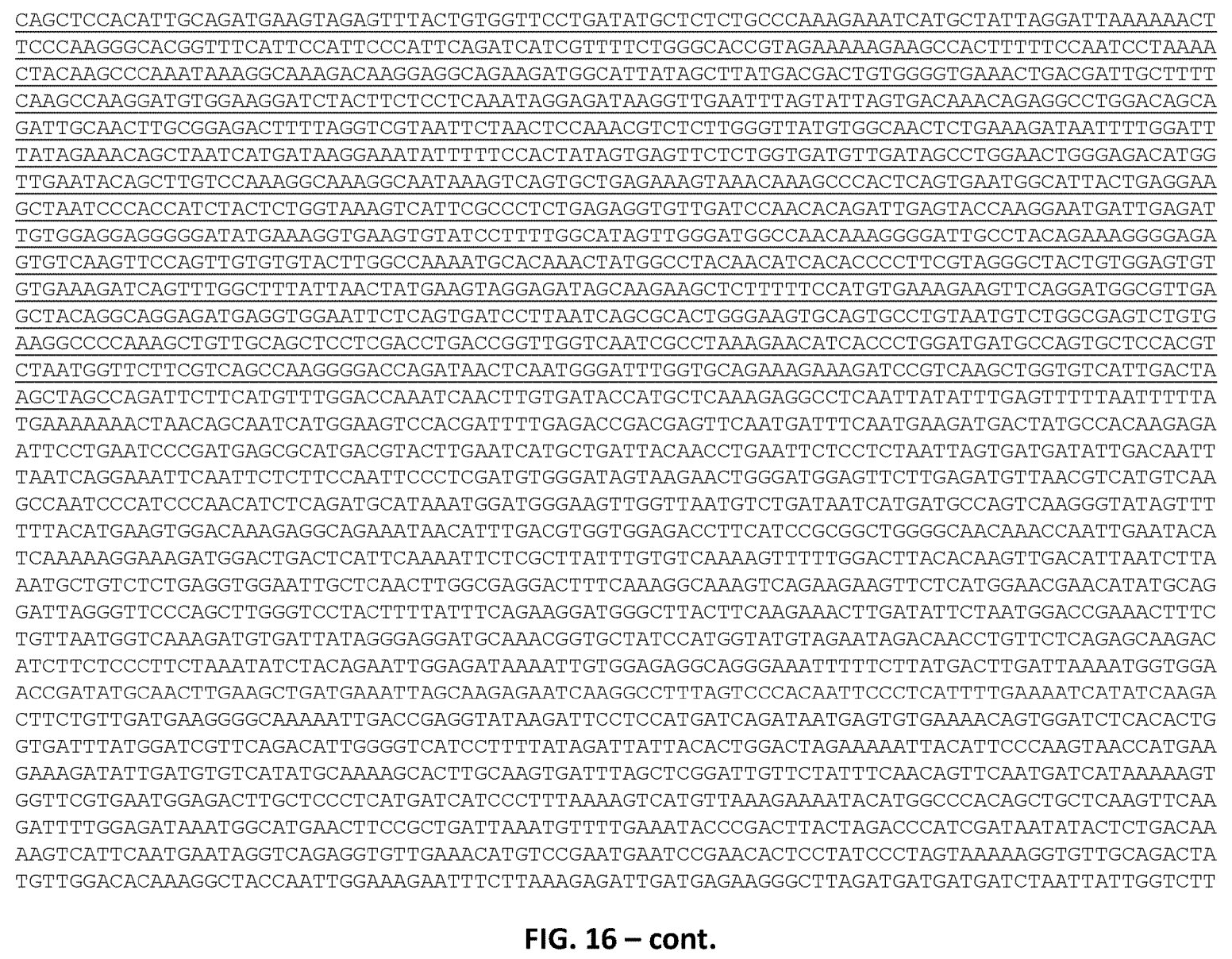
Figure 16:
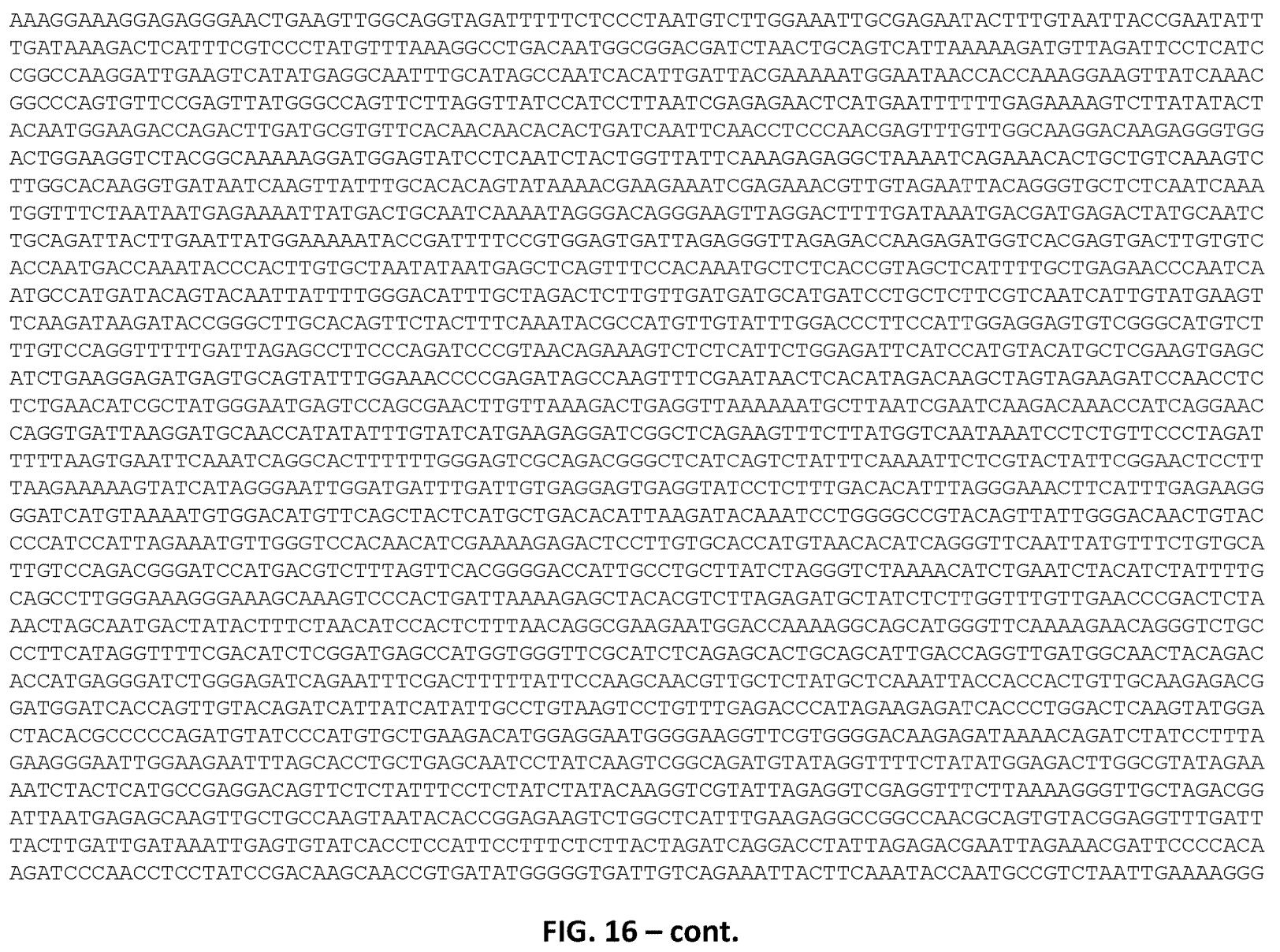

FIG. 16 is a nucleic acid sequence listing for a VSV-CSDE1$^{WT}$ construct (SEQ ID NO:16) containing the full VSV genome sequence; the underlined sequence encodes mouse CSDE1. The bolded C in the CSDE1 coding sequence is the position that can be mutated to a T in cancer cells escaping treatment.

DETAILED DESCRIPTION

This document provides methods and materials for treating cancer. For example, this document provides oncolytic viruses (e.g., replication-competent vesicular stomatitis viruses), nucleic acid molecules encoding a replication-competent oncolytic virus (e.g., replication-competent oncolytic vesicular stomatitis virus), methods for making replication-competent oncolytic viruses (e.g., replication-competent oncolytic vesicular stomatitis viruses), and methods for using replication-competent oncolytic viruses (e.g., replication-competent oncolytic vesicular stomatitis viruses) to treat cancer.

As described herein, a replication-competent oncolytic virus can be designed to deliver nucleic acid encoding a CSDE1 polypeptide (e.g., a wild-type or mutant version of a CSDE1 polypeptide (or a fragment thereof)) to cells (e.g., cancer cells and/or healthy cells within a tumor microenvironment) within a mammal. In some cases, expression of a wild-type version of a CSDE1 polypeptide (or a fragment thereof) can promote replication of an oncolytic virus. In some cases, expression of a mutant version of a CSDE1 polypeptide such as a CSDE1$^{P5S}$ polypeptide (or a fragment thereof that includes P5S) can promote an immune response against cancer cells within the mammal. Such immune responses can include T cell immune responses such as CTL immune responses that can kill cancer cells.

Any appropriate mammal having a cancer or having had cancer can be treated as described herein. Examples of mammals having a cancer or having had cancer that can be treated as described herein include, without limitation, humans, non-human primates (e.g., monkeys), dogs, cats, horses, cows, pigs, sheep, mice, and rats. In some cases, a human having a cancer or having had cancer can be treated as described herein.

When treating a mammal (e.g., a human) having a cancer or having had cancer as described herein, the cancer can be any type of cancer. In some cases, a cancer can be a blood cancer. In some cases, a cancer can include one or more solid tumors. Examples of cancers that can be treated as described herein include, without limitation, prostate cancers (e.g., prostate adenocarcinoma), breast cancers (e.g., breast invasive carcinomas and TNBCs), bladder cancers (e.g., bladder urothelial carcinomas), lung cancers (e.g., lung adenocarcinomas, lung squamous cell carcinomas, and mesotheliomas), liver cancers (e.g., liver hepatocellular carcinomas), cervical cancers (e.g., cervical squamous cell carcinomas and endocervical adenocarcinomas), bile duct cancers (e.g., cholangiocarcinomas), colon cancers (colon adenocarcinomas), rectal cancers (e.g., rectum adenocarcinomas), pancreatic cancers (e.g., pancreatic adenocarcinomas), uterine cancers (e.g., uterine corpus endometrial carcinomas and uterine carcinosarcomas), head and neck cancers (e.g., head and neck squamous cell carcinomas), testicular cancers (e.g., testicular germ cell tumors), ovarian cancers (e.g., ovarian serous cystadenocarcinoma), thyroid cancers (e.g., thyroid carcinomas), bone cancers (e.g., sarcomas), skin cancers (e.g., skin cutaneous melanoma), adrenal gland cancers (e.g., adrenocortical carcinomas, pheochromocytoma, and paraganglioma), kidney cancers (e.g., kidney renal clear cell carcinoma, kidney renal papillary cell carcinoma, and kidney chromophobes), lymphomas (e.g., lymphoid neoplasm diffuse large B-cell lymphoma), thymus cancers (e.g., thymoma), brain cancers (e.g., brain lower grade glioma and glioblastoma multiforme), leukemias (acute myeloid leukemia), and cancers of the eye (e.g., uveal melanoma).

In some cases, the methods described herein can include identifying a mammal (e.g., a human) as having a cancer. Any appropriate method can be used to identify a mammal as having a cancer. For example, imaging techniques and/or biopsy techniques can be used to identify mammals (e.g., humans) having cancer.

Once identified as having cancer or as having had cancer, the mammal can be administered a replication-competent oncolytic virus designed to deliver nucleic acid encoding a CSDE1 polypeptide (e.g., a wild-type or mutant version of a CSDE1 polypeptide, or a fragment thereof) to cells. Examples of replication-competent oncolytic viruses that can be designed to deliver nucleic acid encoding a CSDE1 polypeptide (e.g., a wild-type or mutant version of a CSDE1 polypeptide, or a fragment thereof) to cells include, without limitation, replication-competent oncolytic vesicular stomatitis viruses, replication-competent adenoviruses viruses, replication-competent herpes viruses, replication-competent pox viruses, replication-competent retroviruses, replication-competent lentiviruses, replication-competent measles viruses, and replication-competent polioviruses.

As described herein, a replication-competent vesicular stomatitis virus can be designed to have a nucleic acid molecule that encodes a VSV N polypeptide, a VSV P polypeptide, a VSV M polypeptide, an optional interferon-β polypeptide (e.g., a human interferon-β polypeptide), a VSV G polypeptide, a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue), and a VSV L polypeptide. It will be appreciated that the sequences described herein with respect to a vesicular stomatitis virus are incorporated into a plasmid coding for the positive sense cDNA of the viral genome allowing generation of the negative sense genome of vesicular stomatitis viruses. Thus, it will be appreciated that a nucleic acid sequence that encodes a VSV polypeptide, for example, can refer to an RNA sequence that is the template for the positive sense transcript that encodes (e.g., via direct translation) that polypeptide.

In some cases, a replication-competent vesicular stomatitis virus can be designed to have a nucleic acid molecule that encodes a VSV N polypeptide, a VSV P polypeptide, a VSV M polypeptide, an interferon-β polypeptide (e.g., a human interferon-β polypeptide), a VSV G polypeptide, a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue), and a VSV L polypeptide. In some cases, a vesicular stomatitis virus provided herein can be designed to have a nucleic acid molecule that encodes a VSV N polypeptide, a VSV P polypeptide, a VSV M polypeptide, an interferon-β polypeptide (e.g., a human interferon-β polypeptide), a VSV G polypeptide, a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue), and a VSV L polypeptide with the nucleic acid sequence encoding the interferon-β polypeptide being located between the sequences encoding the VSV M polypeptide and the VSV G polypeptide and with the nucleic acid sequence encoding the CSDE1 polypeptide being located between the sequences encoding the VSV G polypeptide and the VSV L polypeptide.

The nucleic acid encoding a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue) can be positioned at any location within the VSV genome. In some cases, the nucleic acid encoding a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue) can be positioned downstream of the nucleic acid encoding the VSV M polypeptide. For example, nucleic acid encoding a CSDE1 polypeptide (e.g., a wild-type or mutant version of a CSDE1 polypeptide) or a fragment thereof (e.g., a fragment of a full length wild-type CSDE1 polypeptide, or a fragment of a full length CSDE1 polypeptide that includes a P5S residue) can be positioned between nucleic acid encoding a VSV M polypeptide and nucleic acid encoding a VSV G polypeptide or between nucleic acid encoding a VSV G polypeptide and nucleic acid encoding a VSV L polypeptide.

In some cases, a vesicular stomatitis virus provided herein can have a nucleic acid molecule that includes a sequence encoding an interferon (IFN) polypeptide (e.g., a human IFN-β polypeptide), a sodium iodide symporter (NIS) polypeptide (e.g., a human NIS polypeptide), a fluorescent polypeptide (e.g., a GFP polypeptide), any appropriate therapeutic transgene (e.g., HSV-TK or cytosine deaminase), a polypeptide that antagonizes host immunity (e.g., influenza NS1, HSVγ34.5, or SOCS1), or a tumor antigen (e.g., cancer vaccine components). The nucleic acid encoding the IFN polypeptide can be positioned between the nucleic acid encoding the VSV M polypeptide and the nucleic acid encoding the VSV G polypeptide. Such a position can allow the viruses to express an amount of the IFN polypeptide that is effective to activate anti-viral innate immune responses in non-cancerous tissues, and thus alleviate potential viral toxicity, without impeding efficient viral replication in cancer cells. The nucleic acid encoding the NIS polypeptide can be positioned between the nucleic acid encoding the VSV M polypeptide and the VSV G polypeptide. Such a position of can allow the viruses to express an amount of the NIS polypeptide that (a) is effective to allow selective accumulation of iodide in infected cells, thereby allowing both imaging of viral distribution using radioisotopes and radiotherapy targeted to infected cancer cells, and (b) is not so high as to be toxic to infected cells. Positioning the nucleic acid encoding an IFN polypeptide between the nucleic acid encoding the VSV M polypeptide and the nucleic acid encoding the VSV G polypeptide and positioning the nucleic acid encoding a NIS polypeptide between the nucleic acid encoding the VSV M polypeptide and the nucleic acid encoding the VSV G polypeptide within the genome of a vesicular stomatitis virus can result in vesicular stomatitis viruses that are viable, that have the ability to replicate and spread, that express appropriate levels of functional IFN polypeptides, and that express appropriate levels of functional NIS polypeptides to take up radio-iodine for both imaging and radio-virotherapy.

Any appropriate nucleic acid encoding a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue) can be inserted into the genome of an oncolytic virus such as a vesicular stomatitis virus. For example, nucleic acid encoding a wild-type human CSDE1 polypeptide can be inserted into the genome of an oncolytic virus such as a vesicular stomatitis virus. Examples of nucleic acid encoding CSDE1 polypeptides that can be inserted into the genome of an oncolytic virus such as a vesicular stomatitis virus include, without limitation, nucleic acid encoding a CSDE1 polypeptide set forth in GENBANK® Accession No. NM_007158.6, nucleic acid encoding a CSDE1 polypeptide having the amino acid sequence set forth in FIG. 7 (SEQ ID NO:2), the nucleic acid as set forth in FIG. 8 (SEQ ID NO:3), nucleic acid encoding a CSDE1 polypeptide set forth in GENBANK® Accession No. NM_007158.6 provided that position 5 contains a serine instead of a proline, nucleic acid encoding a CSDE1 polypeptide having the amino acid sequence set forth in FIG. 7 provided that position 5 contains a serine instead of a proline, and the nucleic acid as set forth in FIG. 8 provided that position 13 contains a T instead of a C. In some cases, the CSDE1 amino acid sequence of a CSDE1 fragment can be amino acid residues 1 to 100, 1 to 75, 1-50, 1-25, 1-13, 1-12, 1-11, 1-10, 1-9, 1-8, 2-100, 2-75, 2-50, 2-25, 2-14, 2-13, 2-12, 2-11, 2-10, 2-9, 3-100, 3-75, 3-50, 3-25, 3-15, 3-14, 3-13, 3-12, 3-11, 3-10, 4-100, 4-75, 4-50, 4-25, 4-16, 4-15, 4-14, 4-13, 4-12, 4-11, 5-100, 5-75, 5-50, 5-25, 5-17, 5-16, 5-15, 5-14, 5-13, or 5-12 of a CSDE1 polypeptide provided that position 5 is a serine instead of a proline. In some cases, the CSDE1 amino acid sequence of a CSDE1 fragment can be at least 700, at least 725, at least 750, or at least 760 amino acids in length. For example, a CSDE1 fragment can have an amino acid sequence with at least 700 (e.g., at least 725, at least 750, or at least 760) consecutive amino acids from SEQ ID NO:2. In some cases, a CSDE1 fragment can lack from 1 to 5 (e.g., 1, 2, 3, 4, or 5) consecutive amino acid residues as compared to SEQ ID NO:2. For example, a CSDE1 fragment can have the sequence of SEQ ID NO:2, except that the fragment lacks from 1 to 5 (e.g., 1, 2, 3, 4, or 5) amino acid residues at the N-terminus of SEQ ID NO:2, or lacks from 1 to 5 (e.g., 1, 2, 3, 4, or 5) amino acid residues at the C-terminus of SEQ ID NO:2.

Any appropriate nucleic acid encoding an IFN polypeptide can be inserted into the genome of an oncolytic virus such as a vesicular stomatitis virus provided herein. For example, nucleic acid encoding an IFN beta polypeptide can be inserted into the genome of a vesicular stomatitis virus. Examples of nucleic acid encoding IFN beta polypeptides that can be inserted into the genome of an oncolytic virus such as a vesicular stomatitis virus include, without limitation, nucleic acid encoding a human IFN beta polypeptide of the nucleic acid sequence set forth in GENBANK® Accession No. NM_002176.2 (GI No. 50593016), nucleic acid encoding a mouse IFN beta polypeptide of the nucleic acid sequence set forth in GENBANK® Accession No. NM_010510.1 (GI No. 6754303), BC119395.1 (GI No. 111601321), or BC119397.1 (GI No. 111601034), and nucleic acid encoding a rat IFN beta polypeptide of the nucleic acid sequence set forth in GENBANK® Accession No. NM_019127.1 (GI No. 9506800).

Any appropriate nucleic acid encoding a NIS polypeptide can be inserted into the genome of an oncolytic virus such as a vesicular stomatitis virus. For example, nucleic acid encoding a human NIS polypeptide can be inserted into the genome of a vesicular stomatitis virus. Examples of nucleic acid encoding NIS polypeptides that can be inserted into the genome of an oncolytic virus such as a vesicular stomatitis virus include, without limitation, nucleic acid encoding a human NIS polypeptide of the nucleic acid sequence set forth in GENBANK® Accession No. NM_000453.2 (GI No.164663746), BC105049.1 (GI No. 85397913), or BC105047.1 (GI No. 85397519), nucleic acid encoding a mouse NIS polypeptide of the nucleic acid sequence set forth in GENBANK® Accession No. NM_053248.2 (GI No. 162138896), AF380353.1 (GI No. 14290144), or AF235001.1 (GI No. 12642413), nucleic acid encoding a chimpanzee NIS polypeptide of the nucleic acid sequence set forth in GENBANK® Accession No. XM_524154 (GI No. 114676080), nucleic acid encoding a dog NIS polypeptide of the nucleic acid sequence set forth in GENBANK® Accession No. XM_541946 (GI No. 73986161), nucleic acid encoding a cow NIS polypeptide of the nucleic acid sequence set forth in GENBANK® Accession No. XM_581578 (GI No. 297466916), nucleic acid encoding a pig NIS polypeptide of the nucleic acid sequence set forth in GENBANK® Accession No. NM_214410 (GI No. 47523871), and nucleic acid encoding a rat NIS polypeptide of the nucleic acid sequence set forth in GENBANK® Accession No. NM_052983 (GI No. 158138504).

In some cases, a replication-competent virus (e.g., a vesicular stomatitis virus) can be designed to have a nucleic acid molecule that encodes (or is a template for a nucleic acid that encodes) a VSV N polypeptide, a VSV P polypeptide, a VSV M polypeptide, an interferon-β polypeptide (e.g., a human interferon-β polypeptide), a VSV G polypeptide, a CSDE1 polypeptide (e.g., a wild-type CSDE1 polypeptide or a fragment thereof), an antigen (e.g., an antigen from an infectious agent, such as a SARS-CoV-2 antigen), and a VSV L polypeptide. In some cases, a virus (e.g., a vesicular stomatitis virus) provided herein can be designed to have a nucleic acid molecule that encodes a VSV N polypeptide, a VSV P polypeptide, a VSV M polypeptide, an interferon-β polypeptide (e.g., a human interferon-β polypeptide), a VSV G polypeptide, a CSDE1 polypeptide (e.g., a wild-type CSDE1 polypeptide or a fragment thereof), an antigen (e.g., a virus antigen), and a VSV L polypeptide, with the nucleic acid sequence encoding the CSDE1 polypeptide and the nucleic acid encoding the antigen being located between the sequences encoding the VSV N polypeptide and the VSV L polypeptide. Such viruses can be used, for example, to induce an immune response in a mammal, and are referred to as "immunogenic" viruses.

The nucleic acid encoding a CSDE1 polypeptide (e.g., a wild-type CSDE1 polypeptide or a fragment thereof), the nucleic acid encoding an interferon-β polypeptide (e.g., human interferon-β), and the nucleic acid encoding the antigen can be positioned at any location within the virus (e.g., VSV) genome. In some cases, the nucleic acid encoding a CSDE1 polypeptide (e.g., a wild-type CSDE1 polypeptide or a fragment thereof can be positioned downstream of the nucleic acid encoding the VSV N polypeptide. In some cases, for example, nucleic acid encoding a CSDE1 polypeptide (e.g., a wild-type CSDE1 polypeptide or a fragment thereof) can be positioned between nucleic acid encoding a VSV N polypeptide and nucleic acid encoding a VSV P polypeptide, nucleic acid encoding an antigen (e.g., a virus antigen) can be positioned between nucleic acid encoding a VSV M polypeptide and nucleic acid encoding a VSV G polypeptide, and nucleic acid encoding an interferon-β polypeptide (e.g., a human interferon-β polypeptide) can be positioned between nucleic acid encoding a VSV G polypeptide and nucleic acid encoding a VSV L polypeptide.

Any appropriate antigen can be encoded by a nucleic acid or virus provided herein. In some cases, for example, an antigen can be from an infectious agent, such as a virus (e.g., a SARS-CoV-2 virus, an influenza virus, an EBOLA virus, a yellow fever virus, a dengue virus, a coronavirus, a measles virus, a mumps virus, or a rubella virus) or a bacteria (e.g., an *Escherichia* species, a *Salmonella* species, a *Mycobacterium* species, a *Clostridium* species, a *Bacillus* species, or a *Leptospira* species). Examples of antigens include, without limitation, the spike protein of SARS-CoV-2, the M protein of SARS-CoV-2, the N protein of SARS-CoV-2, the NP protein of influenza, the M1 protein of influenza, the NS1 protein of influenza, the NP protein of Ebola, the GP protein of Ebola, the VP35 protein of Ebola, the VP40 protein of Ebola, the NS1 protein of yellow fever, the NS1 protein of dengue virus, the spike protein of a coronavirus, the M protein of a coronavirus, the N protein of a coronavirus, the F protein from measles virus, the H protein from measles virus, a nucleocapsid protein from mumps, the E1 spike protein from rubella virus, the E2 spike protein from rubella virus, the C protein of rubella virus, the O antigen of *Escherichia coli*, glfT2 of *Mycobacterium tuberculosis*, fas of *Mycobacterium tuberculosis*, iniB of *Mycobacterium tuberculosis*, tetanus toxoid from *Clostridium tatanis*, anthrax toxin from *Bacillus anthracis*, LipL21 from *Leptospira* species, LipL41 from *Leptospira* species, LipL32 from *Leptospira* species, and fragments of any of these proteins.

The nucleic acid sequences of a vesicular stomatitis virus provided herein that encode a VSV N polypeptide, a VSV P polypeptide, a VSV M polypeptide, a VSV G polypeptide, and a VSV L polypeptide can be from a VSV Indiana strain as set forth in GENBANK® Accession No. NC_001560 (GI No. 9627229) or can be from a VSV New Jersey strain.

In one aspect, this document provides vesicular stomatitis viruses containing a nucleic acid molecule (e.g., an RNA molecule) having (e.g., in a 3' to 5' direction) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), and a nucleic acid sequence that is a template for a positive sense transcript encoding a VSV L polypeptide. Such vesicular stomatitis viruses can infect cells (e.g., cancer cells) and be replication-competent.

Any appropriate method can be used to insert nucleic acid (e.g., nucleic acid encoding a CSDE1 polypeptide such as a wild-type version or mutant version of a CSDE1 polypeptide or a fragment thereof such as a fragment of a full length wild-type CSDE1 polypeptide, or a fragment of a full length CSDE1 polypeptide that includes a P5S residue, nucleic acid encoding an IFN polypeptide, and/or nucleic acid encoding a NIS polypeptide) into the genome of an oncolytic virus such as a vesicular stomatitis virus. For example, methods described elsewhere (e.g., in Schnell et. al., *PNAS*, 93:11359-11365 (1996); Obuchi et al., *J. Virol.*, 77(16): 8843-56 (2003)); Goel et al., *Blood*, 110(7):2342-50 (2007)); and Kelly et al., *J. Virol.*, 84(3):1550-62 (2010)) can be used to insert nucleic acid into the genome of a vesicular stomatitis virus. Any appropriate method can be used to identify oncolytic viruses such as vesicular stomatitis viruses containing a nucleic acid molecule described herein. Such methods include, without limitation, PCR and nucleic acid hybridization techniques such as Northern and Southern analysis. In some cases, immunohistochemistry and biochemical techniques can be used to determine if an oncolytic virus (e.g., a vesicular stomatitis virus) contains a particular nucleic acid molecule by detecting the expression of a polypeptide encoded by that particular nucleic acid molecule.

In another aspect, this document provides nucleic acid molecules that encode a VSV N polypeptide, a VSV P polypeptide, a VSV M polypeptide, a VSV G polypeptide, a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), and a VSV L polypeptide. For example, a nucleic acid molecule provided herein can be a single nucleic acid molecule that includes a nucleic acid sequence that encodes a VSV N polypeptide, a nucleic acid sequence that encodes a VSV P polypeptide, a nucleic acid sequence that encodes a VSV M polypeptide, a nucleic acid sequence that encodes a VSV G polypeptide, a nucleic acid sequence that encodes a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), and a nucleic acid sequence that encodes a VSV L polypeptide. As another example, a nucleic acid molecule provided herein can be a single nucleic acid molecule that includes a nucleic acid sequence that encodes a VSV N polypeptide, a nucleic acid sequence that encodes a VSV P polypeptide, a nucleic acid sequence that encodes a VSV M polypeptide, a nucleic acid sequence that encodes an IFN-β polypeptide, a nucleic acid sequence that encodes a VSV G polypeptide, a nucleic acid sequence that encodes a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), and a nucleic acid sequence that encodes a VSV L polypeptide.

The term "nucleic acid" as used herein encompasses both RNA (e.g., viral RNA) and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

This document also provides method for treating cancer (e.g., to reduce tumor size, inhibit tumor growth, reduce the number of viable tumor cells, or reduce the number of cancer cells escaping an initial cancer treatment) and methods for inducing host immunity against cancer. For example, an oncolytic virus provided herein such as a vesicular stomatitis virus provided herein can be administered to a mammal having cancer to reduce tumor size, to inhibit cancer cell or tumor growth, to reduce the number of viable cancer cells within the mammal, and/or to induce host immunogenic responses against a tumor. An oncolytic virus provided herein such as a vesicular stomatitis virus provided herein can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). In some cases, an oncolytic virus provided herein such as a vesicular stomatitis virus provided herein can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., Vero cells) in culture.

An oncolytic virus provided herein such as a vesicular stomatitis virus provided herein can be administered to a cancer patient by, for example, direct injection into a group of cancer cells (e.g., a tumor), direct injection into a tumor microenvironment, or intravenous delivery to cancer cells. An oncolytic virus provided herein such as a vesicular stomatitis virus provided herein can be used to treat different types of cancer including, without limitation, myeloma (e.g., multiple myeloma), melanoma, glioma, lymphoma, mesothelioma, and cancers of the lung, brain, stomach, colon, rectum, kidney, prostate, ovary, breast, pancreas, liver, and head and neck.

An oncolytic virus provided herein such as a vesicular stomatitis virus provided herein can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

An oncolytic virus provided herein such as a vesicular stomatitis virus provided herein can be delivered in a dose ranging from, for example, about $10^3$ pfu to about $10^{12}$ pfu (e.g., about $10^5$ pfu to about $10^{12}$ pfu, about $10^5$ pfu to about $10^{11}$ pfu, about $10^6$ pfu to about $10^{11}$ pfu, or about $10^6$ pfu to about $10^{10}$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses can be administered by the same route as initially used or by another route. A therapeutically effective dose can be delivered in several discrete doses (e.g., days or weeks apart) and in one embodiment, one to about twelve doses are provided. Alternatively, a therapeutically effective dose of an oncolytic virus provided herein such as a vesicular stomatitis virus provided herein can be delivered by a sustained release formulation. In some cases, an oncolytic virus provided herein such as a vesicular stomatitis virus provided herein can be delivered in combination with pharmacological agents that facilitate viral replication and spread within cancer cells or agents that protect non-cancer cells from viral toxicity. Examples of such agents are described elsewhere (Alvarez-Breckenridge et al., *Chem. Rev.*, 109(7):3125-40 (2009)).

An oncolytic virus provided herein such as a vesicular stomatitis virus provided herein can be administered using a device for providing sustained release. A formulation for sustained release of viruses can include, for example, a polymeric excipient (e.g., a swellable or non-swellable gel, or collagen). A therapeutically effective dose of an oncolytic virus provided herein such as a vesicular stomatitis virus provided herein can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. Alternatively, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

An oncolytic virus provided herein such as a vesicular stomatitis virus provided herein can be directly administered. For example, a virus can be injected directly into a tumor (e.g., a breast cancer tumor) that is palpable through the skin. Ultrasound guidance also can be used in such a method. Alternatively, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of an oncolytic virus provided herein such as a vesicular stomatitis virus provided herein can be directly administered to a group of cancer cells that is visible in an exposed surgical field.

In some cases, an oncolytic virus provided herein such as a vesicular stomatitis virus provided herein can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of therapy with an oncolytic virus provided herein such as a vesicular stomatitis virus provided herein can be monitored by evaluating changes in clinical symptoms or by direct monitoring of the number of cancer cells or size of a tumor. For a solid tumor, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

In some cases, a mammal having cancer or having had cancer can be treated using a combination of two or more of a chemotherapeutic agent, an oncolytic virus, and a checkpoint inhibitor. For example, a mammal (e.g., a human) having cancer can be treated by administering (a) one or more chemotherapeutic agents, (b) one or more replication-competent oncolytic viruses provided herein, and (c) one or more checkpoint inhibitors. In some cases, a mammal (e.g., a human) having cancer can be treated by administering (a) one or more chemotherapeutic agents and (b) one or more replication-competent oncolytic viruses provided herein. In some cases, a mammal (e.g., a human) having cancer can be treated by administering (a) one or more replication-competent oncolytic viruses provided herein and (b) one or more checkpoint inhibitors. Examples of chemotherapeutic agents that can be used in such combinations include, without limitation, gemcitabine, cyclophosphamide, tamoxifen, and temozolomide. Examples of checkpoint inhibitor that can be used in such combinations include, without limitation, anti-PD1 antibodies, anti-PD-L1 antibodies, anti-CTLA-4 antibodies, anti-TIM3 antibodies, and anti-Lag3 antibodies.

As described herein, cancer cells can escape treatments directed against the cancer cells (e.g., oncolytic therapies) by promoting mutagenesis of their genomes. In some cases, a mutation of a CSDE1 nucleic acid can result in cancer cell escape. To target killing those cancer cells attempting to escape treatment, an oncolytic virus designed to express a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue) can be administered to the mammal (e.g., a human) to promote immune responses (e.g., T cell immune responses) against the escaping cancer cells as described herein. In some cases, (a) cells such as dendritic cells designed to express a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), (b) a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), (c) nucleic acid encoding a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue), or (d) a combination thereof can be administered in addition to or instead of administering an oncolytic virus designed to express a CSDE1 polypeptide (e.g., a wild-type version or mutant version of a CSDE1 polypeptide) or a fragment thereof (e.g., a fragment of a full length wild-type CSDE1 polypeptide, or a fragment of a full length CSDE1 polypeptide that includes a P5S residue) to promote immune responses (e.g., T cell immune responses such as CTL immune responses) against the escaping cancer cells.

This document also provides cancer neoantigens (e.g., a CSDE1$^{P5S}$ polypeptide or fragment thereof that includes P5S), nucleic acids encoding a cancer neoantigen (e.g., a CSDE1$^{P5S}$ polypeptide or fragment thereof that includes P5S), and methods for stimulating immune cells (e.g., cytotoxic T lymphocytes) to kill cancer cells by administering a cancer neoantigen and/or nucleic acids encoding a cancer neoantigen to a mammal. For example, this document provides full length CSDE1 polypeptides that include a P5S amino acid substitution or a fragment thereof (e.g., a fragment of a full length CSDE1 polypeptide provided that the fragment includes the P5S residue). In some cases, the CSDE1 amino acid sequence of such a fragment can be amino acid residues 1 to 100, 1 to 75, 1-50, 1-25, 1-13, 1-12, 1-11, 1-10, 1-9, or 1-8 of a CSDE1 polypeptide provided that position 5 is a serine. In some cases, a full length CSDE1 polypeptide that include a P5S amino acid substitution or a fragment thereof (e.g., a fragment of a full length CSDE1 polypeptide provided that the fragment includes the P5S residue) provided herein can include a cell penetrating amino acid sequence. Examples of cell penetrating sequences that can be contiguous with a full length CSDE1 polypeptide that include a P5S amino acid substitution or a fragment thereof (e.g., a fragment of a full length CSDE1 polypeptide provided that the fragment includes the P5S residue) include, without limitation, those cell penetrating amino acid sequences set forth in Table 1.

TABLE 1

| Cell penetrating amino acid sequences. | |
| --- | --- |
| Sequence | SEQ ID NO: |
| GRKKRRQRRRPPQ | 4 |
| RQIKIWFQNRRMKWKK | 5 |
| LLIILRRRIRKQAHAHSK | 6 |

This document also provides method for inducing host immunity against an antigen. For example, an immunogenic virus provided herein such as a vesicular stomatitis virus provided herein can be administered to a mammal to induce a host immunogenic response an antigen (e.g., an antigen contained in the virus or encoded by nucleic acid in the virus). An immunogenic virus provided herein such as a vesicular stomatitis virus provided herein can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). In some cases, an immunogenic virus provided herein such as a vesicular stomatitis virus provided herein can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., Vero cells) in culture.

An immunogenic virus provided herein such as a vesicular stomatitis virus provided herein can be administered to a mammal by, for example, injection (e.g., intramuscular, intravenous, or subcutaneous injection). An immunogenic virus provided herein such as a vesicular stomatitis virus provided herein can be used to treat, prevent, or reduce the likelihood of infection by different types of infectious agents, such as viruses (e.g., a SARS-CoV-2 virus, an influenza virus, an EBOLA virus, a yellow fever virus, a dengue virus, a coronavirus, a measles virus, a mumps virus, or a rubella virus) and bacteria (e.g., an *Escherichia* species, a *Salmonella* species, a *Mycobacterium* species, a *Clostridium* species, a *Bacillus* species, or a *Leptospira* species).

An immunogenic virus provided herein such as a vesicular stomatitis virus provided herein can be administered to a patient in a biologically compatible solution or a pharmaceutically acceptable delivery vehicle, by administration either directly into a particular tissue (e.g., intramuscularly) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient, an effective dose can be determined by setting as a lower limit the concentration of virus proven to be safe and escalating to higher doses of up to $10^{12}$ pfu, while monitoring for an immune response along with the presence of any deleterious side effects. A therapeutically effective dose typically provides an immune response resulting in antibodies against the antigen. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

An immunogenic virus provided herein such as a vesicular stomatitis virus provided herein can be delivered in a dose ranging from, for example, about $10^3$ pfu to about $10^{12}$ pfu (e.g., about $10^5$ pfu to about $10^{12}$ pfu, about $10^5$ pfu to about $10^{11}$ pfu, about $10^6$ pfu to about $10^{11}$ pfu, or about $10^6$ pfu to about $10^{10}$ pfu). A therapeutically effective dose can be provided in repeated doses. Repeat dosing is appropriate in cases in which observations indicate either that an immune response has not been achieved, or that the degree of immune response has not reached a desired level. Repeat doses can be administered by the same route as initially used or by another route. A therapeutically effective dose can be delivered in several discrete doses (e.g., days or weeks apart) and in one embodiment, one to about twelve doses are provided. Alternatively, a therapeutically effective dose of an of an immune response virus provided herein such as a vesicular stomatitis virus provided herein can be delivered by a sustained release formulation. In some cases, an of an immune response virus provided herein such as a vesicular stomatitis virus provided herein can be delivered in combination with pharmacological agents that facilitate viral replication and spread, or agents that protect cells from viral toxicity. Examples of such agents are described elsewhere (Alvarez-Breckenridge et al., *Chem. Rev.,* 109(7):3125-40 (2009)).

The course of therapy with an immunogenic virus provided herein such as a vesicular stomatitis virus provided herein can be monitored by evaluating changes in clinical symptoms of a mammal having a bacterial or viral infection, or by direct monitoring of the number antibodies against the antigen that are detected in a biological sample from the mammal. The effectiveness of viral treatment also can be assessed by monitoring the levels of a bacteria or virus specific antigen after immunization. Bacteria and virus antigens include, for example, the spike protein of SARS-CoV-2, the M protein of SARS-CoV-2, the N protein of SARS-CoV-2, the NP protein of influenza, the M1 protein of influenza, the NS1 protein of influenza, the NP protein of Ebola, the GP protein of Ebola, the VP35 protein of Ebola, the VP40 protein of Ebola, the NS1 protein of yellow fever, the NS1 protein of dengue virus, the spike protein of a coronavirus, the M protein of a coronavirus, the N protein of a coronavirus, the F protein from measles virus, the H protein from measles virus, a nucleocapsid protein from mumps, the E1 spike protein from rubella virus, the E2 spike protein from rubella virus, the C protein of rubella virus, the O antigen of *Escherichia coli, glfT*2 of *Mycobacterium tuberculosis*, fas of *Mycobacterium tuberculosis*, iniB of *Mycobacterium tuberculosis*, tetanus toxoid from *Clostridium tatanis*, anthrax toxin from *Bacillus anthracis*, LipL21 from *Leptospira* species, LipL41 from *Leptospira* species, LipL32 from *Leptospira* species, and fragments of any of these proteins.

The invention will be further described in the following examples, which do not limit the scope of the invention described in the claims.

EXAMPLES

Example 1—Cancer Immunotherapy Against Treatment-Driven Neo-Antigenesis

Experimental Design

These experiments were designed to evaluate how reproducible mutations induced in tumor cells escaping oncolytic virotherapy could be exploited for the design of immunotherapies targeting treatment escape. 7-10 mice per group were used for each survival experiment to achieve statistical power to make multiple comparisons. Animals were randomized to treatment groups following tumor implantation using the GraphPad QuickCalcs online tool (graphpad.com/quickcalcs/randMenu/).

Cell Lines and Viruses

B16 murine melanoma, and human Hep3B hepatocellular carcinoma and BHK cells were originally obtained from the ATCC. Human Mel888 melanoma cells were obtained from the Imperial Cancer Research Fund (ICRF) in 1997/1998 and were grown in DMEM (Hyclone, Logan, UT, USA)+ 10% FBS (Life Technologies). Cell lines were authenticated by morphology, growth characteristics, PCR for tissue specific gene expression (gp100, TYRP-1, and TYRP-2) and biologic behavior, tested mycoplasma-free (MycoAlert Mycoplasma Detection Kit (Lonza)) and frozen. Cells were cultured for less than 3 months after thawing.

B16TK cells were derived from a B16.F1 clone transfected with a plasmid expressing the Herpes Simplex Virus thymidine kinase (HSV-1 TK) gene (Evgin et al., *Cancer Immunol. Res.,* 7:828-40 (2019)). Following stable selection in 1.25 µg/mL puromycin, these cells were shown to be sensitive to Ganciclovir (Cymevene) at 5 µg/mL. B16TK cells were grown in DMEM+10% FBS (Life Technologies)+1.25 µg/mL puromycin (Sigma).

B16-CSDE1$^{WT}$, B16-CSDE1$^{C-T}$, Hep3B-CSDE1$^{WT}$, Hep3B-CSDE1$^{C-T}$ or Mel888-CSDE1$^{WT}$ or Mel88-CSDE1$^{C-T}$ cell lines were generated by transfection of parental B16, Hep3B or Mel888 cells with pcDNA3.1 expression vectors expressing either the murine (B16) or human (Hep3B, Mel888) CSDE1 wild type (non-mutated) or CSDE1$^{C-T}$ mutated genes, isolated by PCR from B16 or Hep3B cells which had escaped in vitro oncolysis by VSV-mIFN-β (B16) or VSV-hIFN-β (Hep3B) in the 21 day selection protocol (Huff et al., *Mol. Ther. Oncolytics,* 11:1-13 (2018)) described herein. 48 hours after transfection, cells were selected in G418 (5 mg/mL B16, 3 mg/mL Hep3B, 1 mg/mL Mel888) for 2 weeks. Over-expression of the CSDE1 proteins was confirmed in these bulk G418$^r$ populations of cells by Western Blot.

VSV expressing murine IFNβ (VSV-mIFN-β, human IFN-β (VSV-hIFN-β) (Willmon et al., *Cancer Res.,* 69(19): 7713-20 (2009)), murine CSDE1$^{WT}$, murine CSDE1$^{C-T}$, or GFP (VSV-GFP) was rescued from the pXN2 cDNA plasmid using the established reverse genetics system in BHK cells as described elsewhere (Obuchi et al., *J. Virol.,* 77(16): 8843-56 (2003); Willmon et al., *Cancer Res.,* 69(19):7713-20 (2009); Diaz et al., *Cancer Res.,* 67:2840-8 (2007); and Pulido et al., *Nat. Biotechnol.,* 30(4):337-43 (2012)). All transgenes were inserted between viral G and L genes using the XhoI and NheI restriction sites. VSV co-expressing murine, or human, IFN-β and CSDE1$^{WT}$ or CSDE1$^{C-T}$ were also generated by cloning the CSDE1 genes between the viral M and G genes. Virus titers were determined by plaque assay on BHK cells or on the stated cells lines in the text.

Mice

Female C57BL/6 mice were obtained from The Jackson Laboratory at 6-8 weeks of age and maintained in a pathogen-free BSL2 biohazard facility.

In Vivo Experiments

Mice were challenged subcutaneously with 2×10$^5$ B16 melanoma cells, in 100 µL PBS (HyClone, Logan, UT, USA). Subcutaneous tumors were treated with doses of 5×10$^7$ pfu of VSV delivered intratumorally (IT) in 50 µL of PBS. Tumors were measured using calipers 3 times per week, and mice were euthanized when tumors reached 1.0 cm in diameter. For experiments using immune checkpoint blockade, mice received 300 µg each of anti-mouse PD1 antibodies (clone RMP1-14), per dose intraperitoneally (IP) (BioXCell). Control mice received 300 µg of control rat IgG (Jackson ImmunoResearch).

Immune Cell Activation

Spleens and lymph nodes were immediately excised from euthanized C57Bl/6 mice and dissociated in vitro to achieve single-cell suspensions. Red blood cells were lysed with ACK lysis buffer for 2 minutes. Cells were resuspended at 1×10$^6$ cells/mL in Iscove's Modified Dulbecco's Medium (IMDM; Gibco) supplemented with 5% FBS, 1% penicillin-streptomycin, 40 µmol/L 2-Mercaptoethanol. Cells were co-cultured with target cells at various effector to target ratios or with stimulating peptides. Supernatants were assayed for TNFα and IFNγ by ELISA as directed in the manufacturer's instructions (Mouse TNFα or Mouse IFN-γ ELISA Kit, OptEIA, BD Biosciences, San Diego, CA).

In Vitro Selection of Virus Resistant Populations

B16, Hep3B, or Mel888 cells were infected at an MOI of 0.01 (VSV) for 1 hour, washed with PBS, and then incubated for 7 days. Dead cells were removed every 2 days by washing with PBS. After 7 days, the cells were collected by detachment with trypsin and re-plated. These cells were subjected to two repeated rounds of infection. After 21 days, or three total rounds of infection, the remaining virus escaped cells were collected.

Sequencing of the CSDE1 Gene

The CSDE1 gene was sequenced using the primer 5'-TCACGAAGTGCTG-CTGAAGT-3' (SEQ ID NO:15) and aligned with NCBI Reference Sequence: NM_144901.4.

APOBEC3 Knockdown

Four separate mouse unique 29mer shRNA retroviral constructs (Origene Technologies, Rockville, MD) as a combination significantly reduced expression of murine APOBEC3 in B16 cells compared to a single scrambled shRNA encoding retroviral construct (Huff et al., *Mol. Ther. Oncolytics,* 11:1-13 (2018)). Optimal knockdown for periods of more than two weeks in culture was achieved using all four constructs pre-packaged as retroviral particles in the GP+E86 ecotropic packaging cell line and used to infect B16 cells at an MOI of ~10 per retroviral construct. In addition, a single scrambled negative control non-effective shRNA cassette was similarly packaged and used to infect cells to generate B16 (scrambled shRNA) cells.

Hep3B cells were infected with a retroviral vector encoding either full length functional APOBEC3B or a mutated, non-functional form of APOBEC3B as a negative control obtained from Reuben Harris (University of Minnesota, MN) (Evgin et al., *Cancer Immunol. Res.,* 7:828-40 (2019); Huff et al., *Mol. Ther. Oncolytics,* 11:1-13 (2018); and Driscoll et al., *Nat. Comm.,* 11(1):790 (2020)). Infected populations were selected for 7 days in hygromycin to generate Hep3B (APOBEC3B) or Hep3B (APOBEC3B INACTIVE) cell lines and used for experiments as described.

Protein Expression Analysis

Cells were lysed in NP40 lysis buffer containing Pierce Protease inhibitor tablets at a final concentration of 1× (ThermoScientific). Protein lysates were quantified by BCA assay according the manufacturer's instructions (Pierce-ThermoScientific). Whole tumor cell lysates, recovered from mice in vivo, were normalized by protein concentration prior to ELISA determination of IL-12 and TNF-α (OptEIA, BD Biosciences, San Diego) to ensure equal amounts of protein were assayed from tumors of different sizes. For Western blot analysis of CSDE1 (89 KD), 20 µg protein lysate was run on a 4-15% SDS-PAGE gel, transferred to PVDF membrane, and blotted with a rabbit anti-CSDE1 polyclonal antibody (Bethyl Laboratories, Montgomery TX, product number #A303-160A) at a dilution of 1/500, overnight at 4° C. Membranes were washed with 0.05% Tween-20 PBS and then probed with an anti-rabbit secondary antibody (1/50000) in 5% milk. Membranes were developed with chemiluminescent substrate.

Human T Cell In Vitro Education and Re-Stimulation

Peripheral blood mononuclear cells (PBMCs) were isolated from healthy donor apheresis cones. CD3+ T cells were isolated using a magnetic sorting kit (Miltenyi Biotech) and activated using CD3/CD28 beads (ThermoFisher). T cells were co-cultured at a ratio of 10:1 with CD14+ in vitro matured dendritic cells prepared from the same donor preloaded with lysates from target tumor cells at a ratio of 1:10 Target cell lysate:DC. On days 3 and 5, tumor cell lysates were re-added to the co-culture. After 7 days of co-culture, CD3+ T cells were re-isolated using a magnetic sorting kit (Miltenyi Biotech), co-cultured with newly-matured mono-cyte-derived dendritic cells, and loaded with tumor cell lysate at a ratio of 1:10 Target cell lysate:DC. Three days later, supernatant was collected for interferon gamma ELISA (R&D).

In separate experiments, CD3+ T cells from donor 3 were treated as above for 7 days, and re-isolated by magnetic sorting. $10^4$ target tumor cells (Hep3B parental or Hep3B-VSV-hIFN-β 21d ESC) were treated for 24 hours with hIFN-γ (200 U/mL for 12 hours) and then co-cultured with $10^5$ of the previously primed T cells (primed/expanded on either Hep3B parental or Hep3B-VSV-hIFN-β 21 d ESC cells) (triplicate wells per treatment). A further $10^5$ T cells were added after 48 hours. At 120 hours post co-culture, wells were washed ×3 with PBS, and the surviving adherent cells were counted. Autologous monocyte-derived dendritic cells were matured by isolating CD14+ cells by magnetic sorting (Miltenyi Biotech), followed by incubation with human GM-CSF (800 U/mL) and IL-4 (1000 U/mL). On Days 3 and 5, media was replaced with human GM-CSF (1600 U/mL) and IL-4 (1000 U/mL). On Day 7, non-adherent cells were collected, washed with PBS, and resus-pended in medium containing GM-CSF (800 U/mL), IL-4 (1000 U/mL), TNF-alpha (1100 U/mL), IL-1beta (1870 U/mL), IL-6 (1000 U/mL), and PGE2 (1 μg/mL). Two days later, dendritic cells were harvested for co-incubation with freshly isolated, or pre-activated, T cells at a ratio of 1:10 as described above.

siRNA Knockdown of CSDE1

Target cells were transfected with no siRNA, 600 pmoles of Silence select Negative siRNA or with 600 pmoles of [s15373+15374 siRNA] (2 CSDE1-specific siRNA) (Mar-tinez-Useros et al., *J. Clin. Med.*, 8(4):560 (2019)), and levels of CSDE1 assayed by Western Blot 24 or 48 hours later.

Statistical Analyses

All analysis was performed within GraphPad Prism soft-ware (GraphPad). Multiple comparisons were analyzed using one-way or two-way ANOVAs with a Tukey's post-hoc multi comparisons test. Survival data was assessed using the Log-Rank test using a Bonferroni correction for multiple comparisons. Data is expressed as group mean±SD. Escape from VSV-IFNβ Oncolysis is Associated with High Frequency Mutation in CSDE1

Figures 1A, 1B, 1C:
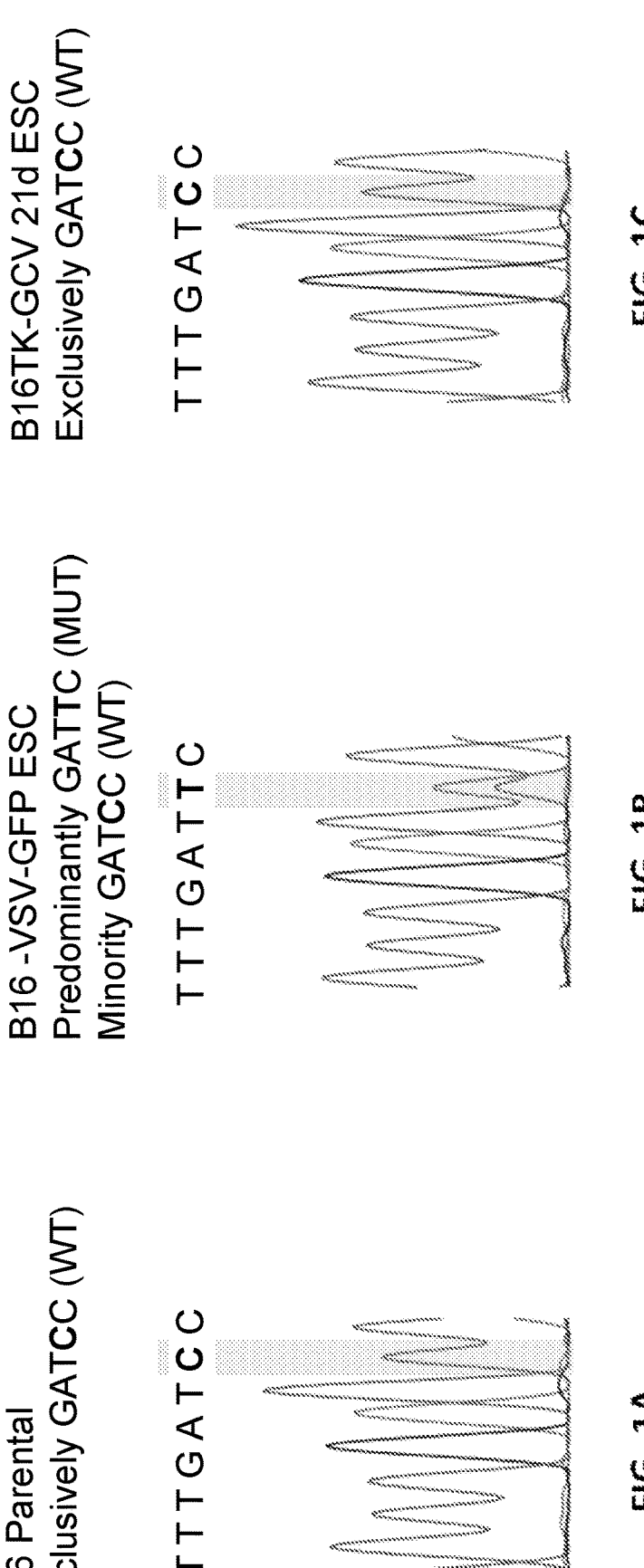
Figure 1D:
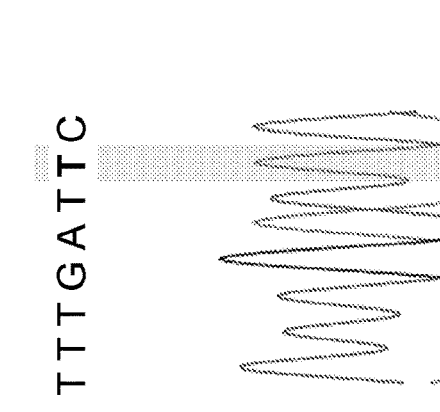
Figure 1E:
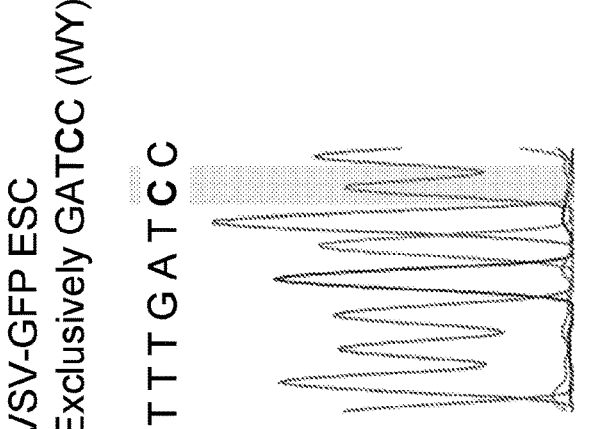
Figure 1F:
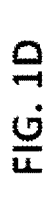
Figures 1G, 1H, 1I:
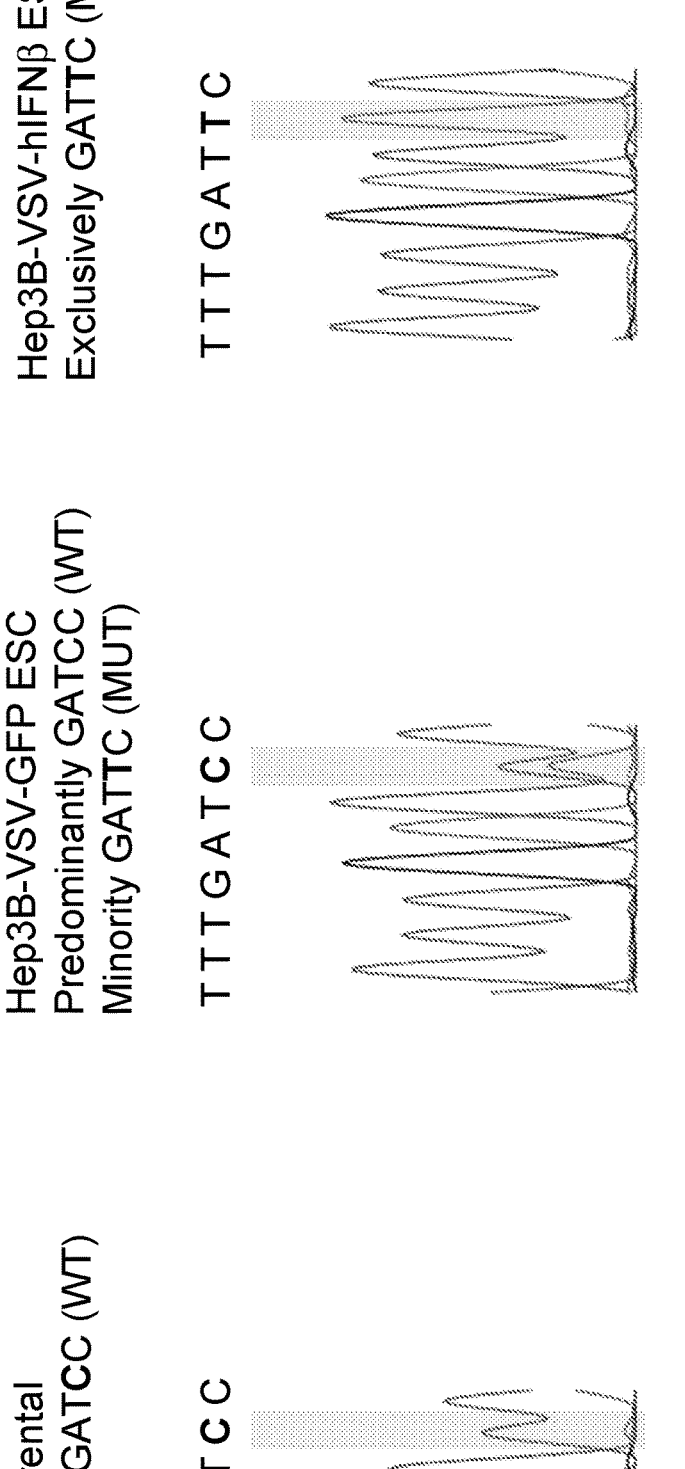

B16 populations selected for escape from VSV-GFP (B16-VSV-GFP-ESC) were heterogeneous for both CSDE1$^{WT}$ and CSDE1$^{C-T}$ (FIGS. 1A and 1B). B16-HSVtk cells that escaped GCV chemotherapy (Evgin et al., *Cancer Immunol. Res.*, 7:828-40 (2019)) had no mutation in CSDE1 (FIG. 1C). Expression of IFNβ from the virus increased IFN, APOBEC3, and the number of virus-resistant cells (Huff et al., *Mol. Ther. Oncolytics*, 11:1-13 (2018)). Whereas CSDE1$^{C-T}$ was present at ~50% in B16-VSV-GFP-ESC cells, over 90% of CSDE1 sequence in B16-VSV-IFNβ-ESC cells was CSDE1$^{C-T}$ suggesting mutation at most of the alleles in ESC cells (FIG. 1D). However, when both B16-VSV-GFP-ESC and B16-VSV-IFNβ-ESC cells were selected from B16 cells expressing shRNA against mAPOBEC3 (Huff et al., *Mol. Ther. Oncolytics*, 11:1-13 (2018)), only CSDE1$^{WT}$ was present (FIGS. 1E and 1F). CSDE1$^{C-T}$ was present at >90% in murine and human VSV-IFNβ-ESC cells, and always at higher clonality than in VSV-GFP-ESC cells (FIGS. 1G, 1H, and 1I). CSDE1$^{C-T}$ was present in Mel888 tumors that escaped VSV-hIFNβ in vivo (Huff et al., *Mol. Ther. Oncolytics*, 11:1-13 (2018)), but only in ~30-50% of the cells (FIG. 1J), probably reflecting less efficient in vivo infection.

Taken together, these results are consistent with the CSDE1$^{C-T}$ mutation, which has a typical mAPOBEC3/APOBEC3B signature (TTCA-TCCA) (Driscoll et al., *Nat. Comm.*, 11(1):790 (2020); Walker et al., *Nat. Commun.*, 6:6997 (2015); and Roberts et al., *Nat. Genet.*, 45(9):970-6 (2013)), being induced through Type I IFN-induction of mAPOBEC3/hAPOBEC3B activity at high clonality in VSV-IFNβ ESC cells across species and tumor types (FIGS. 1A-J).

CSDE1 is a Positive Mediator of VSV Replication and Oncolysis

Figure 2A:
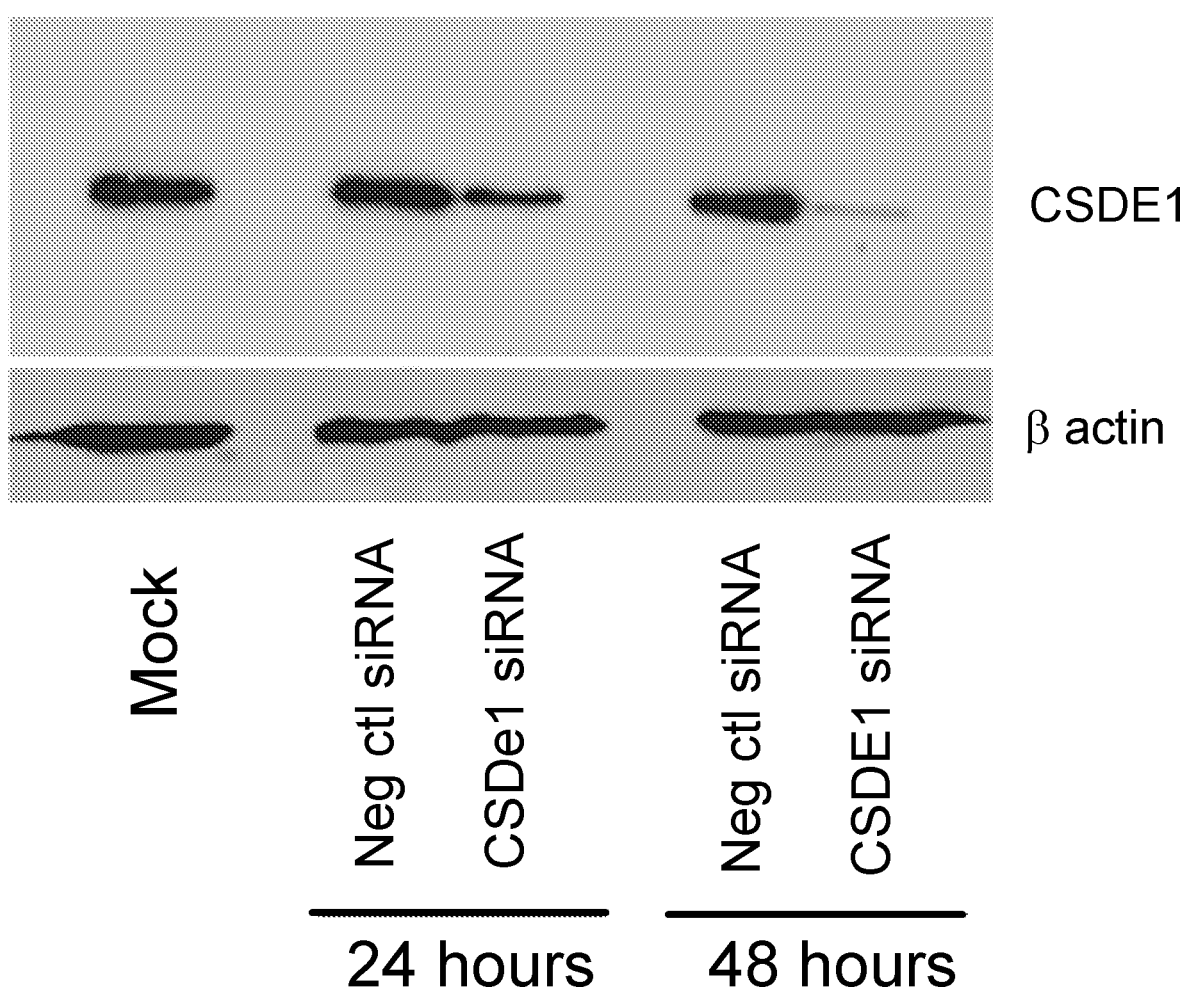
FIGS. 2A-2G. CSDE1 is a positive modulator of VSV replication (FIG. 2A) Hep3B cells were transfected with no siRNA, Negative control siRNA or with [s15373+15374 siRNA] (2 CSDE1-specific siRNA) and levels of CSDE1 assayed by Western Blot 24 or 48 hours later.
Figure 2D:
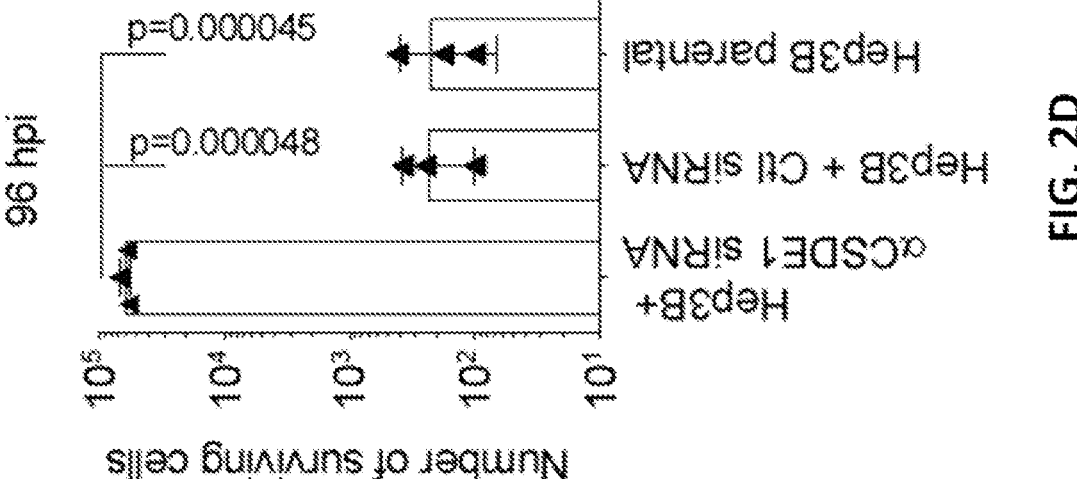
Figure 2C:
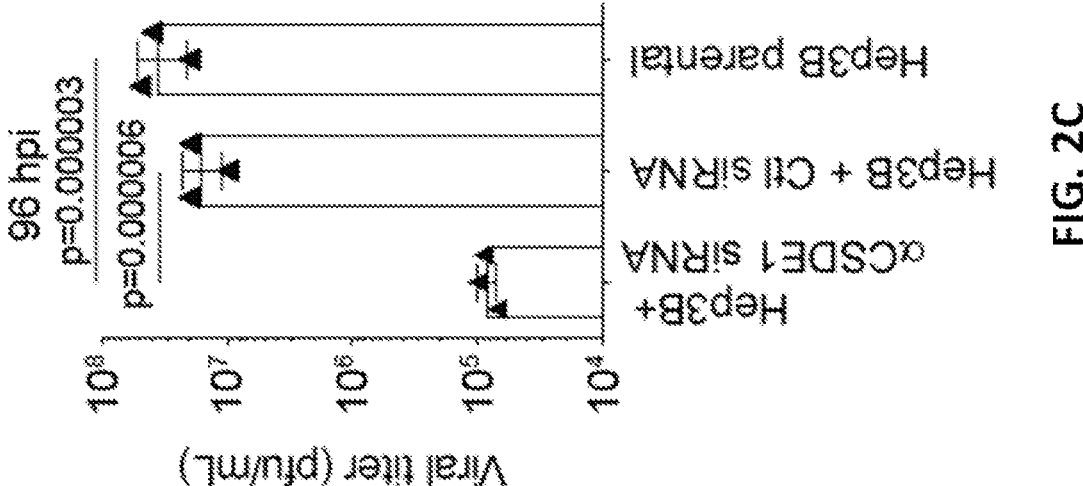
Figure 2B:
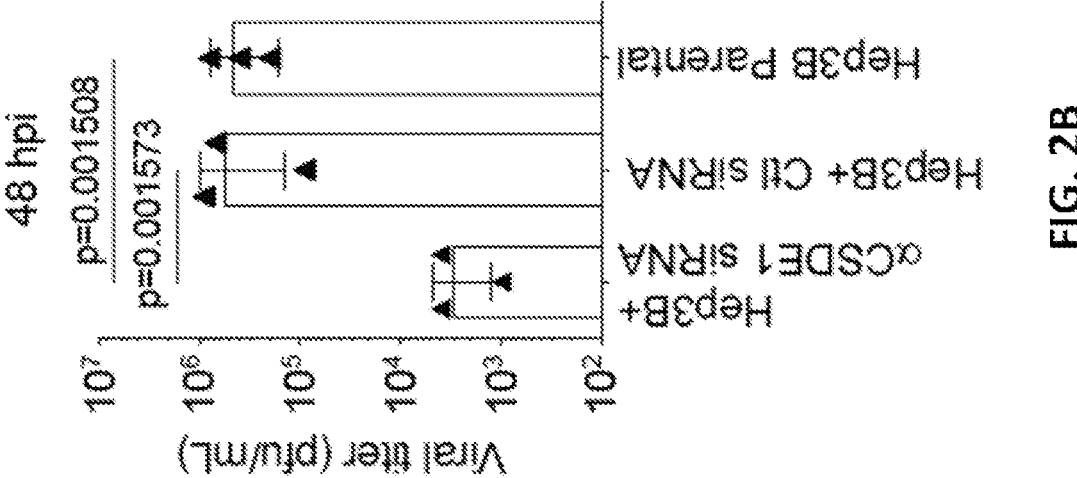

These results suggested that CSDE1 may be involved in the replication/oncolytic activity of VSV, that the CSDE1$^{C-T}$ mutation drives escape, and that co-expression of IFNβ enhances mutation of this escape-promoting gene. Consis-tent with this, replication of (FIGS. 2A-C), and oncolysis by (FIG. 2D), VSV-GFP was reduced by >2 orders of magni-tude by CSDE1 knock down in human cells.

CSDE1$^{C-T}$ Inhibits VSV Replication

Figures 2E, 2F:
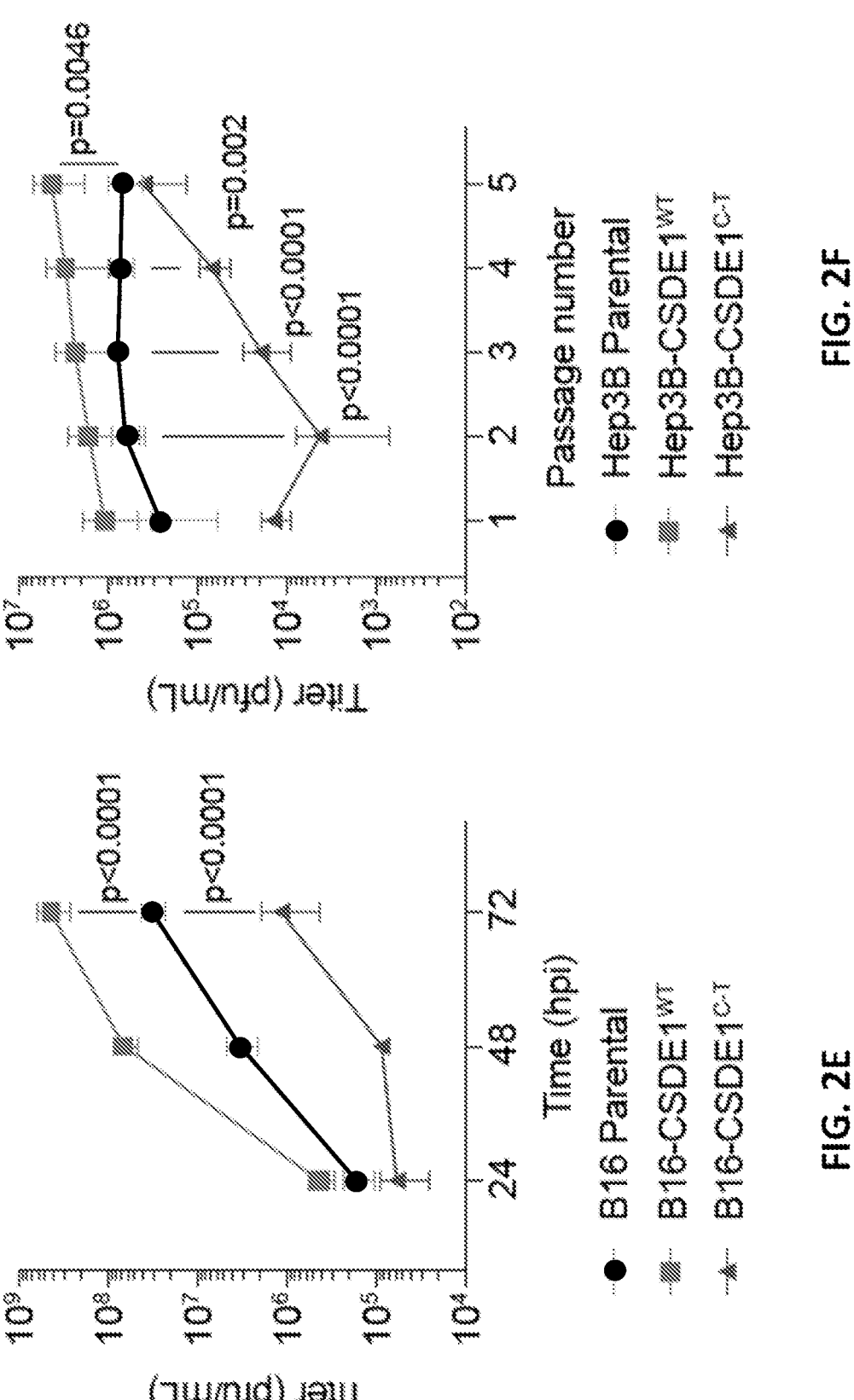
Figure 2G:
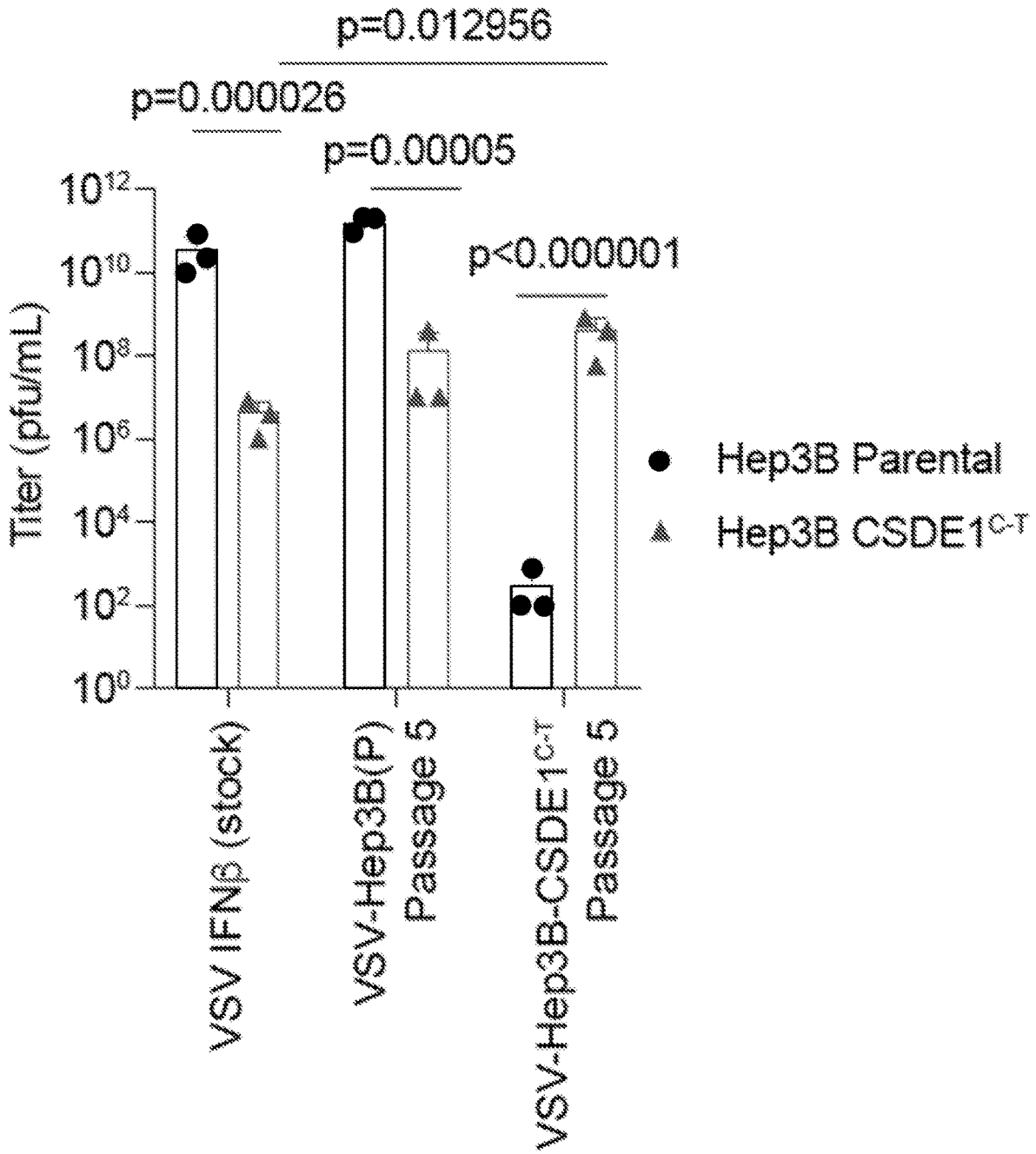

Similarly, VSV-IFNβ replicated to significantly higher titers in B16 cells over-expressing CSDE1$^{WT}$ (p<0.0001 at 72 hours) (FIG. 2E), but significantly worse in B16 cells over-expressing CSDE1$^{C-T}$ (p<0.0001 at 72 hours), com-pared to parental B16 (FIG. 2E). B16-CSDE1$^{C-T}$ cells still have both normal alleles of CSDE1 in situ and express endogenous CSDE1$^{WT}$, showing that CSDE1$^{P5S}$ acts as a dominant-negative regulator of VSV replication and exerts a strong selective pressure on the viral genome, across species and histological types. Multiple passage of VSV-IFNβ through human Hep3B-CSDE1$^{WT}$ increased replica-tion compared to passage through Hep3BP parental cells (FIG. 2F). In contrast, after just a single passage through Hep3B-CSDE1$^{C-T}$ cells, titers were significantly lower than with passage through Hep3BP (p<0.0001) (FIG. 2F). By passage 3 through Hep3B-CSDE1$^{C-T}$, titers began to recover, and reached almost Hep3BP levels by passage 5 (FIG. 2F). Virus recovered from 5 passages through Hep3BP (from FIG. 2F), replicated well on Hep3BP cells (FIG. 2G) but had orders of magnitude lower titers on Hep3B-CSDE1$^{C-T}$ cells (FIG. 2G). Conversely, virus from 5 pas-sages through Hep3B-CSDE1$^{C-T}$ replicated poorly on Hep3BP cells but at near wild-type levels on Hep3B-CSDE1$^{C-T}$ cells (FIG. 2G). Thus, VSV-IFNβ can, if given sufficient time, adapt to the emergence of escape cells by complementing the CSDE1$^{C-T}$ mutation.

VSV Expressing an Escape Associated Tumor Antigen

Figure 3A:
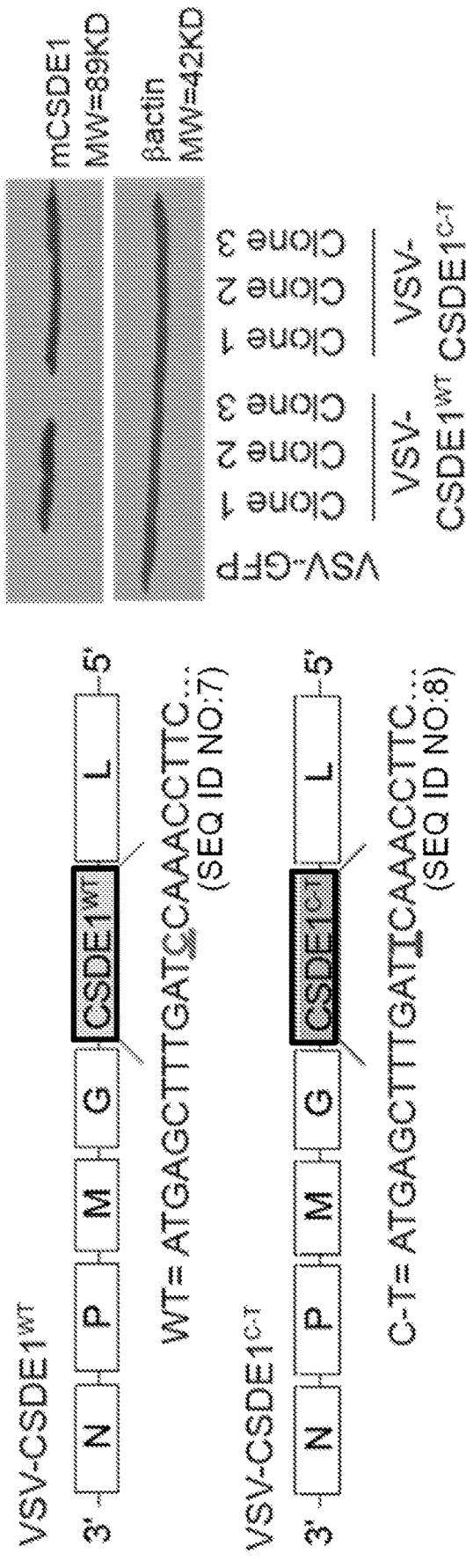
Figure 3B:
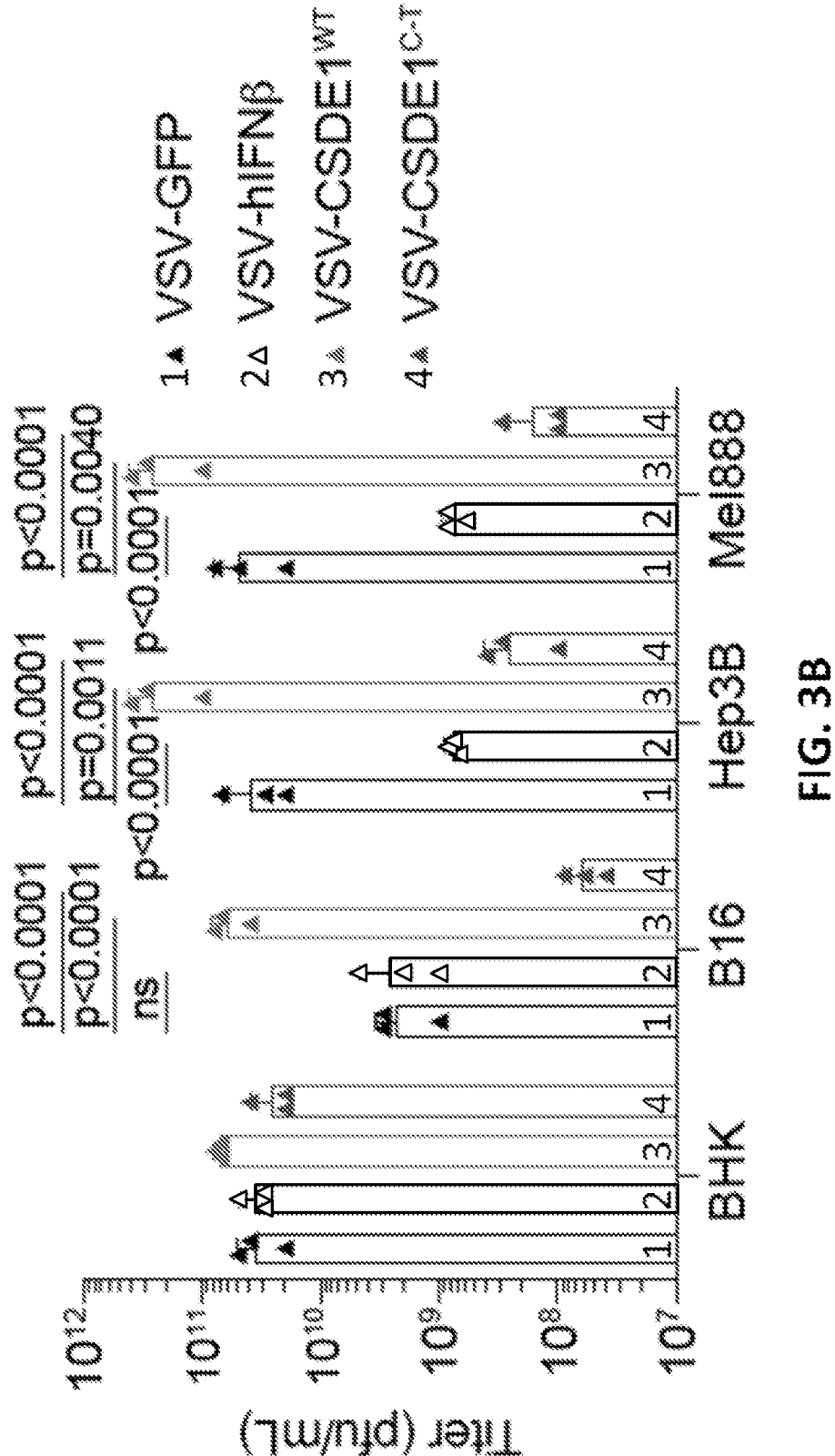

The APOBEC3B-generated CSDE1$^{C-T}$ mutation creates a heteroclitic neo-epitope in the B16/C57Bl/6 model (Driscoll et al., *Nat. Comm.*, 11(1):790 (2020)), and is highly selected for in tumors forced to escape VSV-IFNβ. This treatment-driven neo-antigenesis makes CSDE1$^{P5S}$ an Escape-Asso-ciated Tumor Antigen (EATA) target for immunotherapy against treatment-resistant tumors. Therefore, viruses expressing either CSDE1$^{WT}$ or the CSDE1$^{P5S}$ EATA were constructed (FIG. 3A). The nucleic acid sequence of the VSV-CSDE1$^{WT}$ construct (SEQ ID NO:16) is shown in FIG. 16; the underlined sequence encodes CSDE1. Consistent with FIGS. 2A-G, over-expression of CSDE1$^{WT}$ from VSV significantly enhanced viral replication on human and murine (but not hamster) cells, compared to VSV-GFP (FIG. 3B). Conversely, viral-driven CSDE1$^{P5S}$ exerted a signifi-cant dominant-negative effect (FIG. 3B). Low MOI infec-tion of Hep3BP or B16 cells with VSV-IFNβ-CSDE1$^{WT}$ significantly reduced both escape (FIG. 3C) and the escape-enabling CSDE1$^{C\text{-}T}$ mutation (~10-50% in FIG. 3D, compared to >90% in FIG. 1I) compared to VSV-IFNβ.

Trap and Ambush Immunotherapy for Tumor Escape

Figure 4A:
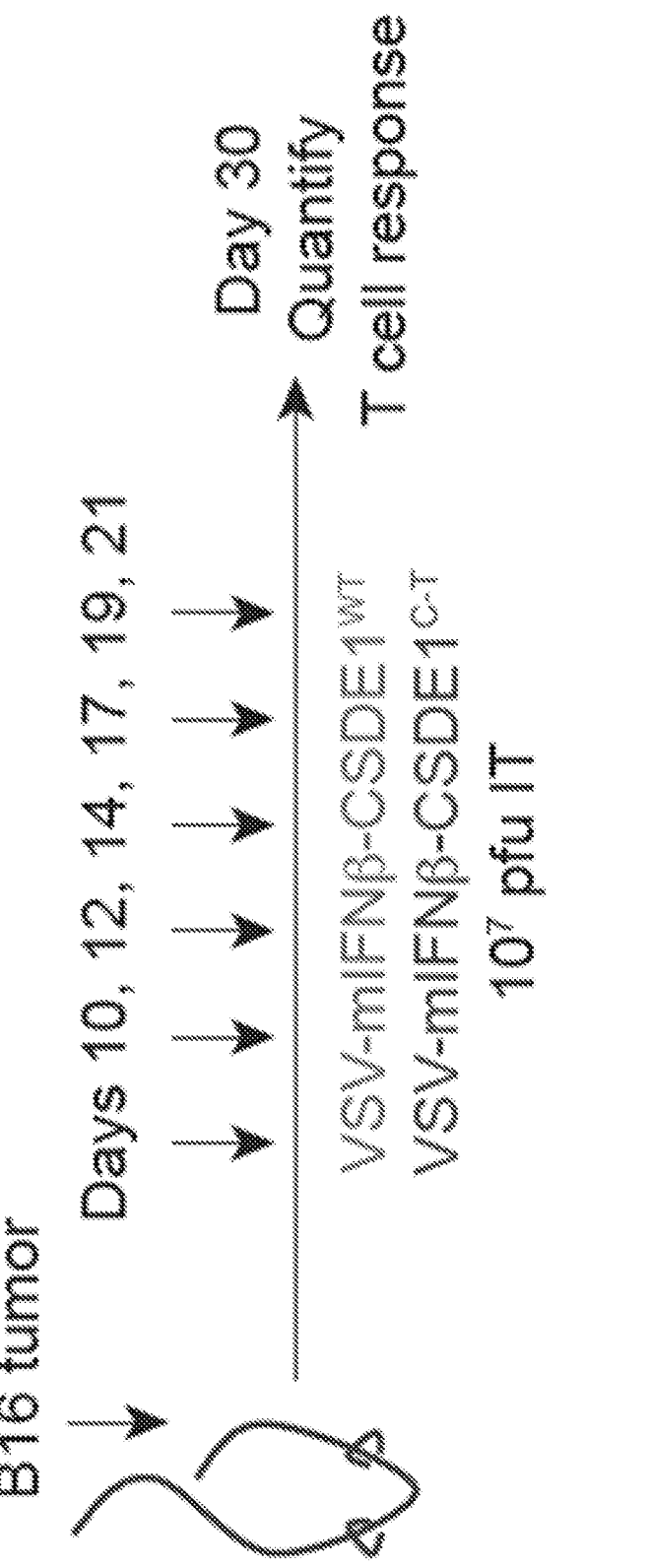
FIGS. 4A-4G. Virotherapy trap and immunotherapy ambush.
Figure 4B:
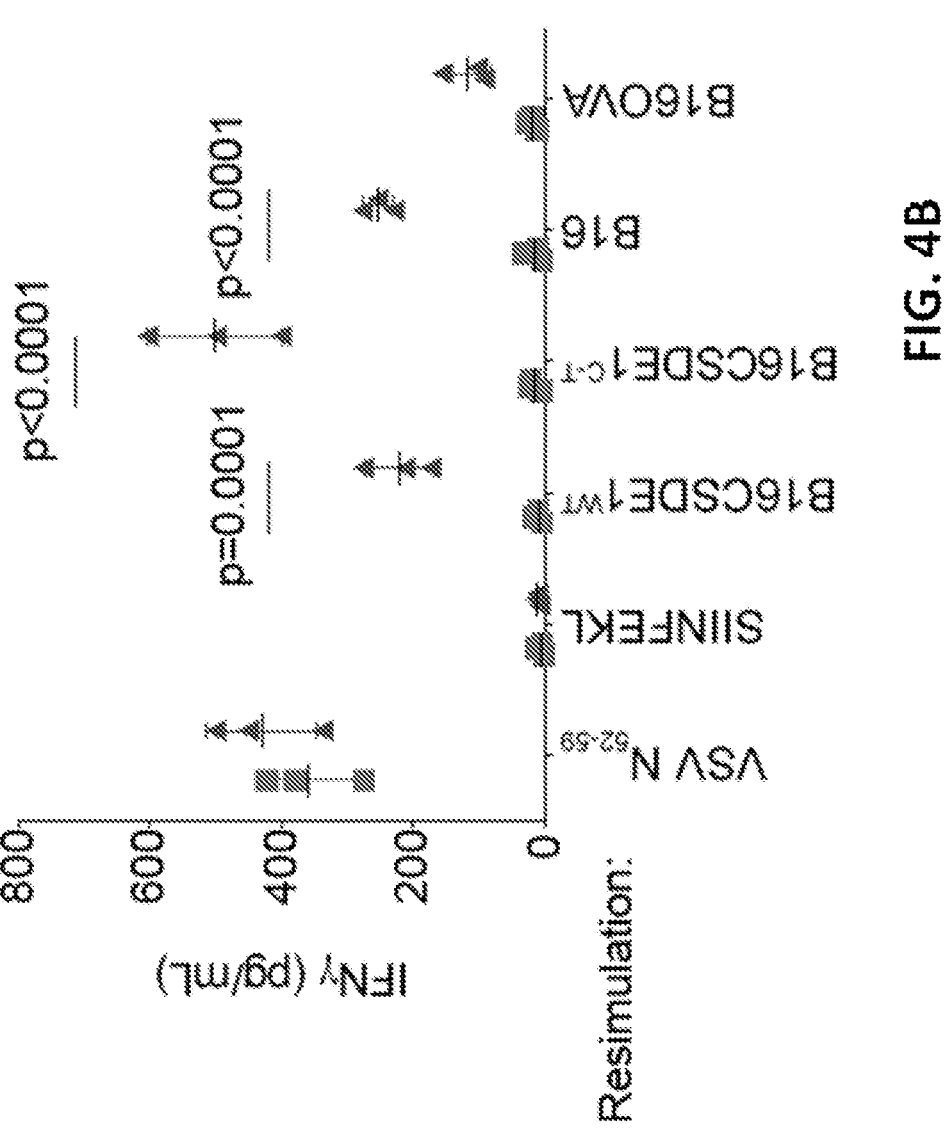
Figure 4C:
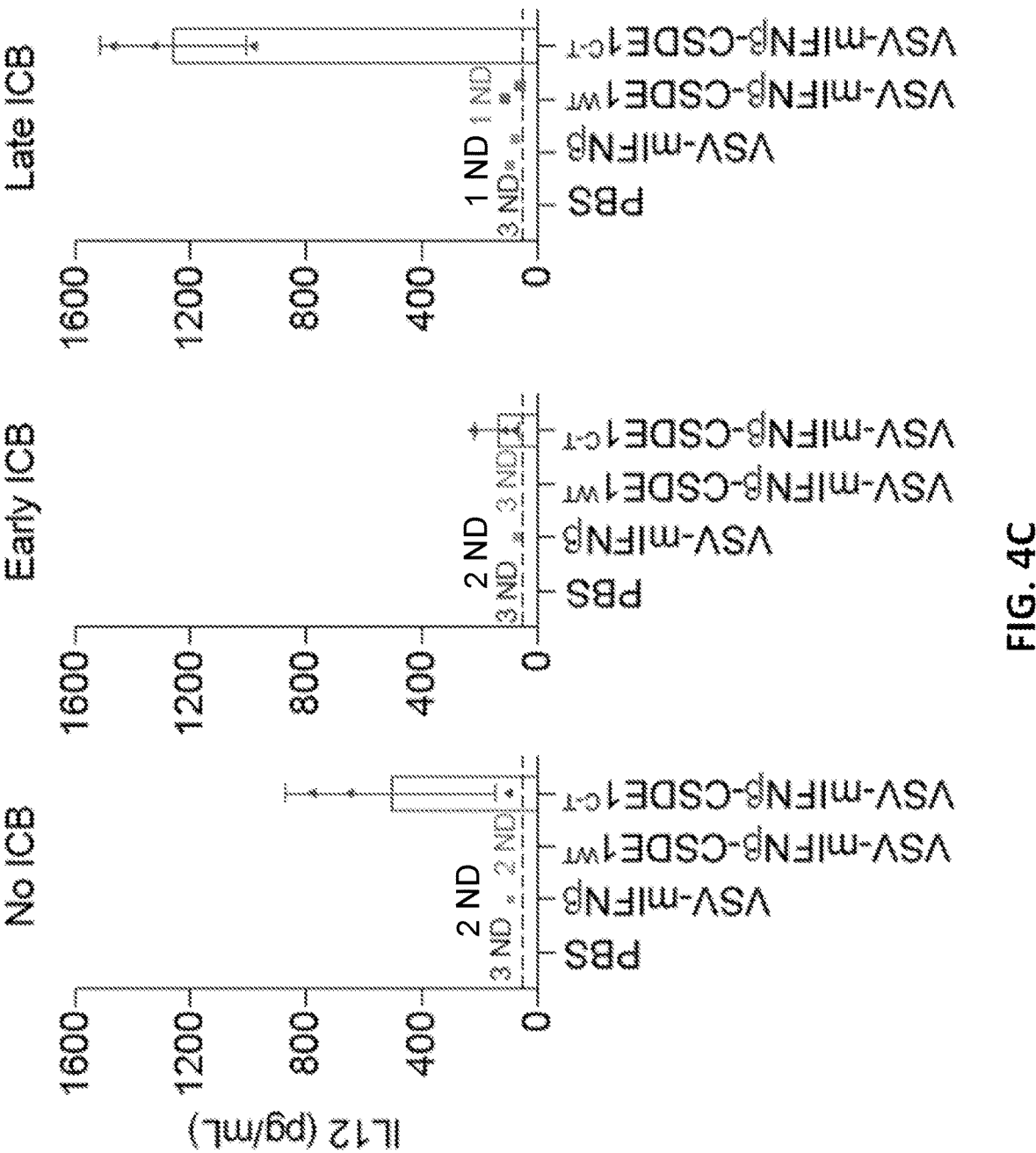
Figure 4D:
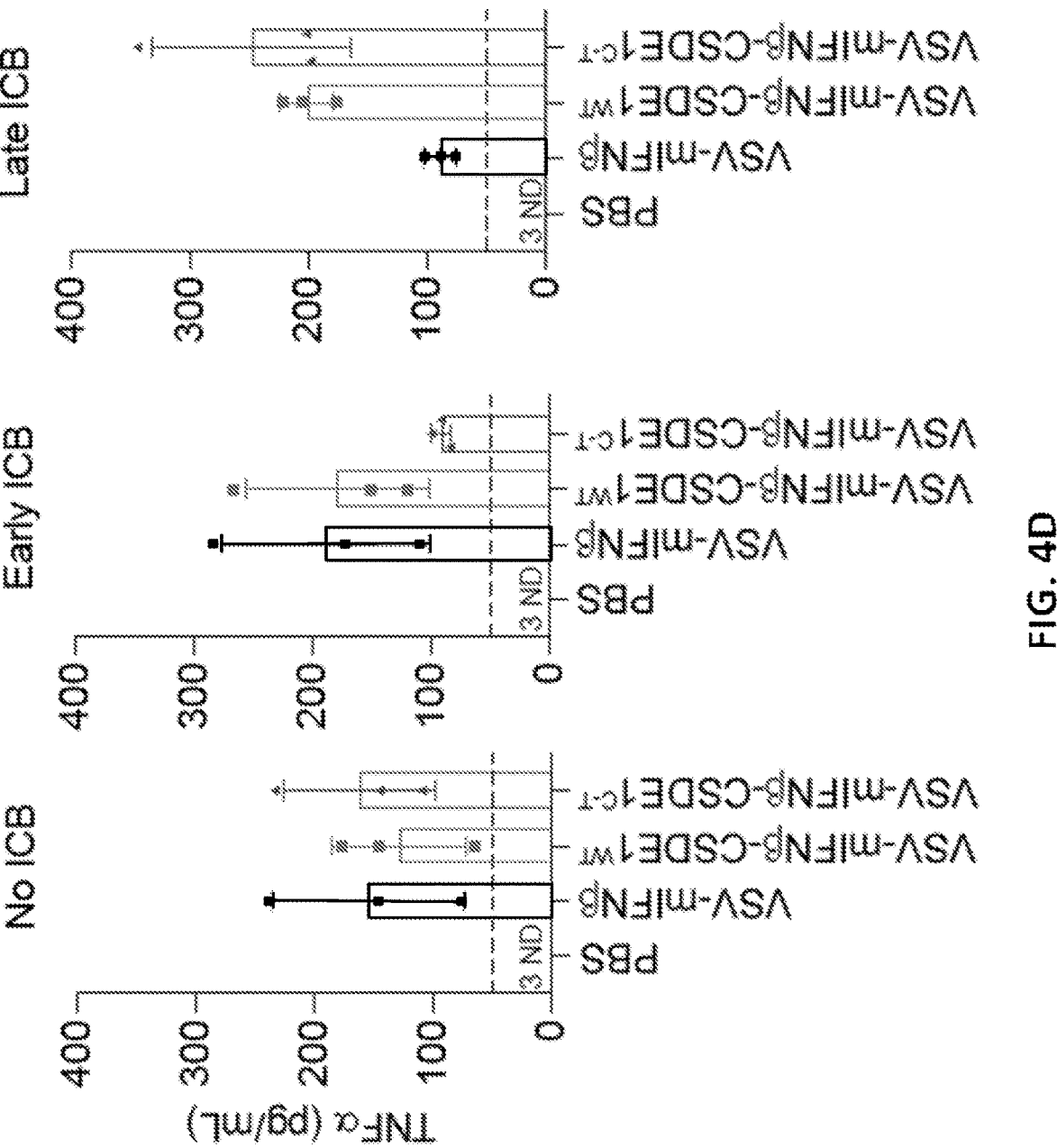

Mice treated intra-tumorally with VSV-mIFNβ-CSDE1$^{WT}$ or VSV-mIFNβ-CSDE1$^{C\text{-}T}$ (FIG. 4A) generated comparable strong anti-viral T cell responses (FIG. 4B). Although VSV-mIFNβ-CSDE1$^{WT}$ did not generate anti-CSDE1$^{WT}$ T cells, VSV-mIFNβ-CSDE1$^{C\text{-}T}$ induced potent T cell responses against the CSDE1$^{P5S}$ neoantigen (FIG. 4B), as well as weaker responses against B16-CSDE1$^{WT}$, and B16 (expressing endogenous CSDE1), confirming that CSDE1$^{P5S}$ acts as a heteroclitic neo-epitope in the C57Bl/6 model (Driscoll et al., Nat. Comm., 11(1):790 (2020)). Only VSV-mIFNβ-CSDE1$^{C\text{-}T}$ induced intra-tumoral IL-12 after 6 i.t. injections (FIG. 4C), which correlated with the anti-tumor T cell response (FIG. 4B). All three viruses induced similar levels of TNF-α within injected tumors (FIG. 4D).

Immune checkpoint blockade (ICB) with anti-PD-1 antibody (Wei et al., Cancer Discov., 8(9):1069-86 (2018); Shi et al., Front Immunol., 11:683 (2020); Saibil et al., Curr. Oncol., 27(Suppl 2):S98-S105 (2020); and Shim et al., Mol. Ther 25(4):962-75 (2017)) concomitant with i.t. virus, significantly decreased IL-12 in VSV-mIFNβ-CSDE1$^{C\text{-}T}$-treated tumors (FIG. 4C). In contrast, anti-PD-1 ICB 4 days after the first viral injection significantly increased IL-12 in VSV-mIFNβ-CSDE1$^{C\text{-}T}$-treated tumors (FIG. 4C). Levels of TNF-α were not significantly altered from no, or early, ICB (FIG. 4D).

Figure 3C:
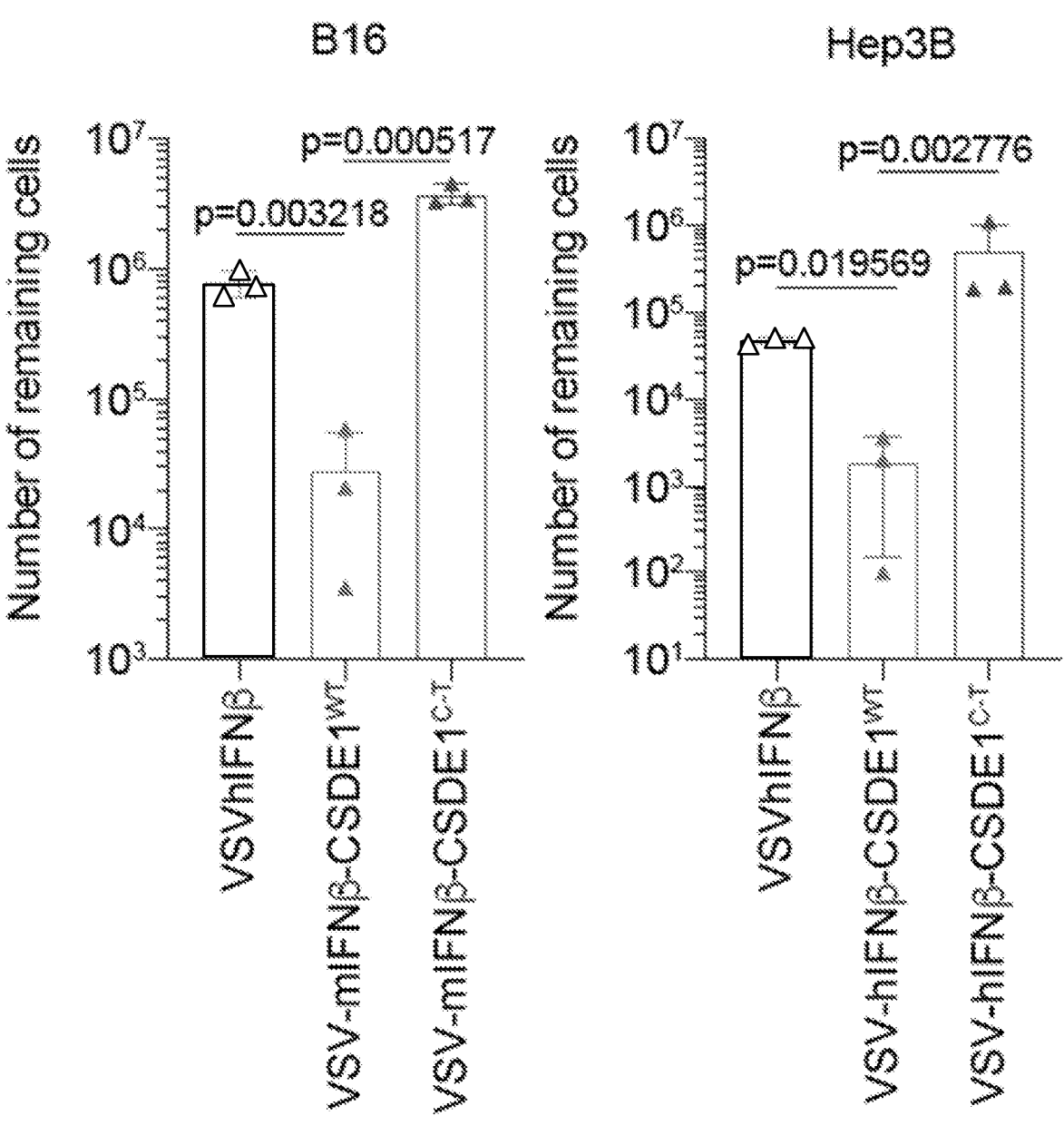
Figure 4E:
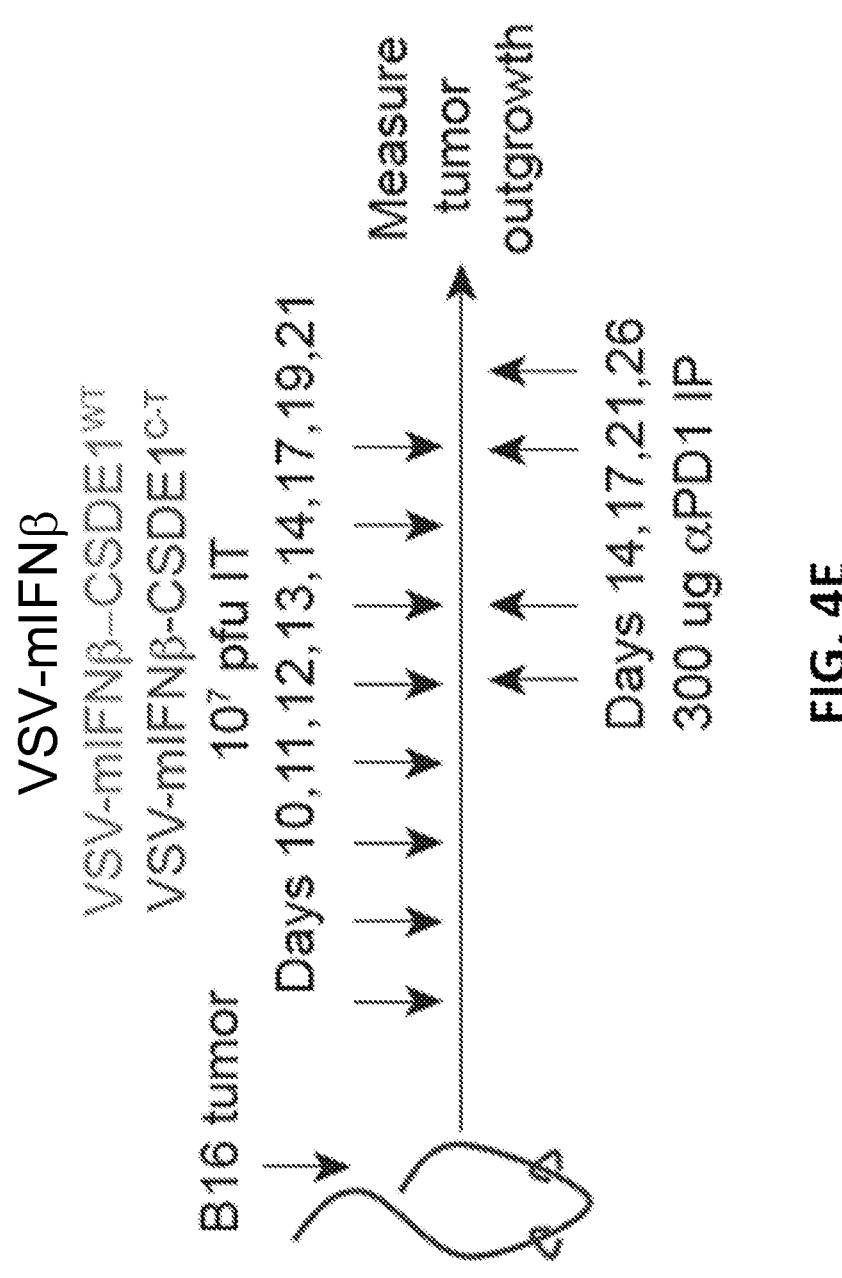
Figures 4F, 4G:
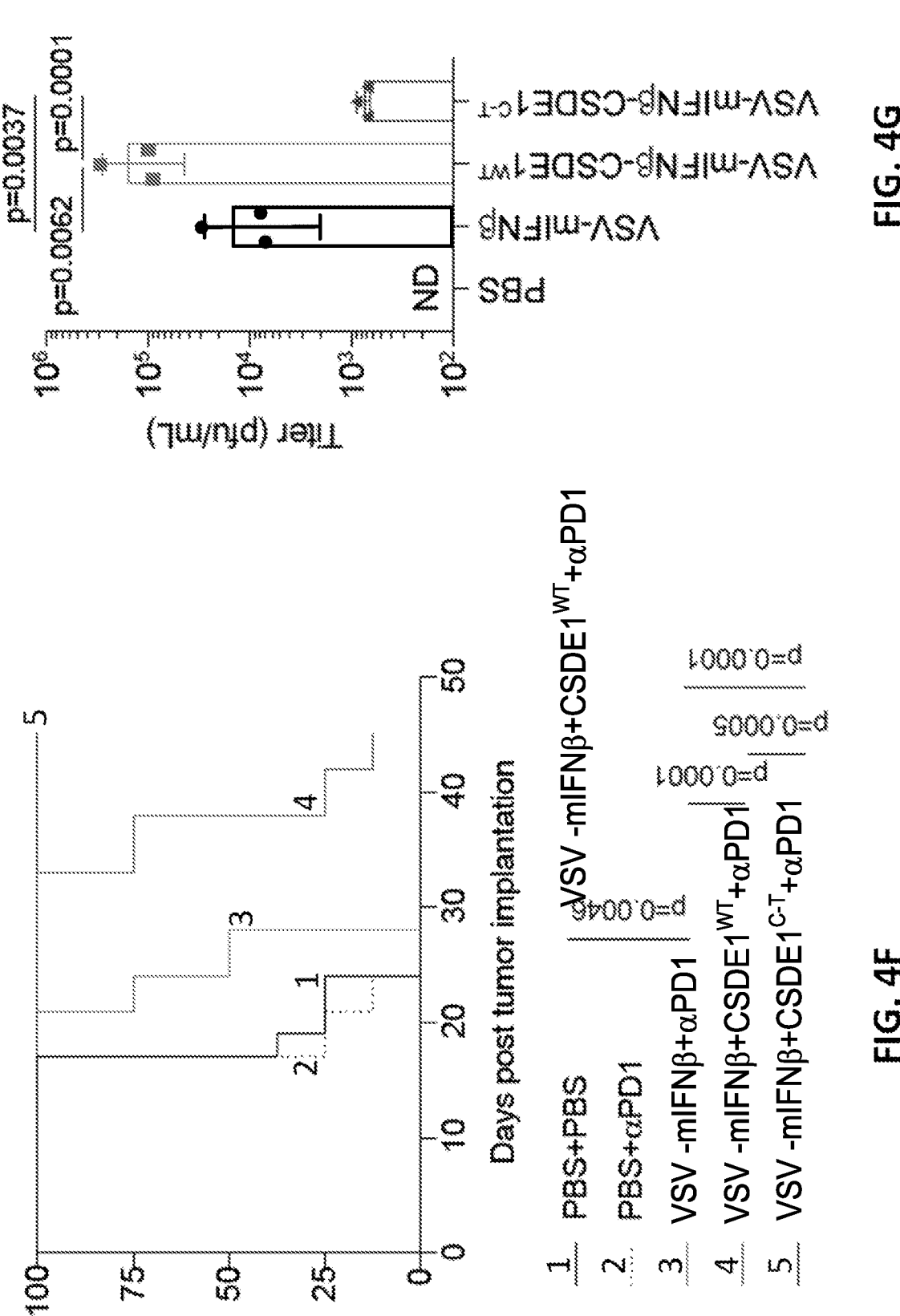

To compare the relative therapeutic contributions of increased viral replication/oncolysis (VSV-mIFNβ-CSDE1$^{WT}$) with decreased oncolysis but treatment-driven neo-antigenesis in VSV-IFNβ-ESC tumors (VSV-mIFNβ-CSDE1$^{C\text{-}T}$), mice were treated i.t. with viruses+anti-PD-1 late after induction of T cell responses (FIG. 4E). VSV-mIFNβ generated therapy, but all tumors eventually escaped (FIG. 4F). VSV-IFNβ-CSDE1$^{WT}$ significantly increased median survival compared to VSV-mIFNβ (FIG. 4F), correlated with enhanced i.t. replication (FIG. 4G) (consistent with FIG. 3). However, expression of the CSDE1$^{P5S}$ EATA from the virus completely prevented tumor escape (FIG. 4F), despite significantly less replication in tumors compared to either VSV-mIFNβ or VSV-mIFNβ-CSDE1$^{WT}$ (FIGS. 4G and 2).

Dendritic Cell Vaccination Against an Escape Associated Tumor Antigen

Figure 5A:
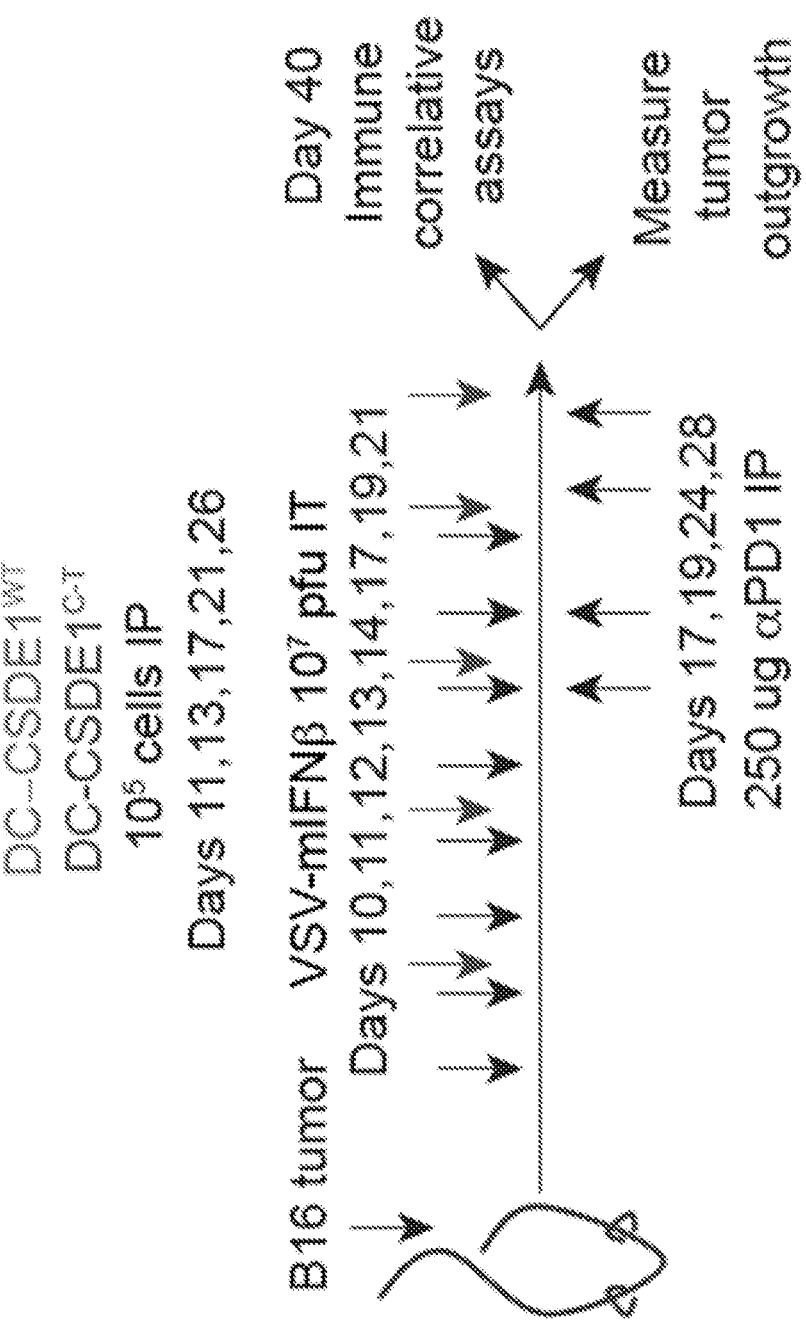
FIGS. 5A-5D. DC-CSDE1$^{C-T}$ vaccination.
Figure 5B:
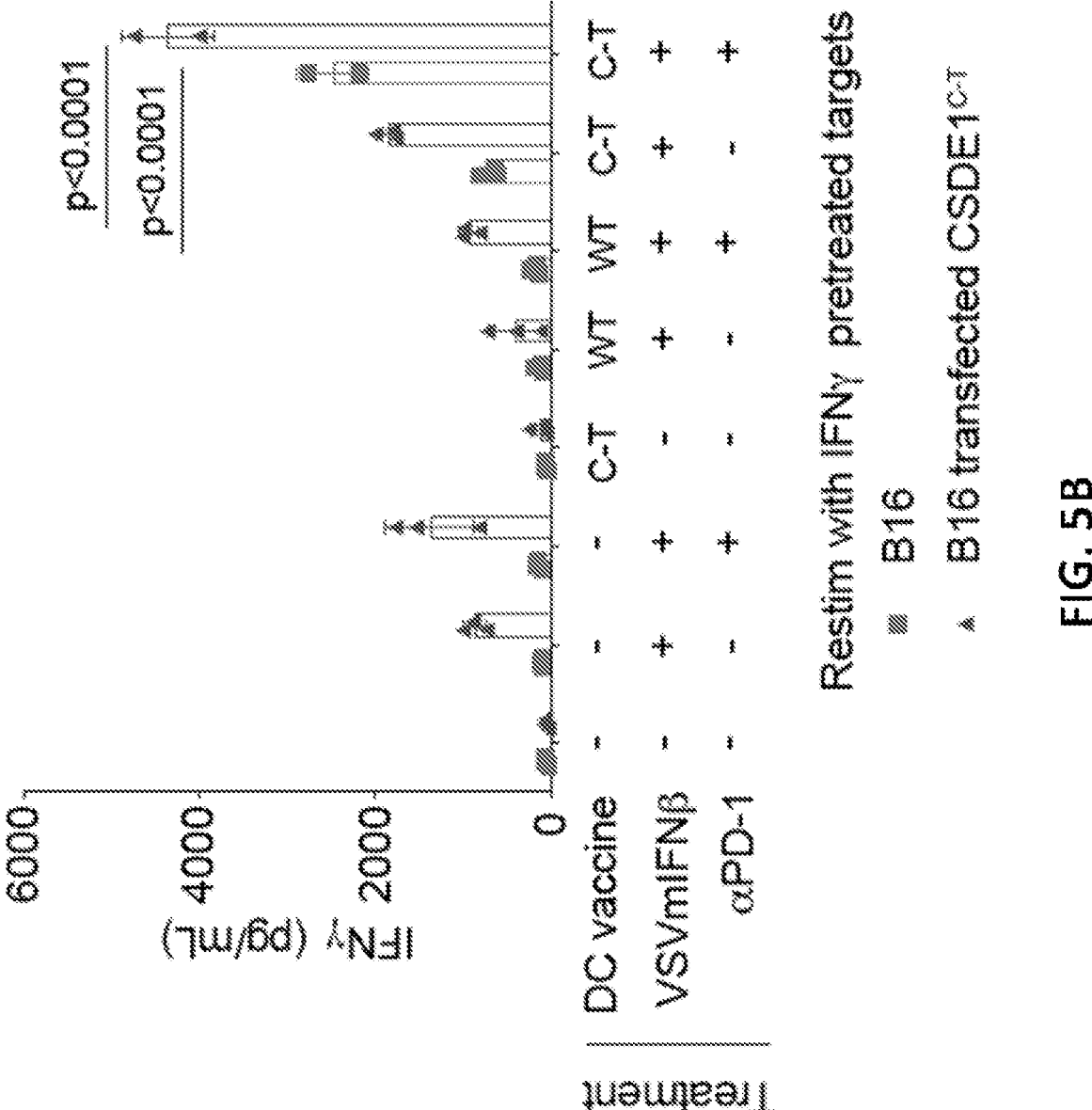
Figure 5C:
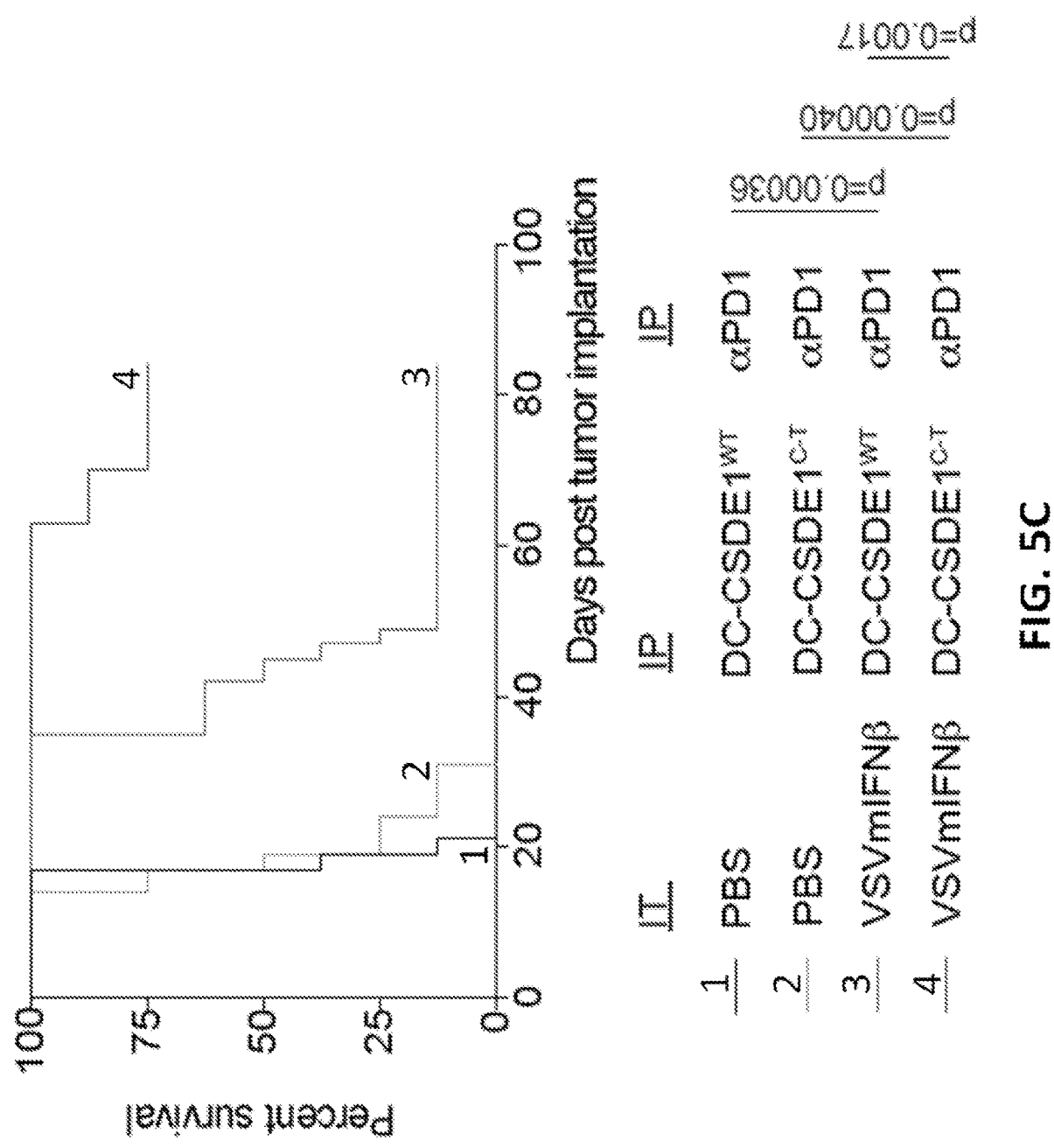
Figure 5D:
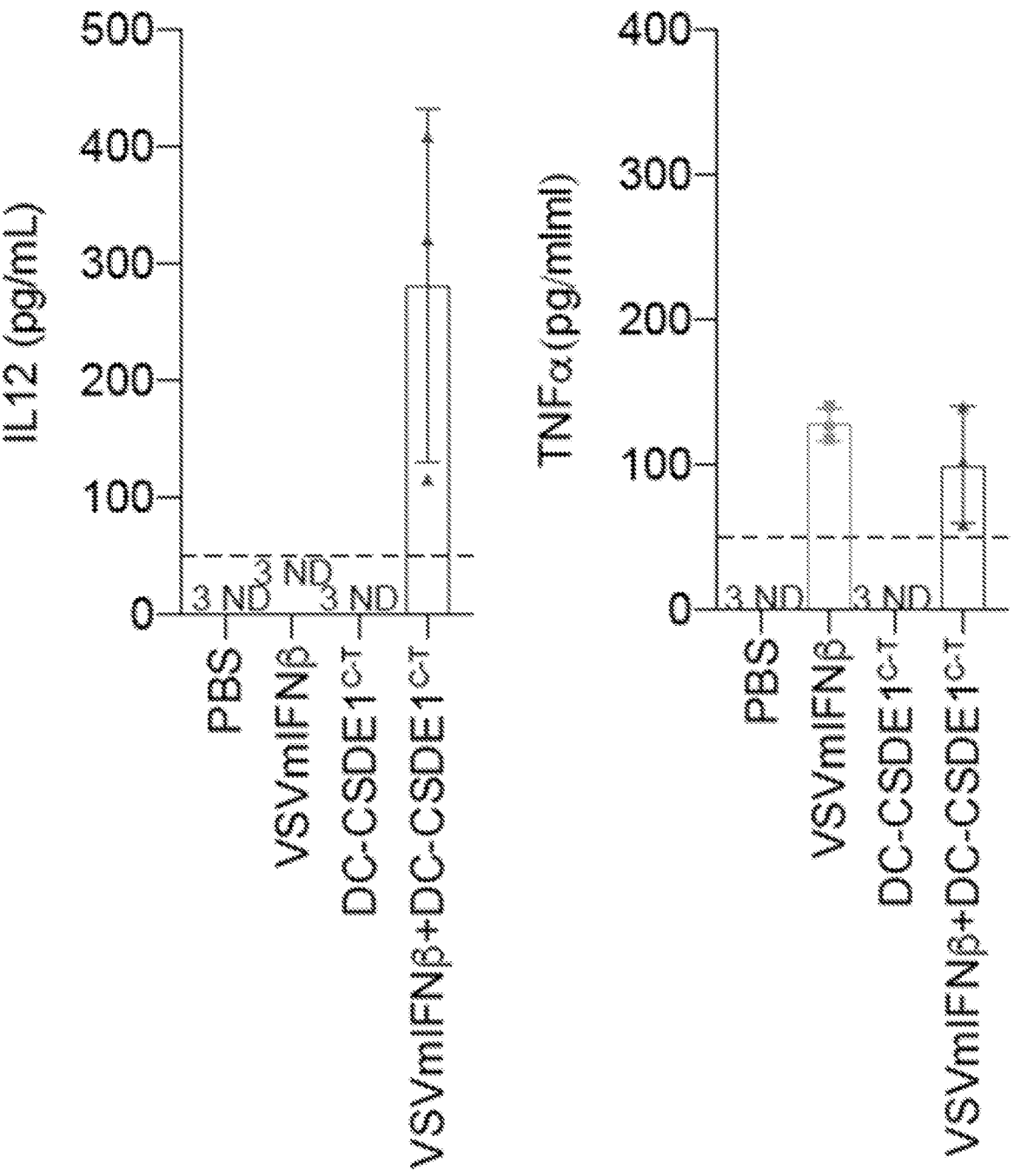

To separate the conflicting effects of decreased oncolysis (FIGS. 3 and 4G) against neo-antigenesis (FIG. 4F), EATA-targeted immunotherapy was tested using dendritic cells expressing CSDE1$^{P5S}$. DC-CSDE1$^{C\text{-}T}$ also generated strong anti-CSDE1$^{P5S}$ T cell responses (FIGS. 5A and 5B). VSV-IFNβ+DC-CSDE$^{C\text{-}T}$+anti-PD-1 significantly enhanced therapy relative to VSV-IFNβ+DC-CSDE$^{WT}$+anti-PD-1 (FIG. 5C), but never achieved the 100% cure rates of VSV-IFNβ-CSDE1$^{C\text{-}T}$+anti-PD-1 (FIG. 4F), which correlated with ~3-fold lower levels of i.t. IL-12 (FIGS. 5D and 4C).

Human Tumor Cells that Escape VSV-IFNβ are Immunogenic

Figure 6A:
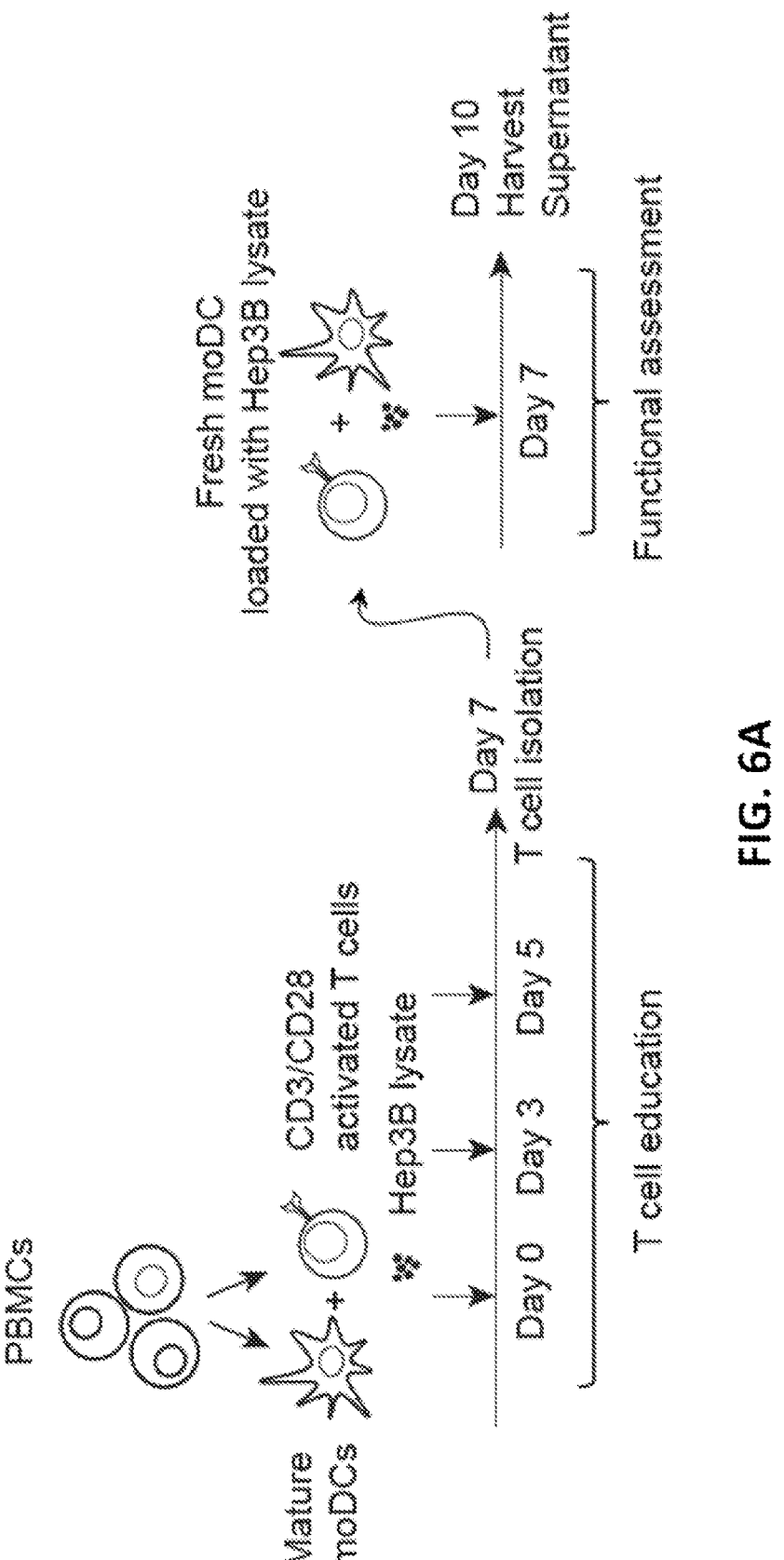
FIGS. 6A-6E. Escape from VSV-hIFNβ is immunogenic.
Figure 6B:
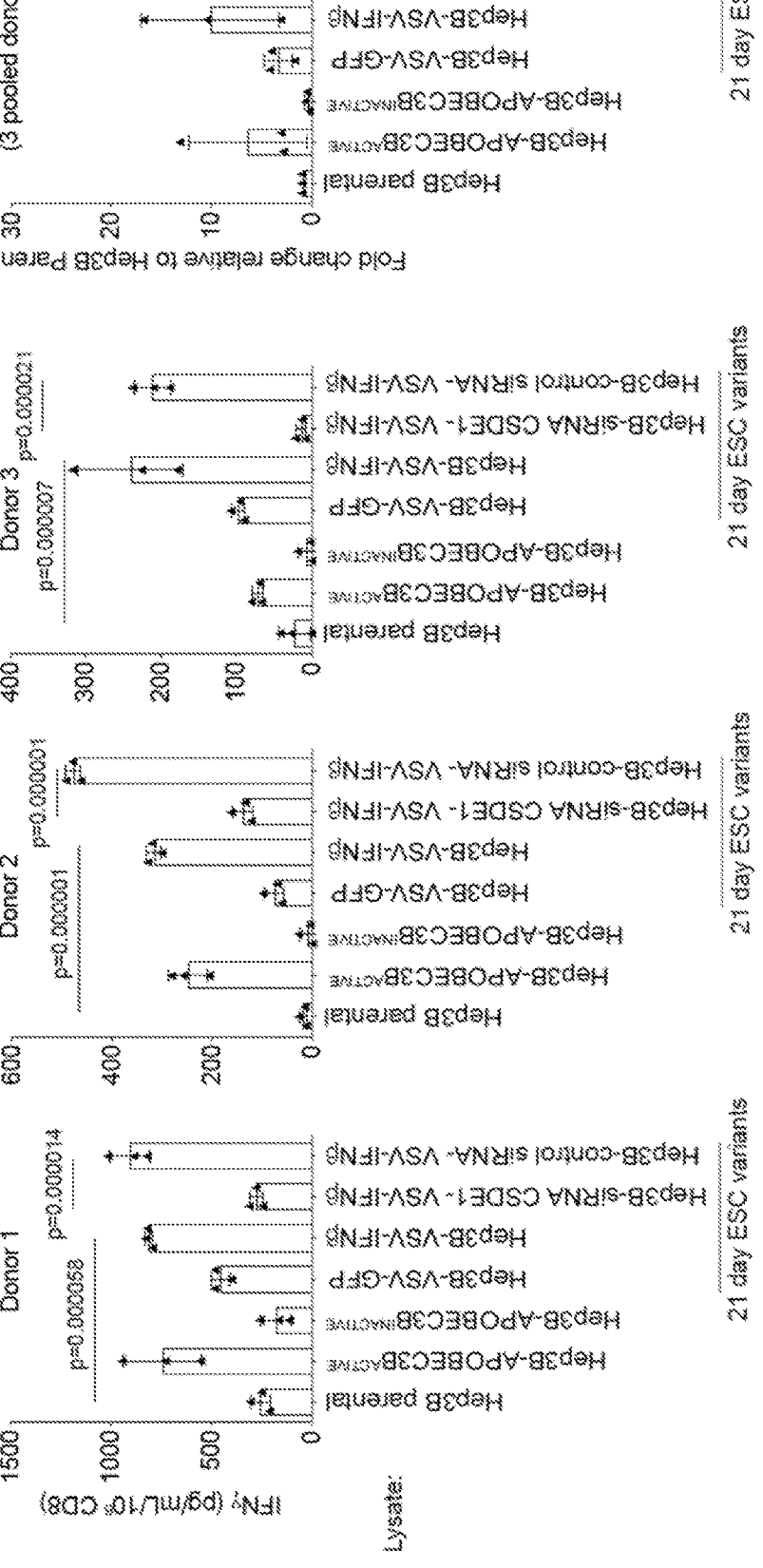
Figure 6C:
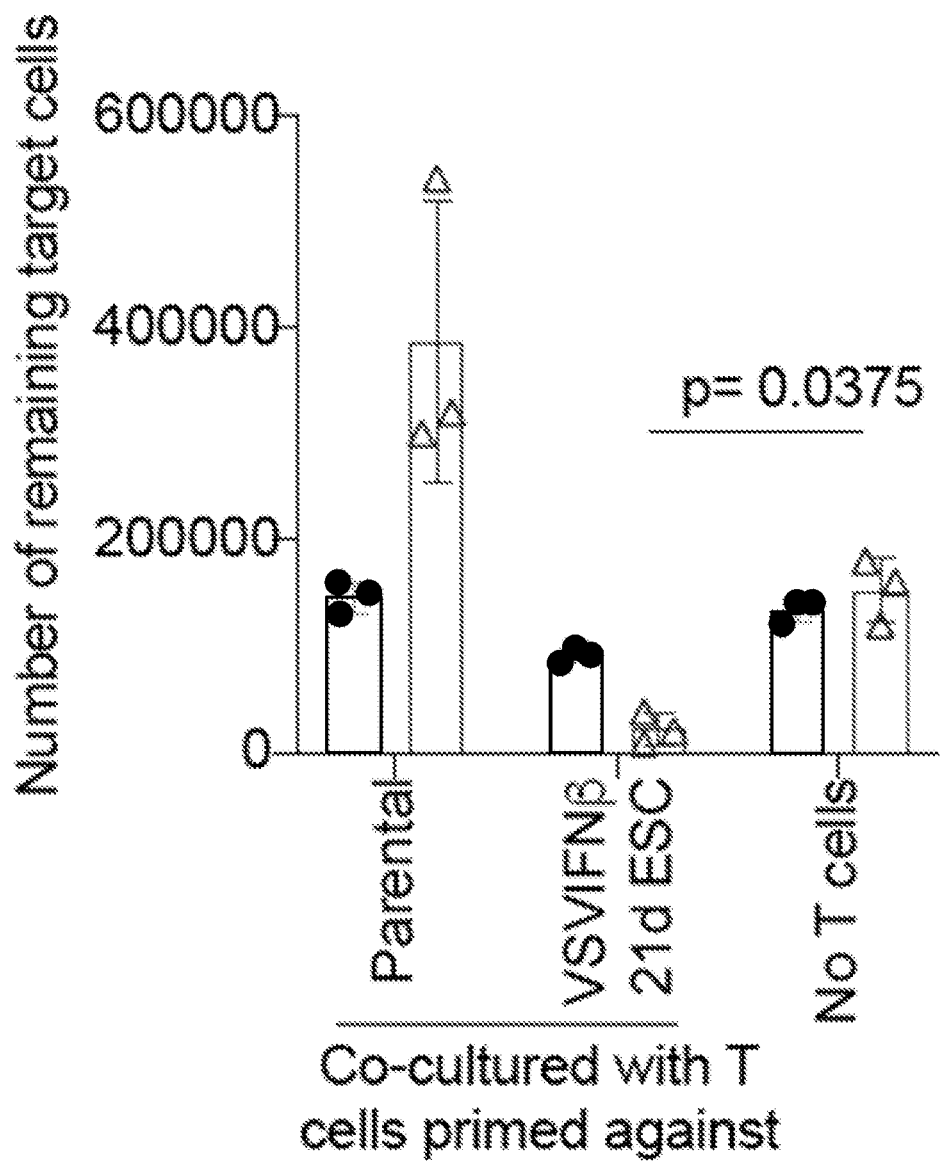
Figure 6D:
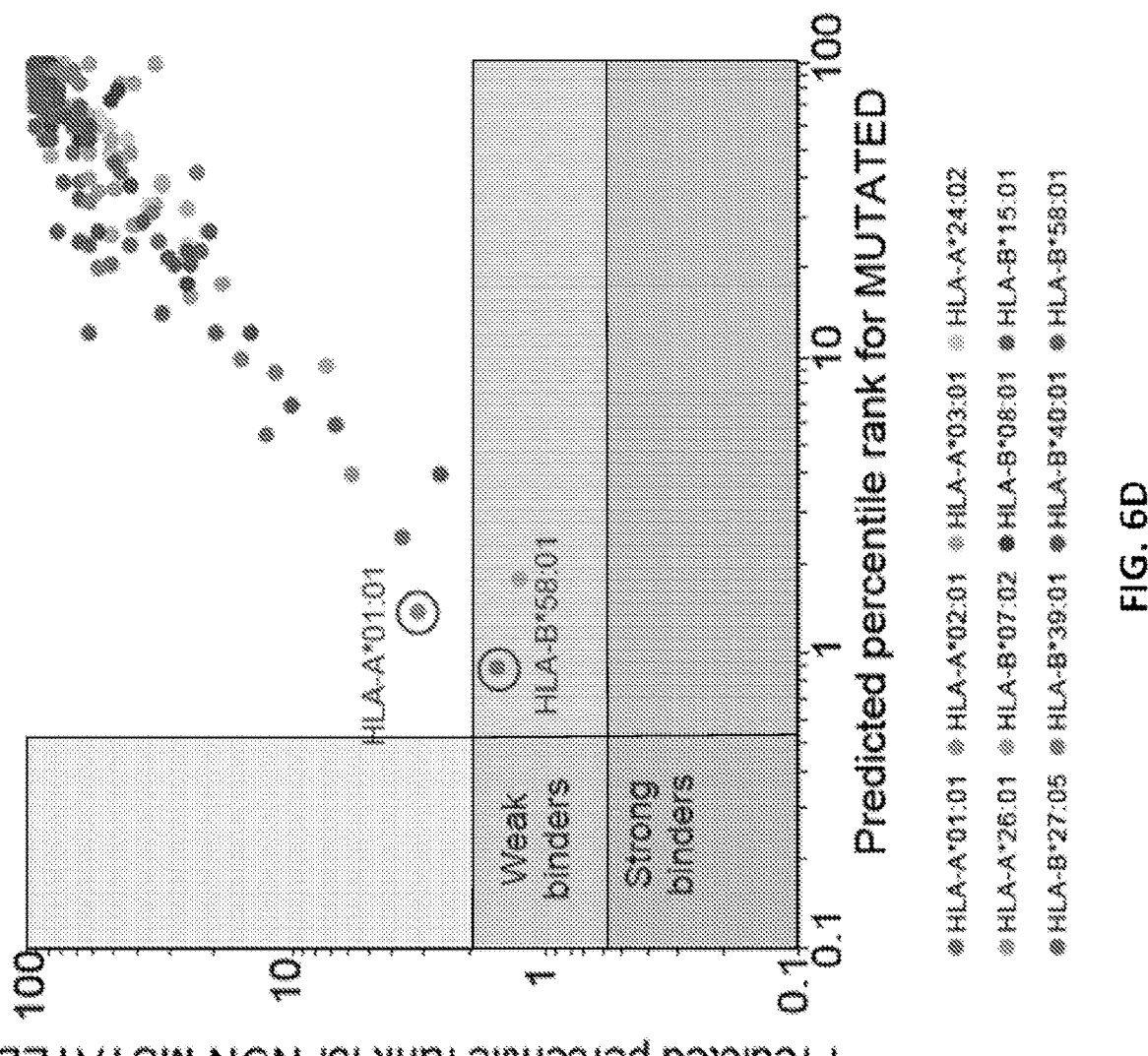
Figure 6E:
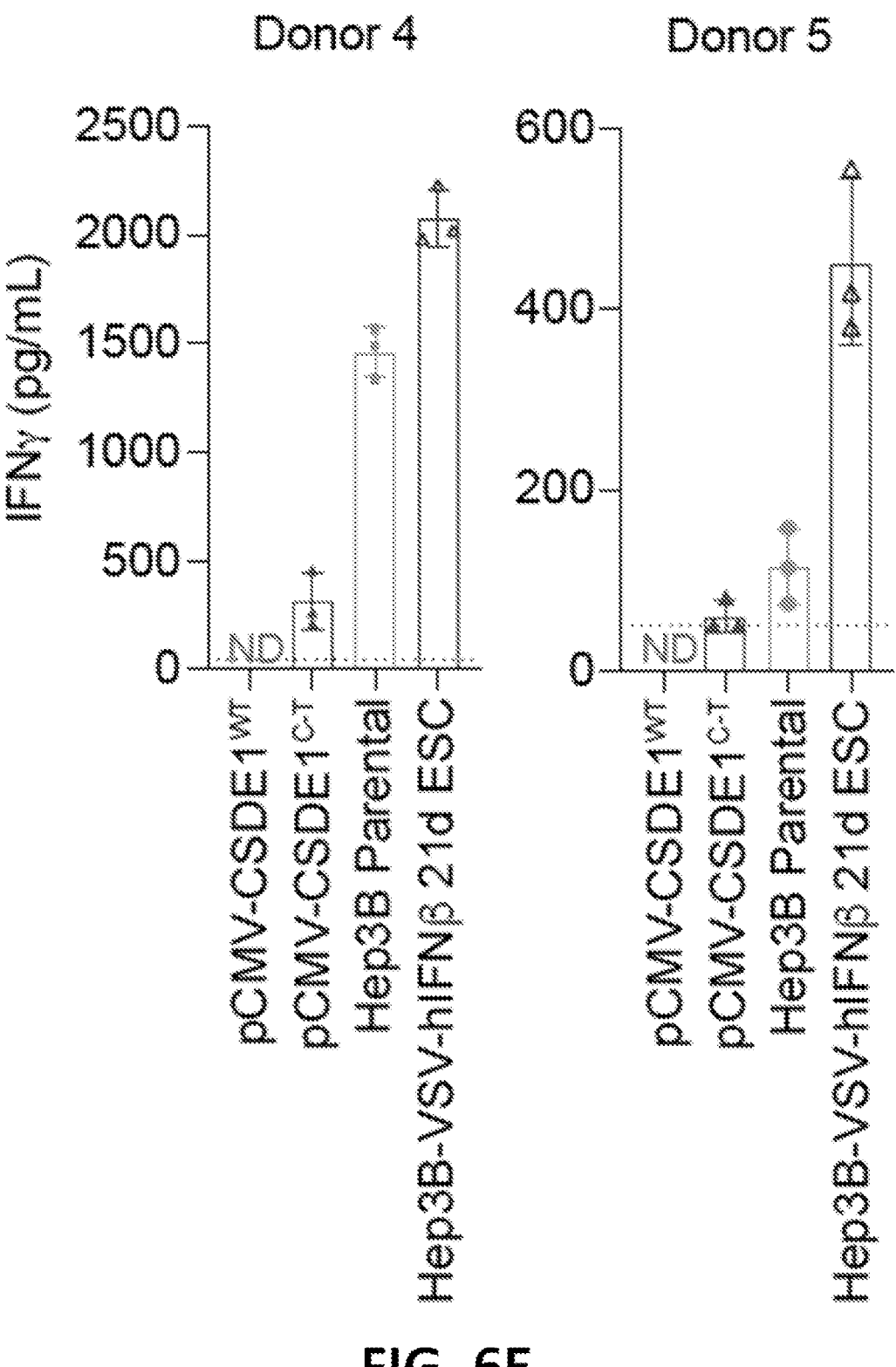

The following was performed to determine whether CSDE1P5S, and other undefined EATA, would be immunogenic for human T cells. In three separate co-cultures, CD3/CD28-activated human CD3+ T cells had different baseline reactivity against Hep3B targets, reflecting different alloreactivities (Driscoll et al., Nat. Comm., 11(1):790 (2020); Shim et al., Mol. Ther., 25(4):962-75 (2017); Errington et al., Gene Ther., 13:138-49 (2006); Merrick et al., Br. J. Cancer, 92(8):1450-8 (2005); and Ilett et al., Gene Ther., 24(1):21-30 (2017)) (FIGS. 6A and 6B). Nonetheless, both APOBEC3B-mutated Hep3B targets, as well as CSDE1$^{C\text{-}T}$-expressing Hep3B-VSV-hIFNβ-ESC cells (FIG. 1I), were significantly more immunogenic than Hep3BP across all three donors (FIG. 6B). Immunogenicity was significantly reduced by knockdown of CSDE1 (Martinez-Useros et al., J. Clin. Med., 8(4):560 (2019)) (FIG. 6B), suggesting that neo-antigenesis of hCSDE1$^{P5S}$ may serve as an EATA. T cells expanded against Hep3B were unable to kill either Hep3B, or Hep3B-VSV-IFNβ-ESC, targets (FIG. 6C). In contrast, T cells expanded against Hep3B-VSV-IFNβ-ESC cells showed significant cytotoxicity against Hep3B-VSV-IFNβ-ESC targets (FIG. 6C), and some cytotoxicity against Hep3B, suggesting that some T cell responses against EATA may be heteroclitic. Of all possible 8-, 9-, 10-, and 11-mers with the Proline-Serine mutation at amino acid position 5, the 9-mer, MSFDSNLLH (SEQ ID NO:18), was predicted to have weak binding affinity for HLA-A*01:01, HLA-A*03:01, and HLA-B*58:01 (FIG. 6D), which, for HLA-A*01:01 and HLA-B*58:01, was predicted to be stronger than the wild-type epitope MSFDPNLLH (SEQ ID NO:17). T cells from one additional donor could be primed by CSDE1$^{C\text{-}T}$-transfected DC, but not by CSDE1$^{WT}$-transfected DC, to recognize the CSDE1$^{P5S}$EATA. However, T cells from a second donor did not recognize either wild-type, or mutated, CSDE1 (FIG. 6E). Both donors 4 and 5 exhibited high level T cell priming against Hep3B-VSV-IFNβ-ESC cells compared to Hep3B (FIGS. 6E and 6B). Thus, escape from VSV-hIFNβ generated cells that were consistently more immunogenic than parental in both human and murine contexts.

Discussion

The results provided herein demonstrate that neo-antigenesis resulting from high mutational plasticity of tumors, which also facilitates treatment escape, can be exploited to impose a powerful immunotherapy against escape tumors as they are forced to evolve in response to frontline treatment. By targeting a predictable and reproducible mutation induced with high clonality within treatment escape tumors, the efficacy of VSV-IFNβ viro-immunotherapy can be significantly improved over that obtained with the virotherapy alone.

Escape from treatments such as oncolytic virotherapy can occur for multiple reasons, involving not only tumor cell mutational plasticity but also other mechanisms including a simple lack of efficient infection, HLA incompatibility with EATA, immune suppression, and anti-viral tumor microenvironments. However, mutational pathways, such as APOBEC3B, induced by frontline treatment with a clinical agent VSV-IFNβ were shown to lead to the emergence of escape variants carrying a very specific mutation that is heavily selected for at high frequency (FIG. 1). It was reasoned that such mutations may be in genes/proteins that mediate escape from innate, and adaptive, immune-mediated mechanisms of tumor clearance induced by VSV infection and/or may allow infected cells to down regulate critical steps in viral replication and thereby escape oncolysis.

Across species and tumors, knockdown of CSDE1 significantly decreased VSV replication, whilst its overexpression enhanced virus replication (FIGS. 2 and 3). Overexpression of CSDE1$^{P5S}$ also significantly decreased VSV replication (FIGS. 2 and 3), despite intact endogenous CSDE1$^{WT}$ protein. CSDE1 expressed from VSV (VSV-IFNβ-CSDE1$^{WT}$) enhanced replication in vitro and in vivo (FIGS. 3B and 4G), reduced escape (FIG. 3C), inhibited evolution of the escape-promoting CSDE1$^{C\text{-}T}$ mutation (FIG. 3D), and was significantly more effective than a current clinical agent VSV-IFNβ (FIGS. 4E and 4F). Overall, these results demonstrate that CSDE1 is a major positive regulator of VSV replication, and that CSDE1$^{P5S}$ acts as a dominant negative inhibitor to facilitate escape from oncolysis. These results also demonstrate that VSV-IFNβ-CSDE1 can be used as a clinical agent beyond VSV-IFNβ.

VSV expressing IFNβ was developed to increase anti-viral safety and anti-tumor immunogenicity (Willmon et al., *Cancer Res.*, 69(19):7713-20 (2009); and Jenks et al., *Human Gene Ther.*, 21:451-62 (2010)). However, addition of IFNβ unexpectedly increased escape through increased APOBEC3B, resulting in enhanced clonality of CSDE1$^{C-T}$ compared to VSV-GFP-ESC cells (FIG. 1). Although this was an unexpected byproduct of inclusion of IFNβ into the virus, expression of the highly selected CSDE1$^{C-T}$ mutation in escape cells presented an opportunity that can be exploited as described herein through targeting of this escape-induced mutation. Thus, since CSDE1$^{C-T}$ encodes a heteroclitic neo-epitope in the C57Bl/6 model (FIG. 4B), it was reasoned that, by forcing evolution of tumors to express CSDE1$^{C-T}$ through virotherapy (neo-antigenesis), escape variants could be ambushed by T cell responses against this discovered and consistently occurring CSDE1$^{P5S}$ EATA. VSV is an excellent platform for vaccination against tumor antigens (Diaz et al., *Cancer Res.*, 67:2840-8 (2007); Durham et al., *Mol. Ther.*, 25(8):1917-32 (2017); Pulido et al., *Nat. Biotechnol.*, 30(4):337-43 (2012); Alonso-Camino et al., *Mol. Ther.*, 22(11):1936-48 (2014); Kottke et al., *Nature Med.*, 2011:854-9 (2011); Janette et al., *Mol. Ther.*, 22(6): 1198-210 (2014); Bridle et al., *Mol. Ther.*, 17:1814-21 (2009); and Wongthida et al., *Human Gene Ther.*, 22:1343-53 (2011)) and was used as described herein to co-express CSDE1$^{C-T}$ from VSV-IFNβ to prime escape-specific T cell responses. VSV-IFNβ-CSDE1$^{C-T}$, replicated significantly less well than VSV-IFNβ or VSV-IFNβ-CSDE1$^{WT}$ (FIGS. 3B and 4G), but induced potent T cell responses against the CSDE1$^{P5S}$ EATA (FIG. 4B), which completely prevented escape (FIG. 4F). Although VSV-mIFNβ-CSDE1$^{WT}$ was a significantly better oncolytic than VSV-IFNβ (FIGS. 3B, 3C, 4F, and 4G), it did not generate anti-CSDE1$^{WT}$, or anti-CSDE1$^{P5S}$, T cell responses (FIG. 4B), it suppressed evolution of the CSDE1$^{P5S}$ immunogen in escaping cells (FIG. 3D), and it was not as effective as VSV-IFNβ-CSDE1$^{C-T}$ in achieving tumor treatment/cures (FIG. 4F). Thus, the therapeutic value of T cell control of emerging escape variants outweighed the loss of oncolytic potency of VSV-IFNβ-CSDE1$^{C-T}$ (FIG. 4F).

Figure 1J:
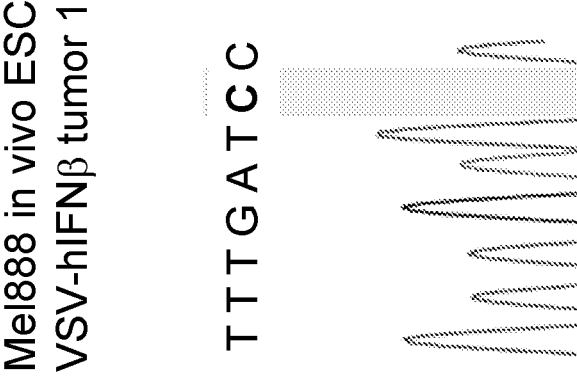

VSV-IFNβ-ESC tumors in vivo rarely contained a completely homogenous population of CSDE1$^{C-T}$ mutant tumor cells (FIG. 1J). Therefore, the heteroclitic anti-CSDE1$^{P5S}$ T cell responses (FIG. 4B) probably contributed a significant bystander effect against tumor cells that do not become infected, that escape direct oncolysis or innate immune clearance, or that do not evolve the CSDE1$^{C-T}$ mutation. Thus, it may be that intra-tumoral IL-12 (FIG. 4C), which correlated with anti-CSDE1$^{P5S}$ T cell responses (FIG. 4B), reflects T cell killing of both CSDE1$^{P5S}$ positive tumor cells and CSDE1$^{WT}$ cells through the generation of heteroclitic T cell responses (FIG. 4F). DC-CSDE1$^{C-T}$, with intra-tumoral VSV-IFNβ+ anti-PD-1, was not as effective as when the neo-antigen was expressed using the virus (FIG. 5C) and was associated with lower intra-tumoral IL-12 (FIGS. 4C and 5C). These results are consistent with a model in which intra-tumoral VSV-IFNβ-CSDE1$^{C-T}$ provides both high levels of inflammation (TNF-α in all VSV-injected tumors, FIGS. 4D and 5D) to enhance trafficking of anti-CSDE1$^{P5S}$- specific T cells. Simultaneously, VSV-IFNβ-CSDE1$^{C-T}$ also provides high concentrations of target antigen (CSDE1$^{P5S}$) (reflected by IL-12 only in VSV-IFN-β-CSDE1$^{C-T}$-injected tumors, FIG. 4C), which are lacking with i.p. DC and intra-tumoral VSV-IFNβ.

Human VSV-hIFNβ-ESC tumor cells also were significantly more immunogenic than untreated cells (FIG. 6), implying neo-antigenesis of EATA. These could include CSDE1$^{C-T}$, which was present at high clonality (FIG. 1I), knockdown of which significantly reduced T cell activation (FIG. 6B). Virotherapy with escape-targeting immunotherapy can include identifying HLA-/patient-specific EATA, such as CSDE1$^{P5S}$ where HLA compatibility is predicted (FIG. 6D), or the simultaneous targeting of multiple (unidentified) EATAs, for example, using VSV-expressed cDNA libraries derived from treatment-escape tumors.

In summary, the genetic plasticity of tumors was exploited by using oncolytic virotherapy to drive them into an escape phenotype so that they could then be ambushed by vaccination against a predictably arising EATA. This approach can be applied across a range of different frontline therapies that are potent enough to drive tumor cell mutation/evolution, thereby inducing neo-antigenesis resulting in a novel immunopeptidome associated with acquired treatment resistance.

Example 2—Loss of Oncolytic Fitness Via Mutation of Target Tumor Cell Genome

Restoration of Oncolytic Fitness Through Mutation of VSV

Figure 9:
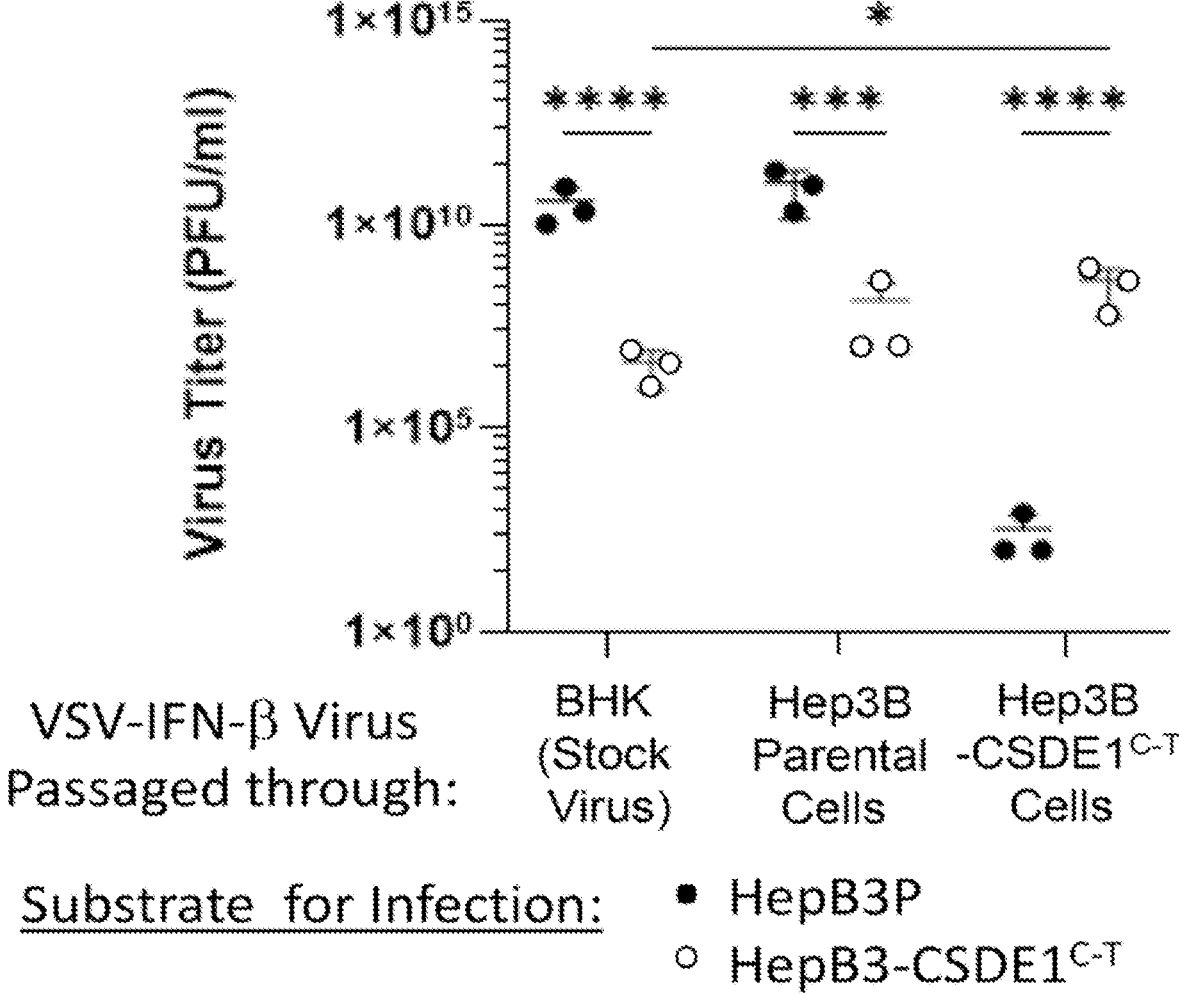
FIG. 9. Parental Hep3B cells, or pooled populations of Hep3B over-expressing mutant CSDE1$^{C-T}$ were infected with stock VSV-IFNβ (MOI 0.1) (3 wells/grp). 48 hours later, (Passage 1) supernatants were assayed for infectious titers on the same cells. Virus was recovered every 48 hours (P 2-5) and titered on Hep3B or on Hep3B-CSDE1$^{C-T}$ cells. *P≤0.05; ****P≤0.001.

Multiple passage of VSV-IFNβ through cells overexpressing wild type CSDE1$^{WT}$ (Hep3B or Mel888) significantly increased replication compared to passage through parental cells (FIG. 2F). Virus passaged 5 times through parental Hep3B replicated well on Hep3B but had orders of magnitude lower titers on Hep3B-CSDE1$^{P5S}$ (FIG. 9). Conversely, virus passaged 5 times through Hep3B-CSDE1$^{C-T}$ had very poor titers on Hep3B but replicated to near wild type levels on Hep3B-CSDE1$^{P5S}$ (FIG. 9). Thus, while cells mutate to escape oncolysis (CSDE$^{WT}$ to CSDE1$^{P5S}$), the virus can, with time, evolve to complement those mutations.

Figure 10A:
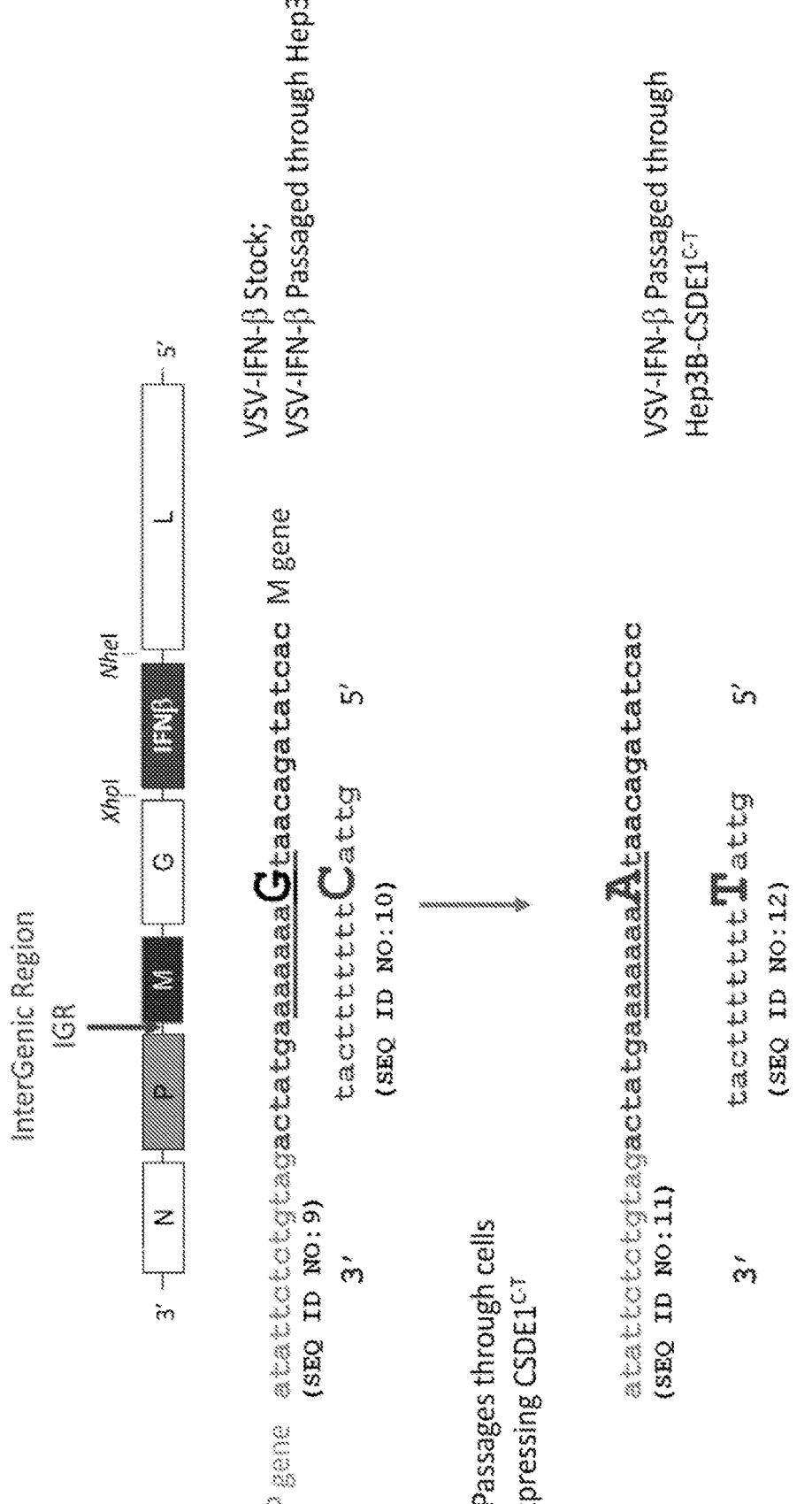
Figures 10B, 10C, 10D, 10E:
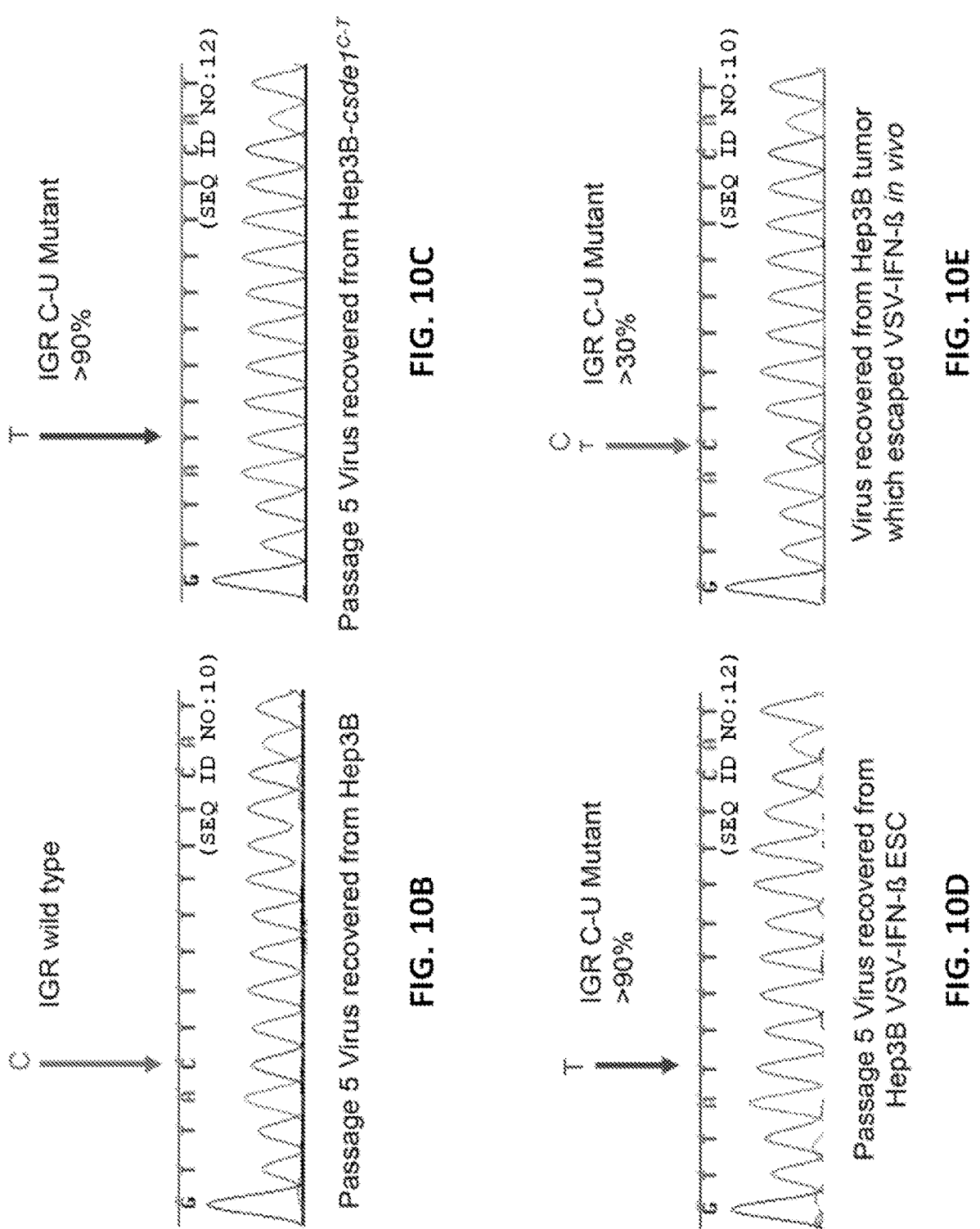

VSV-IFNβ passaged 5 times through Hep3B-CSDE1$^{P5S}$ (FIG. 9) contained low frequency mutations (<5%) throughout the genome, as determined by RNAseq. However, a single C-U mutation in the intergenic region (IGR) between the VSV P gene and the VSV M gene was present at ~100% frequency in the population; this mutation was undetectable in stock VSV-IFNβ or in VSV-IFNβ passaged 5 times through Hep3B (FIGS. 10A-10C). The same IGR P/M$^{C-U}$ mutation was recovered from VSV-IFNβ passaged 5 times through Mel888-CSDE1$^{P5S}$. Similarly, VSV-IFNβ passaged through Hep3B-21d-ESC cells was almost entirely mutant for IGR P/M$^{C-U}$ (FIG. 10D). Virus recovered from a Hep3B tumor in vivo which escaped VSV-IFNβ contained a mixed population of viruses (FIG. 10E).

CSDE1 Regulates Levels of Viral P and M mRNA

Figures 11E, 11F, 11G, 11H:
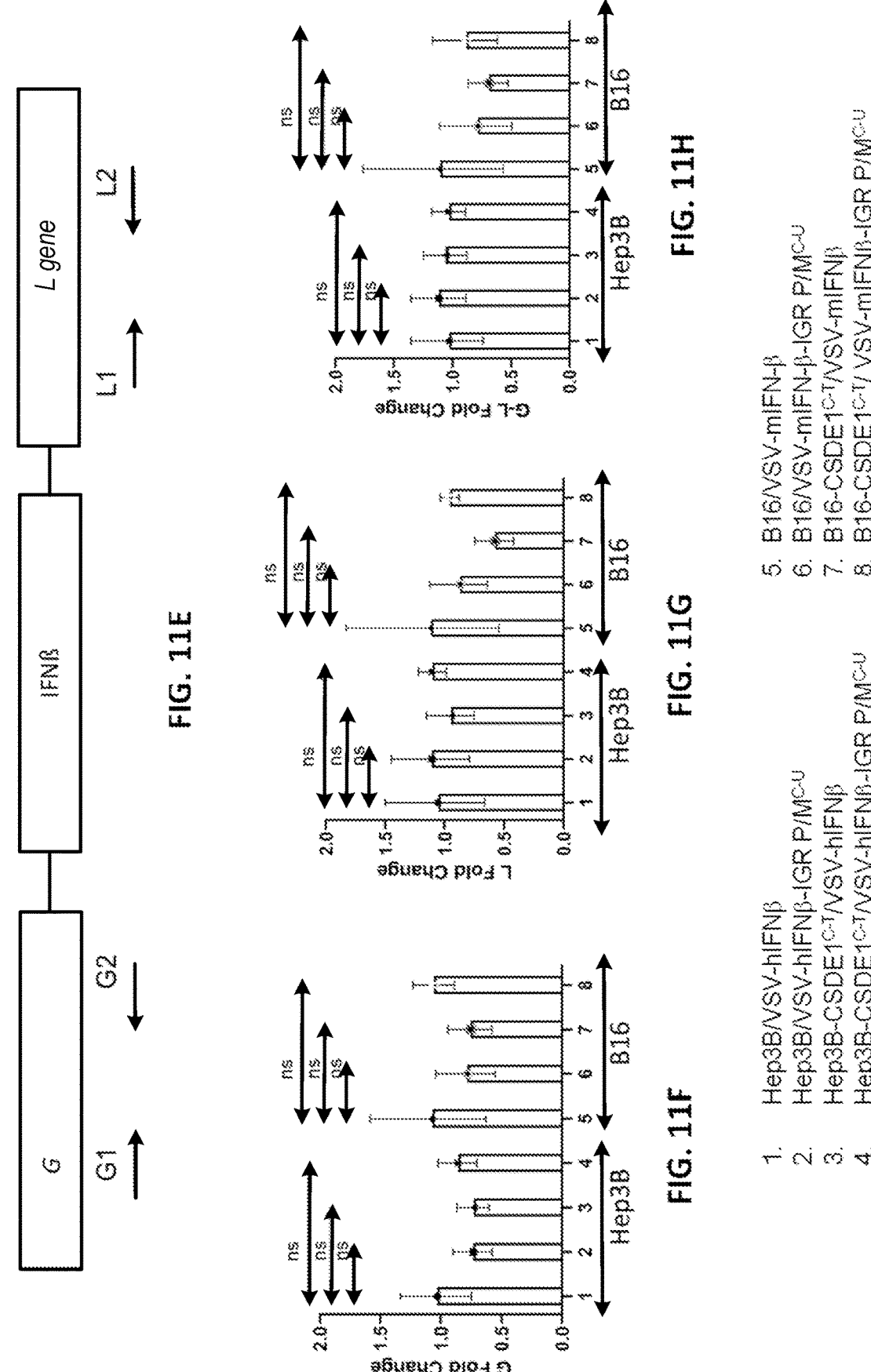
Figure 11I:
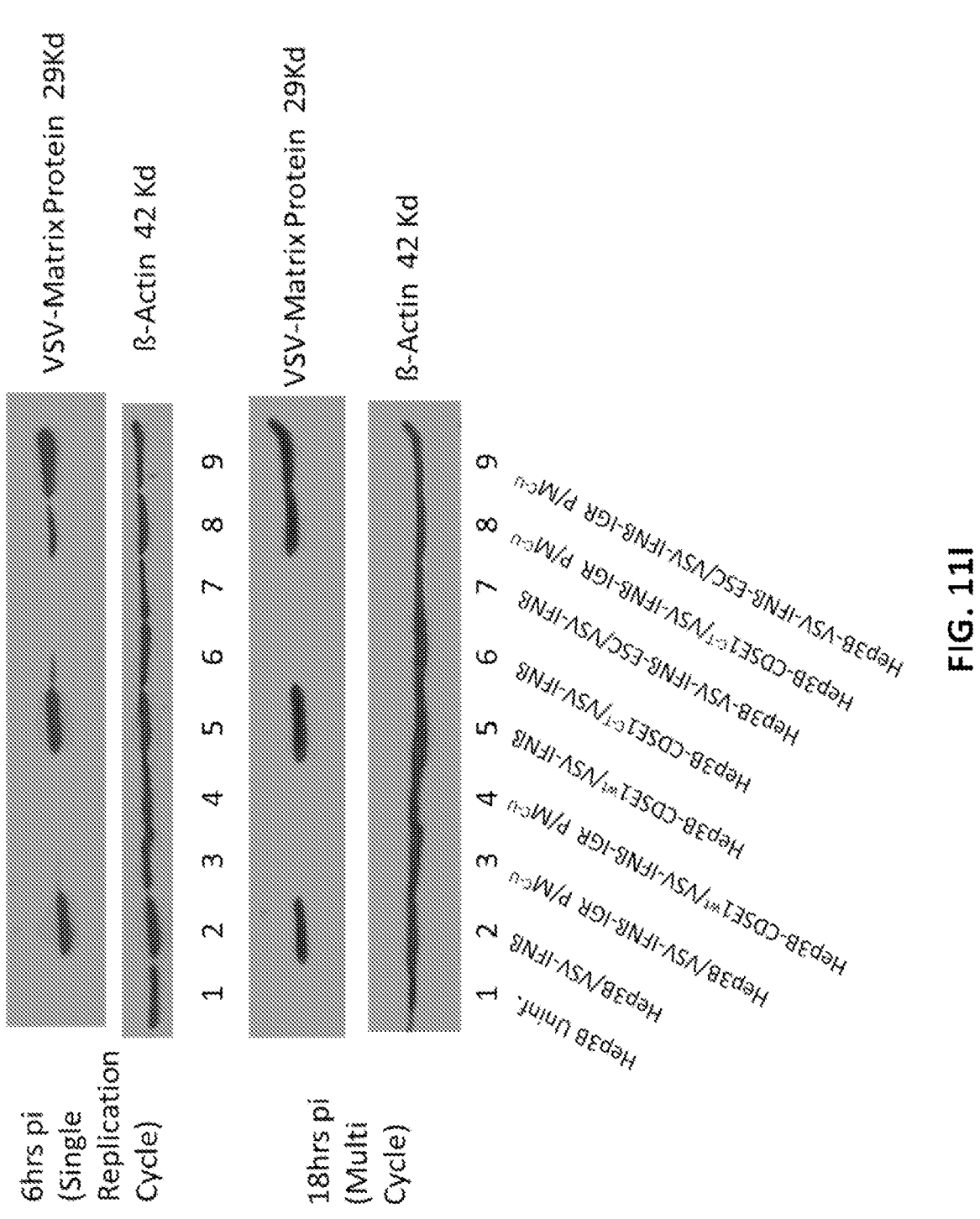

CSDE1, an RNA binding protein involved in translational control, binds RNA at a consensus site of 5'-(purine)(aagua)-3'. The IGR P/M$^{C-U}$ point mutation C-U on the −ye sense strand of the VSV genome corresponds to a G-A mutation on the +ve sense strand (FIG. 10A) precisely within an exact copy of the consensus CSDE1 binding site in the IGR between the P and M genes (FIG. 10A) (5'-aaaaa(aaGua)-3' to 5'-aaaaa(aaAua)-3'). This site in the IGR between the P and M genes is the only perfect CSDE1 consensus binding site in the VSV genome. This consensus site generally is present only in viral +ve sense transcripts, when the +ve sense genomic full-length strand is made during normal replication of the VSV genome (−ve to +ve RNA). The consensus site also exists if a sub-genomic, +ve strand P-M mRNA is made when the polymerase reads through the P/M IGR to make a unicistronic P-M mRNA. Such read-through is rare because P and M mRNAs usually are made by disengagement of polymerase at the P-M IGR, followed by re-initiation at the M gene. Thus, P, M, and P-M mRNAs from VSV-IFNβ or VSV-IFNβ-IGR P/M$^{C-U}$ were measured, on infection of B16 and Hep3BP, or B16-CSDE1$^{P5S}$ and Hep3B-CSDE1$^{P5S}$, cells within 6 hours of infection (early stage of replication) (FIGS. 11A-11I). When levels of RNA were normalized to those in cells infected by VSV-IFNβ, there were no significant changes in levels of P RNA in cells infected with VSV-IFNβ-IGR P/MC-U (FIG. 11B). In contrast to moderate or no changes in P RNA levels, levels of M RNA were very significantly decreased following infection of Hep3B-CSDE1$^{P5S}$ cells with VSV-IFNβ, or upon infection of Hep3BP cells with VSV-IFNβ-IGR P/M$^{C-U}$ (FIG. 11C). Infection of B16- or Hep3B-CSDE1$^{P5S}$ with VSV-IFNβ-IGR P/M$^{C-U}$ completely normalized levels of M RNA and protein, demonstrating that the negative effects of CSDE1$^{P5S}$ on transcription of viral M RNA were compensated by the presence of the IGR P/M$^{C-U}$ mutation in the viral genome (FIG. 11C). Levels of P-M bicistronic RNA were increased between 20- and 30-fold on infection of cells with VSV-IFNβ-IGR P/M$^{C-U}$, and between 10 and 30-fold in cells over-expressing CSDE1$^{P5S}$ infected with VSV-IFNβ (FIG. 11D). Again, infection of CSDE1$^{P5S}$ cells with VSV-IFNβ-IGR P/M$^{C-U}$ showed normalized P-M RNA levels seen (FIG. 11D). Relative levels of viral G and L RNA, as well as G-L RNA, were not significantly changed in cells infected with VSV-IFNβ-IGR P/M$^{C-U}$ or in CSDE1$^{P5S}$ cells infected with VSV-IFNβ, (FIGS. 11E-11H). These data suggested that CSDE1$^{P5S}$ interferes with early stage VSV replication, leading to loss of unicistronic M RNA and increased bicistronic P-M RNA. This hypothesis was strongly supported at the protein level as seen by Western Blot analysis for M protein (FIG. 11O. For example, while overexpression of CSDE1$^{P5S}$ highly inhibited levels of M protein from VSV-IFNβ (FIG. 11I, lanes 2 and 6), it rescued expression of M protein from the VSV-IFNβ-IGR P/M$^{C-U}$ virus (FIG. 11I, lane 8).

Figure 12A:
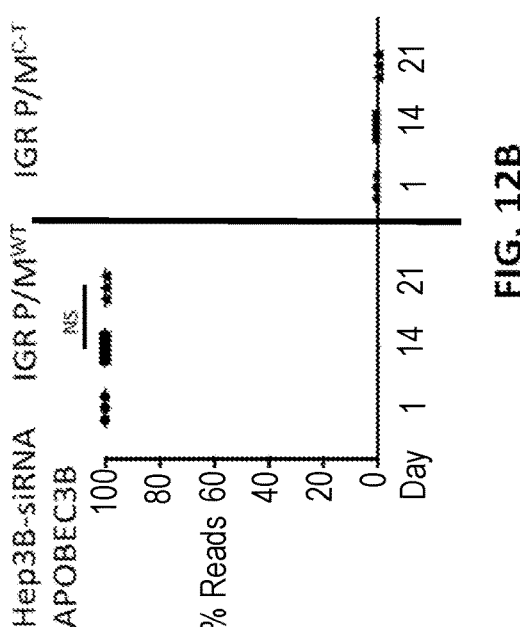
FIGS. 12A-12D. Evolution of the IGR P/M$^{C-U}$ mutation in VSV in response to cellular escape from VSV replication is dependent upon APOBEC3B. Hep3B cells engineered to express siRNA to APOBEC3B (FIG. 12B), the dominant negative mutant CSDE1$^{P5S}$ (FIG. 12C), both (FIG. 12D), or neither (FIG. 12A) were infected with VSV-IFNβ on day 0 (MOI 0.01) in triplicate wells. On days 1, 14, and 21, virus was harvested and viral genomes were analyzed by deep sequencing. Relative reads for the sequences of the wild type IGR between the P and M genes, compared to the mutated IGR P/M$^{C-U}$, are shown. *P≤0.05; **P≤0.01.
Figure 12B:
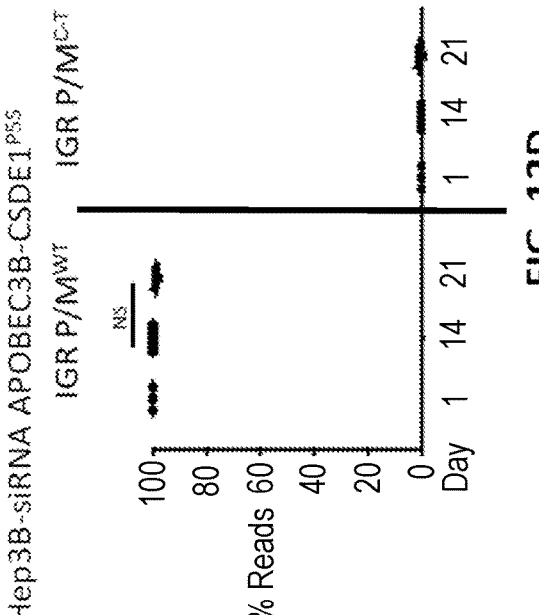
Figure 12C:
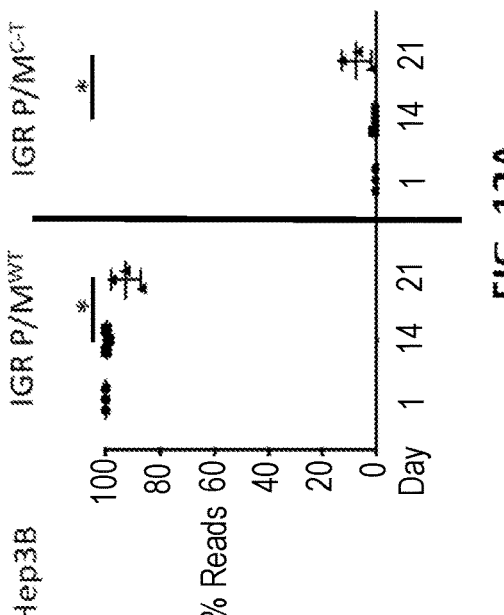
Figure 12D:
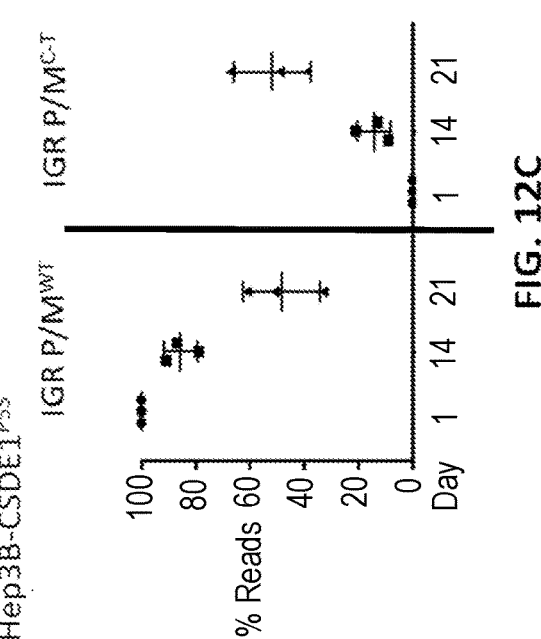

Further studies showed that as cells evolved to escape from VSV replication/lysis by selection of CSDE1$^{P5S}$, the proportion of VSV-IFNβ-IGR P/M$^{C-U}$ virus, while low, increased progressively (FIG. 12A). However, when target cells expressed reduced levels of APOBEC3B (by siRNA), emergence of VSV-IFNβ-IGR P/M$^{C-U}$ was undetectable by Deep Sequencing (FIG. 12B). Conversely, when target cells over-expressed CSDE1$^{P5S}$, emergence of VSV-IFNβ-IGR P/M$^{C-U}$ was significantly enhanced (FIG. 12C)—an effect that was abolished when APOBEC3B was knocked down (FIG. 12D). These data demonstrated that (1) VSV can, if given sufficient time, evolve in response to selective pressures that reduce viral replication/lysis, and (2) the IGR P/M$^{C-U}$ mutation in VSV that rescues replication in cells expressing CSDE1$^{P5S}$ is dependent upon APOBEC3B activity in the target cells.

CSDE1 Localizes to Cytoplasmic Replication Compartments

VSV sequesters its replication machinery into specialized non-membrane bound cytoplasmic compartments where RNA synthesis occurs. Experiments using simple immunofluorescence indicated that CSDE1 localizes to these cytoplasmic replication compartments in VSV infected cells (FIG. 13).

VSV-CSDE1 as an Oncolytic

VSV-CSDE1$^{WT}$ was validated by Western Blot for expression of CSDE1. BHK, B16, Hep3B and Mel888 cell lines were infected with VSV-GFP, VSV-hIFN-β, VSV-CSDE1$^{WT}$ or VSV-CSDE1$^{5P-S}$ (MOI 3; triplicate wells). After 48 hours, the virus was titered on BHK cells by plaque assay. These studies revealed that over-expression of CSDE1$^{WT}$ from VSV significantly enhanced replication compared to VSV-GFP, while virus-driven CSDE1$^{P5S}$ inhibited replication (FIG. 14A).

B16 or Hep3B cells were infected (MOI 0.01) with VSV-IFNβ, VSV-IFN-β-CSDE1$^{WT}$, or VSV-IFN-β-CSDE1$^{5P-S}$ (species matched IFNβ) for 21 days. Surviving cells were counted. In addition, Sanger sequencing of CSDE1 from surviving cells after infection with VSV-hIFNβ-CSDE1$^{WT}$ was conducted. These studies showed that infection with VSV-IFNβ-CSDE1$^{WT}$ significantly reduced both escape (FIG. 14B), and the escape-enabling CSDE1$^{C-T}$ mutation (~10-50% in FIG. 14C, compared to >90% in FIG. 1), compared to VSV-IFNβ. These data suggested that VSV-GFP/IFNβ-CSDE1$^{WT}$ is a significantly more effective oncolytic than parental VSV.

Vaccinating Potential of VSV-CSDE1$^{WT}$

Enhanced replication of VSV-CSDE1$^{WT}$ over VSV may significantly enhance immunogenicity of encoded foreign immunogens for vaccination against infectious agents, such as EBOLA or SARS-CoV-2. To test this, VSV expressing SPIKE, M, or N proteins of SARS-CoV-2, +/−IFNβ, were generated to induce T cell responses to support current antibody-based vaccines. The SPIKE of SARS-CoV-2 was codon optimized, truncated by deleting the ER targeting sequence to enhance Spike pseudotype morphogenesis, and cloned into the stable Prefusion conformation (introduction of 2 prolines in S2 with a furin cleavage mutation in the Receptor binding domain (RBD)) with a GFP-luciferase reporter. Spike replaced VSV-G and mediated infection of the Delta-G pseudotyped virus through the ACEII receptor of SARS-CoV-2. ACEII transgenic or C57BL/6 mice that were vaccinated with VSV expressing SARS-CoV-2 SPIKE (infectious agent vaccine) or hgp100 (anti-melanoma vaccine) showed a highly significant (p<0.001) increase in the frequency of anti-immunogen T cells induced by CSDE1$^{WT}$-overexpressing VSV compared to non-CSDE1$^{WT}$-expressing counterparts (FIGS. 15A and 15B), consistent with the hypothesis that enhanced replicative capacity of VSV expressing CSDE1$^{WT}$ enhances the immunogenicity of expressed antigens.

In summary, the studies described above demonstrated that in multiple cell types, (1) knockdown of CSDE1 decreases viral replication (e.g., VSV replication); (2) over-expression of CSDE1 enhances viral replication (e.g., VSV replication); (3) overexpression of CSDE1$^{P5S}$ decreases viral replication (e.g., VSV replication); (4) a compensatory C-U mutation in the P/M IGR correlates with forced evolution of VSV to replicate on cells overexpressing CSDE1$^{P5S}$; and (5) emergence of VSV-IFNβ-IGR P/M$^{C-U}$ in response to selection increases progressively with time, but lags behind cellular mutation of CSDE1$^{P5S}$ and is dependent upon APOBEC3B. These results demonstrate that CSDE1, not previously associated with VSV replication, is a critical mediator of the replication/oncolytic activity of VSV-IFNβ, that CSDE1$^{P5S}$ allows escape from VSV-IFNβ virotherapy, and that VSV can evolve compensatory mutations to recover its fitness in CSDE1$^{P5S}$ cells, of which the IGR P/M$^{C-U}$ mutation is a major driver.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises administering, to said mammal, (a) a replication-competent oncolytic virus and (b) a polypeptide comprising the amino acid sequence set forth in SEQ ID NO:1 or nucleic acid encoding said polypeptide, and wherein said cancer comprises melanoma or hepatocellular carcinoma.

2. The method of claim 1, wherein said mammal is a human.

3. The method of claim 1, wherein said virus is a vesicular stomatitis virus.

4. The method of claim 1, wherein said polypeptide is a full length CSDE1$^{P5S}$ polypeptide.

5. The method of claim 1, wherein said polypeptide comprises less than 100 amino acid residues.

6. The method of claim 1, wherein said polypeptide comprises less than 100 amino acid residues of a full length CSDE1$^{P5S}$ polypeptide.

7. The method of claim 1, wherein said polypeptide comprises a cell penetrating amino acid sequence.

8. The method of claim 1, wherein said method comprises administering said polypeptide.

9. The method of claim 1, wherein said method comprises administering said nucleic acid.

10. A replication-competent oncolytic virus comprising nucleic acid encoding the amino acid sequence set forth in SEQ ID NO:1 or comprising a nucleic acid sequence that is a template for said nucleic acid encoding the amino acid sequence set forth in SEQ ID NO:1.

11. The virus of claim 10, wherein said virus is selected from the group consisting of a vesicular stomatitis virus, an adenovirus, and a herpesvirus.

12. The virus of claim 10, wherein said nucleic acid encoding encodes a full length CSDE1$^{P5S}$ polypeptide.

13. The virus of claim 10, wherein said nucleic acid encodes a polypeptide that comprises less than 100 amino acid residues of a full length CSDE1$^{P5S}$ polypeptide.

14. A composition comprising (a) a substantially pure polypeptide comprising the amino acid sequence set forth in SEQ ID NO:1 and (b) an adjuvant.

15. A replication-competent vesicular stomatitis virus comprising an RNA molecule, wherein said RNA molecule comprises a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding the amino acid sequence set forth in SEQ ID NO:1, and a nucleic acid sequence that is a template for a positive sense transcript encoding a VSV L polypeptide, wherein said positive sense transcript encoding said VSV N polypeptide, said positive sense transcript encoding said VSV P polypeptide, said positive sense transcript encoding said VSV M polypeptide, said positive sense transcript encoding said VSV G polypeptide, and said VSV L polypeptide are each set forth within the nucleotide sequence of SEQ ID NO:16.

16. A composition comprising (a) the replication-competent vesicular stomatitis virus of claim 15 and (b) a biologically compatible solution or a pharmaceutically acceptable delivery vehicle.

17. A nucleic acid molecule comprising a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a VSV G polypeptide, a nucleic acid sequence that is a template for a positive sense transcript encoding the amino acid sequence set forth in SEQ ID NO:1, and a nucleic acid sequence that is a template for a positive sense transcript encoding a VSV L polypeptide, wherein said positive sense transcript encoding said VSV N polypeptide, said positive sense transcript encoding said VSV P polypeptide, said positive sense transcript encoding said VSV M polypeptide, said positive sense transcript encoding said VSV G polypeptide, and said VSV L polypeptide are each set forth within the nucleotide sequence of SEQ ID NO:16.

* * * * *

SEQUENCE LISTING

```
<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Met Ser Phe Asp Ser Asn Leu Leu His
1               5

<210> SEQ ID NO 2
<211> LENGTH: 767
<212> TYPE: PRT
<213> ORGANISM: Homo sapiens

<400> SEQUENCE: 2

Met Ser Phe Asp Pro Asn Leu Leu His Asn Asn Gly His Asn Gly Tyr
1               5                   10                  15

Pro Asn Gly Thr Ser Ala Ala Leu Arg Glu Thr Gly Val Ile Glu Lys
            20                  25                  30

Leu Leu Thr Ser Tyr Gly Phe Ile Gln Cys Ser Glu Arg Gln Ala Arg
            35                  40                  45

Leu Phe Phe His Cys Ser Gln Tyr Asn Gly Asn Leu Gln Asp Leu Lys
        50                  55                  60

Val Gly Asp Asp Val Glu Phe Glu Val Ser Ser Asp Arg Arg Thr Gly
65                  70                  75                  80

Lys Pro Ile Ala Val Lys Leu Val Lys Ile Lys Gln Glu Ile Leu Pro
                85                  90                  95

Glu Glu Arg Met Asn Gly Gln Glu Val Phe Tyr Leu Thr Tyr Thr Pro
            100                 105                 110

Glu Asp Val Glu Gly Asn Val Gln Leu Glu Thr Gly Asp Lys Ile Asn
        115                 120                 125

Phe Val Ile Asp Asn Asn Lys His Thr Gly Ala Val Ser Ala Arg Asn
        130                 135                 140

Ile Met Leu Leu Lys Lys Lys Gln Ala Arg Cys Gln Gly Val Val Cys
145                 150                 155                 160

Ala Met Lys Glu Ala Phe Gly Phe Ile Glu Arg Gly Asp Val Val Lys
                165                 170                 175

Glu Ile Phe Phe His Tyr Ser Glu Phe Lys Gly Asp Leu Glu Thr Leu
            180                 185                 190

Gln Pro Gly Asp Asp Val Glu Phe Thr Ile Lys Asp Arg Asn Gly Lys
            195                 200                 205

Glu Val Ala Thr Asp Val Arg Leu Leu Pro Gln Gly Thr Val Ile Phe
        210                 215                 220

Glu Asp Ile Ser Ile Glu His Phe Glu Gly Thr Val Thr Lys Val Ile
225                 230                 235                 240

Pro Lys Val Pro Ser Lys Asn Gln Asn Asp Pro Leu Pro Gly Arg Ile
                245                 250                 255
```

-continued

```
Lys Val Asp Phe Val Ile Pro Lys Glu Leu Pro Phe Gly Asp Lys Asp
            260                 265                 270

Thr Lys Ser Lys Val Thr Leu Leu Glu Gly Asp His Val Arg Phe Asn
            275                 280                 285

Ile Ser Thr Asp Arg Arg Asp Lys Leu Glu Arg Ala Thr Asn Ile Glu
        290                 295                 300

Val Leu Ser Asn Thr Phe Gln Phe Thr Asn Glu Ala Arg Glu Met Gly
305                 310                 315                 320

Val Ile Ala Ala Met Arg Asp Gly Phe Gly Phe Ile Lys Cys Val Asp
                325                 330                 335

Arg Asp Val Arg Met Phe Phe His Phe Ser Glu Ile Leu Asp Gly Asn
                340                 345                 350

Gln Leu His Ile Ala Asp Glu Val Glu Phe Thr Val Val Pro Asp Met
            355                 360                 365

Leu Ser Ala Gln Arg Asn His Ala Ile Arg Ile Lys Lys Leu Pro Lys
            370                 375                 380

Gly Thr Val Ser Phe His Ser His Ser Asp His Arg Phe Leu Gly Thr
385                 390                 395                 400

Val Glu Lys Glu Ala Thr Phe Ser Asn Pro Lys Thr Thr Ser Pro Asn
                405                 410                 415

Lys Gly Lys Glu Lys Glu Ala Glu Asp Gly Ile Ile Ala Tyr Asp Asp
                420                 425                 430

Cys Gly Val Lys Leu Thr Ile Ala Phe Gln Ala Lys Asp Val Glu Gly
                435                 440                 445

Ser Thr Ser Pro Gln Ile Gly Asp Lys Val Glu Phe Ser Ile Ser Asp
            450                 455                 460

Lys Gln Arg Pro Gly Gln Gln Val Ala Thr Cys Val Arg Leu Leu Gly
465                 470                 475                 480

Arg Asn Ser Asn Ser Lys Arg Leu Leu Gly Tyr Val Ala Thr Leu Lys
                485                 490                 495

Asp Asn Phe Gly Phe Ile Glu Thr Ala Asn His Asp Lys Glu Ile Phe
                500                 505                 510

Phe His Tyr Ser Glu Phe Ser Gly Asp Val Asp Ser Leu Glu Leu Gly
            515                 520                 525

Asp Met Val Glu Tyr Ser Leu Ser Lys Gly Lys Gly Asn Lys Val Ser
        530                 535                 540

Ala Glu Lys Val Asn Lys Thr His Ser Val Asn Gly Ile Thr Glu Glu
545                 550                 555                 560

Ala Asp Pro Thr Ile Tyr Ser Gly Lys Val Ile Arg Pro Leu Arg Ser
                565                 570                 575

Val Asp Pro Thr Gln Thr Glu Tyr Gln Gly Met Ile Glu Ile Val Glu
            580                 585                 590

Glu Gly Asp Met Lys Gly Glu Val Tyr Pro Phe Gly Ile Val Gly Met
            595                 600                 605

Ala Asn Lys Gly Asp Cys Leu Gln Lys Gly Glu Ser Val Lys Phe Gln
        610                 615                 620

Leu Cys Val Leu Gly Gln Asn Ala Gln Thr Met Ala Tyr Asn Ile Thr
625                 630                 635                 640

Pro Leu Arg Arg Ala Thr Val Glu Cys Val Lys Asp Gln Phe Gly Phe
                645                 650                 655

Ile Asn Tyr Glu Val Gly Asp Ser Lys Lys Leu Phe Phe His Val Lys
            660                 665                 670

Glu Val Gln Asp Gly Ile Glu Leu Gln Ala Gly Asp Glu Val Glu Phe
```

-continued

```
            675              680              685
Ser Val Ile Leu Asn Gln Arg Thr Gly Lys Cys Ser Ala Cys Asn Val
    690              695              700

Trp Arg Val Cys Glu Gly Pro Lys Ala Val Ala Ala Pro Arg Pro Asp
705              710              715              720

Arg Leu Val Asn Arg Leu Lys Asn Ile Thr Leu Asp Asp Ala Ser Ala
            725              730              735

Pro Arg Leu Met Val Leu Arg Gln Pro Arg Gly Pro Asp Asn Ser Met
            740              745              750

Gly Phe Gly Ala Glu Arg Lys Ile Arg Gln Ala Gly Val Ile Asp
        755              760              765

<210> SEQ ID NO 3
<211> LENGTH: 2396
<212> TYPE: DNA
<213> ORGANISM: Mus musculus

<400> SEQUENCE: 3
atgagctttg atccaaacct tctccacaac aatggacaca atgggtaccc caatggtact      60
tcagcagcac ttcgtgaaac tggggttatt gaaaaactct tgacctctta cggattcatt     120
cagtgttcag aacggcaagc tagactttc ttccactgtt cacaatataa tggcaacctc      180
caagacttaa aagtaggaga tgatgttgaa tttgaagtat catctgaccg gaggactggg     240
aaacctattg ctattaaatt ggtgaagata aaaccagaaa tacatcctga agaacgaatg     300
aacggacaag ttgtgtgcgc tgttcctcac aacttagaga gtaaatctcc agctgccccg     360
ggtcagagtc aacagggag tgtatgctac gaacgtaatg gggaagtatt ttatctgact      420
tacacctctg aagatgtgga aggggaatgtt cagctggaaa ctggagataa aattaacttt    480
gtaattgata acaataaaca cactggtgct gtaagtgctc gtaatattat gctgttgaaa     540
aagaagcagg ctcgctgtca aggagtagtt tgtgccatga aggaggcgtt tggctttatc     600
gaaagaggtg atgttgtaaa agagatattc tttcactata gtgaatttaa aggtgaccta     660
gaaaccctac agcctggaga tgacgtgaa ttcacaatca aggacagaaa tggtaaagaa      720
gttgcaacag atgtcagact attgcctcaa ggaacagtca ttttgaaga tatcagcatt      780 gaacattttg aaggaactgt aaccaaagtt atcccaaaag tacccagtaa aaaccagaat     840
gacccattgc aggacgaat caaagttgac tttgtgattc ctaaagaact cccctttgga      900
gacaaagaca caaatccaa agtgaccctg ctggaaggtg accatgttag gtttaatatt      960
tcaacagacc gacgtgacaa attggaacga gcaaccaaca tagaggttct atcaaataca    1020
tttcagttca ctaatgaagc cagagagatg ggtgtgattg ctgccatgag agatggtttt    1080
ggtttcatca gtgtgtgga tcgtgatgct cgtatgttct tccacttcag tgagattcta    1140
gatgggaacc agctccacat tgcagatgaa gtagagttta ctgtggttcc tgatatgctc    1200
tctgcccaaa gaaatcatgc tattaggatt aaaaaacttc ccaagggcac ggtttcattc    1260
cattcccatt cagatcatcg ttttctgggc accgtagaaa aagaagccac tttttccaat    1320
cctaaaacta caagcccaa taaaggcaaa gacaaggagg cagaagatgg cattatagct     1380
tatgacgact gtgggtgaa actgacgatt gcttttcaag ccaaggatgt ggaaggatct    1440
acttctcctc aaataggaga taaggttgaa tttagtatta gtgacaaaca gaggcctgga    1500
cagcagattg caacttgcgg agactttag gtcgtaattc taactccaaa cgtctcttgg     1560
gttatgtggc aactctgaaa gataattttg gatttatga aacagctaat catgataagg     1620
```

-continued

```
aaatattttt ccactatagt gagttctctg gtgatgttga tagcctggaa ctgggagaca    1680
tggttgaata cagcttgtcc aaaggcaaag gcaataaagt cagtgctgag aaagtaaaca    1740
aagcccactc agtgaatggc attactgagg aagctaatcc caccatctac tctggtaaag    1800
tcattcgccc tctgagaggt gttgatccaa cacagattga gtaccaagga atgattgaga    1860
ttgtggagga gggggatatg aaaggtgaag tgtatccttt tggcatagtt gggatggcca    1920
acaaagggga ttgcctacag aaaggggaga gtgtcaagtt ccagttgtgt gtacttggcc    1980
aaaatgcaca aactatggcc tacaacatca cacccttcg tagggctact gtggagtgtg    2040
tgaaagatca gtttggcttt attaactatg aagtaggaga tagcaagaag ctcttttcc    2100 atgtgaaaga agttcaggat ggcgttgagc tacaggcagg agatgaggtg gaattctcag    2160
tgatccttaa tcagcgcact gggaagtgca gtgcctgtaa tgtctggcga gtctgtgaag    2220
gccccaaagc tgttgcagct cctcgacctg accggttggt caatcgccta aagaacatca    2280
ccctggatga tgccagtgct ccacgtctaa tggttcttcg tcagccaagg ggaccagata    2340
actcaatggg atttggtgca gaaagaaaga tccgtcaagc tggtgtcatt gactaa       2396
```

<210> SEQ ID NO 4
<211> LENGTH: 13
<212> TYPE: PRT
<213> ORGANISM: Human immunodeficiency virus

<400> SEQUENCE: 4

```
Gly Arg Lys Lys Arg Arg Gln Arg Arg Pro Pro Gln
1               5                   10
```

<210> SEQ ID NO 5
<211> LENGTH: 16
<212> TYPE: PRT
<213> ORGANISM: Drosophila melanogaster

<400> SEQUENCE: 5

```
Arg Gln Ile Lys Ile Trp Phe Gln Asn Arg Arg Met Lys Trp Lys Lys
1               5                   10                  15
```

<210> SEQ ID NO 6
<211> LENGTH: 18
<212> TYPE: PRT
<213> ORGANISM: Mus musculus

<400> SEQUENCE: 6

```
Leu Leu Ile Ile Leu Arg Arg Arg Ile Arg Lys Gln Ala His Ala His
1               5                   10                  15

Ser Lys
```

<210> SEQ ID NO 7
<211> LENGTH: 22
<212> TYPE: DNA
<213> ORGANISM: Homo sapiens

<400> SEQUENCE: 7

```
atgagctttg atccaaacct tc                                               22
```

<210> SEQ ID NO 8
<211> LENGTH: 22
<212> TYPE: DNA
<213> ORGANISM: Homo sapiens

<400> SEQUENCE: 8

-continued atgagctttg attcaaacct tc                                                      22

<210> SEQ ID NO 9
<211> LENGTH: 40
<212> TYPE: DNA
<213> ORGANISM: Vesicular stomatitis virus

<400> SEQUENCE: 9
cactatagac aatgaaaaaa agtatcagat gtctcttata                                   40

<210> SEQ ID NO 10
<211> LENGTH: 15
<212> TYPE: DNA
<213> ORGANISM: Vesicular stomatitis virus

<400> SEQUENCE: 10
gttacttttt ttcat                                                             15

<210> SEQ ID NO 11
<211> LENGTH: 40
<212> TYPE: DNA
<213> ORGANISM: Vesicular stomatitis virus

<400> SEQUENCE: 11
cactatagac aataaaaaaa agtatcagat gtctcttata                                  40

<210> SEQ ID NO 12
<211> LENGTH: 15
<212> TYPE: DNA
<213> ORGANISM: Vesicular stomatitis virus
<220> FEATURE:
<221> NAME/KEY: mutation
<222> LOCATION: (1)..(15)
<223> OTHER INFORMATION: mutant

<400> SEQUENCE: 12
gttatttttt ttcat                                                             15

<210> SEQ ID NO 13
<211> LENGTH: 9
<212> TYPE: PRT
<213> ORGANISM: Homo sapiens

<400> SEQUENCE: 13

Lys Val Pro Arg Asn Gln Asp Trp Leu
1               5

<210> SEQ ID NO 14
<211> LENGTH: 8
<212> TYPE: PRT
<213> ORGANISM: Gallus gallus

<400> SEQUENCE: 14

Ser Ile Ile Asn Phe Glu Lys Leu
1               5

<210> SEQ ID NO 15
<211> LENGTH: 20
<212> TYPE: DNA
<213> ORGANISM: Artificial
<220> FEATURE:
<223> OTHER INFORMATION: synthetic oligonucleotide

<400> SEQUENCE: 15
tcacgaagtg ctgctgaagt                                                        20

<210> SEQ ID NO 16
<211> LENGTH: 13641
<212> TYPE: DNA
<213> ORGANISM: Artificial
<220> FEATURE:
<223> OTHER INFORMATION: synthetic oligonucleotide construct

<400> SEQUENCE: 16

```
acgaagacaa acaaaccatt attatcatta aaaggctcag gagaaacttt aacagtaatc        60
aaaatgtctg ttacagtcaa gagaatcatt gacaacacag tcgtagttcc aaaacttcct       120
gcaaatgagg atccagtgga ataccoggca gattacttca gaaaatcaaa ggagattcct       180
ctttacatca atactacaaa aagtttgtca gatctaagag gatatgtcta ccaaggcctc       240
aaatccggaa atgtatcaat catacatgtc aacagctact tgtatggagc attaaaggac       300
atccggggta agttggataa agattggtca agtttcggaa taaacatcgg gaaagcaggg       360
gatacaatcg gaatatttga ccttgtatcc ttgaaagccc tggacggcgt acttccagat       420
ggagtatcgg atgcttccag aaccagcgca gatgacaaat ggttgccttt gtatctactt       480
ggcttataca gagtgggcag aacacaaatg cctgaataca gaaaaaagct catggatggg       540
ctgacaaatc aatgcaaaat gatcaatgaa cagtttgaac ctcttgtgcc agaaggtcgt       600 gacattttg atgtgtgggg aaatgacagt aattacacaa aaattgtcgc tgcagtggac        660
atgttcttcc acatgttcaa aaaacatgaa tgtgcctcgt tcagatacgg aactattgtt       720
tccagattca aagattgtgc tgcattggca acatttggac acctctgcaa aataaccgga       780
atgtctacag aagatgtaac gacctggatc ttgaaccgag aagttgcaga tgaaatggtc       840
caaatgatgc ttccaggcca agaaattgac aaggccgatt catacatgcc ttatttgatc       900
gactttggat tgtcttctaa gtctccatat tcttccgtca aaaaccctgc cttccacttc       960
tgggggcaat tgacagctct tctgctcaga tccaccagag caaggaatgc ccgacagcct      1020
gatgacattg agtatacatc tcttactaca gcaggtttgt tgtacgctta tgcagtagga      1080
tcctctgccg acttggcaca acagttttgt gttggagata caaatacac tccagatgat       1140 agtaccggag gattgacgac taatgcaccg ccacaaggca gagatgtggt cgaatggctc      1200
ggatggtttg aagatcaaaa cagaaaaccg actcctgata tgatgcagta tgcgaaaaga      1260
gcagtcatgt cactgcaagg cctaagagag aagacaattg gcaagtatgc taagtcagaa      1320
tttgacaaat gaccctataa ttctcagatc acctattata tattatgcta catatgaaaa      1380
aaactaacag atatcatgga taatctcaca aaagttcgtg agtatctcaa gtcctattct      1440
cgtctggatc aggcggtagg agagatagat gagatcgaag cacaacgagc tgaaaagtcc      1500
aattatgagt tgttccaaga ggatggagtg aagagcata ctaagccctc ttattttcag       1560
gcagcagatg attctgacac agaatctgaa ccagaaattg aagacaatca aggcttgtat      1620
gcaccagatc agaagctga gcaagttgaa ggctttatac aggggccttt agatgactat       1680
gcagatgagg aagtggatgt tgtatttact tcggactgga aacagcctga gcttgaatct      1740
gacgagcatg aaaagacctt acggttgaca tcgccagagg gtttaagtgg agagcagaaa      1800
tcccagtggc tttcgacgat taaagcagtc gtgcaaagtg ccaaatactg gaatctggca      1860
gagtgcacat ttgaagcatc gggagaaggg gtcattatga aggagcgcca gataactccg      1920
gatgtatata aggtcactcc agtgatgaac acacatccgt cccaatcaga agcagtatca      1980
gatgtttggt ctctctcaaa gacatccatg actttccaac ccaagaaagc aagtcttcag      2040
```

-continued

```
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca   2340 ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga aacgtccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggactc tatcggccac ttcaaatgag   2940
ctagtctaac ttctagcttc tgaacaatcc ccggtttact cagtctcccc taattccagc   3000
ctctcgaaca actaatatcc tgtcttttct atccctatga aaaaaactaa cagagatcga   3060
tctgtttacg cgtcactatg aagtgccttt tgtacttagc cttttttattc attggggtga   3120 attgcaagtt caccatagtt tttccacaca accaaaaagg aaactggaaa aatgttcctt   3180
ctaattacca ttattgcccg tcaagctcag atttaaattg gcataatgac ttaataggca   3240
cagccttaca agtcaaaatg cccaagagtc acaaggctat tcaagcagac ggttggatgt   3300
gtcatgcttc caaatgggtc actacttgtg atttccgctg gtatggaccg aagtatataa   3360
cacattccat ccgatccttc actccatctg tagaacaatg caaggaaagc attgaacaaa   3420
cgaaacaagg aacttggctg aatccaggct ccctcctca aagttgtgga tatgcaactg   3480
tgacggatgc cgaagcagtg attgtccagg tgactcctca ccatgtgctg gttgatgaat   3540
acacaggaga atgggttgat tcacagttca tcaacggaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720
gaaaggaggg cacagggttc agaagtaact actttgctta tgaaactgga ggcaaggcct   3780
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg acccaatgg agttctgagg accagttcag   4260
gatataagtt tccttatac atgattggac atggtatgtt ggactccgat cttcatctta   4320
gctcaaaggc tcaggtgttc gaacatcctc acattcaaga cgctgcttcg caacttcctg   4380
atgatgagag tttatttttt ggtgatactg ggctatccaa aaatccaatc gagcttgtag   4440
```

```
aaggttggtt cagtagttgg aaaagctcta ttgcctcttt tttctttatc atagggttaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctcga gaattaattg ctaggtatga   4680
aaaaaactaa cagatatcac gctcgagatg agctttgatc caaaccttct ccacaacaat   4740
ggacacaatg ggtaccccaa tggtacttca gcagcacttc gtgaaactgg ggttattgaa   4800
aaactcttga cctcttacgg attcattcag tgttcagaac ggcaagctag acttttcttc   4860
cactgttcac aatataatgg caacctccaa gacttaaaag taggagatga tgttgaattt   4920
gaagtatcat ctgaccggag gactgggaaa cctattgcta ttaaattggt gaagataaaa   4980
ccagaaatac atcctgaaga acgaatgaac ggacaagttg tgtgcgctgt tcctcacaac   5040
ttagagagta aatctccagc tgccccgggt cagagtccaa cagggagtgt atgctacgaa   5100
cgtaatgggg aagtatttta tctgacttac acctctgaag atgtggaagg gaatgttcag   5160
ctggaaactg gagataaaat taactttgta attgataaca ataaacacac tggtgctgta   5220
agtgctcgta atattatgct gttgaaaaag aagcaggctc gctgtcaagg agtagtttgt   5280
gccatgaagg aggcgtttgg ctttatcgaa agaggtgatg ttgtaaaaga gatattcttt   5340
cactatagta aatttaaagg tgacctagaa accctacagc ctggagatga cgtggaattc   5400
acaatcaagg acagaaatgg taaagaagtt gcaacagatg tcagactatt gcctcaagga   5460
acagtcattt ttgaagatat cagcattgaa cattttgaag gaactgtaac caaagttatc   5520
ccaaaagtac ccagtaaaaa ccagaatgac ccattgccag gacgaatcaa agttgacttt   5580
gtgattccta agaacttcc ctttggagac aaagacacaa aatccaaagt gaccctgctg   5640
gaaggtgacc atgttaggtt taatatttca acagaccgac gtgacaaatt ggaacgagca   5700
accaacatag aggttctatc aaatacattt cagttcacta atgaagccag agagatgggt   5760
gtgattgctg ccatgagaga tggttttggt ttcatcaagt gtgtggatcg tgatgctcgt   5820
atgttcttcc acttcagtga gattctagat gggaaccagc tccacattgc agatgaagta   5880
gagtttactg tggttcctga tatgctctct gcccaaagaa atcatgctat taggattaaa   5940
aaacttccca agggcacggt ttcattccat tcccattcag atcatcgttt tctgggcacc   6000
gtagaaaaag aagccacttt ttccaatcct aaaactacaa gcccaaataa aggcaaagac   6060
aaggaggcag aagatggcat tatagcttat gacgactgtg gggtgaaact gacgattgct   6120
tttcaagcca aggatgtgga aggatctact tctcctcaaa taggagataa ggttgaattt   6180
agtattagtg acaaacagag gcctggacag cagattgcaa cttgcggaga cttttaggtc   6240
gtaattctaa ctccaaacgt ctcttgggtt atgtggcaac tctgaaagat aattttggat   6300
ttatagaaac agctaatcat gataaggaaa tattttttcca ctatagtgag ttctctggtg   6360
atgttgatag cctggaactg ggagacatgg ttgaatacag cttgtccaaa ggcaaaggca   6420
ataaagtcag tgctgagaaa gtaaacaaag cccactcagt gaatggcatt actgaggaag   6480
ctaatcccac catctactct ggtaaagtca ttcgccctct gagaggtgtt gatccaacac   6540
agattgagta ccaaggaatg attgagattg tggaggaggg ggatatgaaa ggtgaagtgt   6600
atccttttgg catagttggg atggccaaca aaggggattg cctacagaaa ggggagagtg   6660
tcaagttcca gttgtgtgta cttggccaaa atgcacaaac tatggcctac aacatcacac   6720
cccttcgtag ggctactgtg gagtgtgtga agatcagtt tggctttatt aactatgaag   6780
```

```
taggagatag caagaagctc tttttccatg tgaaagaagt tcaggatggc gttgagctac    6840
aggcaggaga tgaggtggaa ttctcagtga tccttaatca gcgcactggg aagtgcagtg    6900
cctgtaatgt ctggcgagtc tgtgaaggcc ccaaagctgt tgcagctcct cgacctgacc    6960
ggttggtcaa tcgcctaaag aacatcaccc tggatgatgc cagtgctcca cgtctaatgg    7020
ttcttcgtca gccaagggga ccagataact caatgggatt tggtgcagaa agaaagatcc    7080
gtcaagctgg tgtcattgac taagctagcc agattcttca tgtttggacc aaatcaactt    7140
gtgataccat gctcaaagag gcctcaatta tatttgagtt tttaattttt atgaaaaaaa    7200
ctaacagcaa tcatggaagt ccacgatttt gagaccgacg agttcaatga tttcaatgaa    7260
gatgactatg ccacaagaga attcctgaat cccgatgagc gcatgacgta cttgaatcat    7320
gctgattaca acctgaattc tcctctaatt agtgatgata ttgacaattt aatcaggaaa    7380
ttcaattctc ttccaattcc ctcgatgtgg gatagtaaga actgggatgg agttcttgag    7440
atgttaacgt catgtcaagc caatcccatc ccaacatctc agatgcataa atggatggga    7500
agttggttaa tgtctgataa tcatgatgcc agtcaagggt atagtttttt acatgaagtg    7560
gacaaagagg cagaaataac atttgacgtg gtggagacct tcatccgcgg ctggggcaac    7620
aaaccaattg aatacatcaa aaaggaaaga tggactgact cattcaaaat tctcgcttat    7680
ttgtgtcaaa agttttttgga cttacacaag ttgacattaa tcttaaatgc tgtctctgag    7740
gtggaattgc tcaacttggc gaggactttc aaaggcaaag tcagaagaag ttctcatgga    7800
acgaacatat gcaggattag ggttcccagc ttgggtccta cttttatttc agaaggatgg    7860
gcttacttca agaaacttga tattctaatg gaccgaaact ttctgttaat ggtcaaagat    7920
gtgattatag ggaggatgca aacggtgcta tccatggtat gtagaataga caacctgttc    7980
tcagagcaag acatcttctc ccttctaaat atctacagaa ttggagataa aattgtggag    8040
aggcagggaa attttttctta tgacttgatt aaaatggtgg aaccgatatg caacttgaag    8100
ctgatgaaat tagcaagaga atcaaggcct ttagtcccac aattccctca tttttgaaaat    8160 catatcaaga cttctgttga tgaaggggca aaaattgacc gaggtataag attcctccat    8220
gatcagataa tgagtgtgaa aacagtggat ctcacactgg tgatttatgg atcgttcaga    8280
cattggggtc atccttttat agattattac actggactag aaaaattaca ttcccaagta    8340
accatgaaga aagatattga tgtgtcatat gcaaaagcac ttgcaagtga tttagctcgg    8400
attgttctat ttcaacagtt caatgatcat aaaaagtggt tcgtgaatgg agacttgctc    8460
cctcatgatc atccctttaa aagtcatgtt aaagaaaata catggcccac agctgctcaa    8520
gttcaagatt ttggagataa atggcatgaa cttccgctga ttaaatgttt tgaaataccc    8580
gacttactag acccatcgat aatatactct gacaaaagtc attcaatgaa taggtcagag    8640
gtgttgaaac atgtccgaat gaatccgaac actcctatcc ctagtaaaaa ggtgttgcag    8700
actatgttgg acacaaaggc taccaattgg aaagaatttc ttaaagagat tgatgagaag    8760
ggcttagatg atgatgatct aattattggt cttaaaggaa aggagaggga actgaagttg    8820
gcaggtagat ttttctccct aatgtcttgg aaattgcgag aatactttgt aattaccgaa    8880
tatttgataa agactcattt cgtccctatg tttaaaggcc tgacaatggc ggacgatcta    8940
actgcagtca ttaaaaagat gttagattcc tcatccggcc aaggattgaa gtcatatgag    9000
gcaatttgca tagccaatca cattgattac gaaaaatgga ataaccacca aaggaagtta    9060
tcaaacggcc cagtgttccg agttatgggc cagttcttag gttatccatc cttaatcgag    9120
agaactcatg aatttttttga gaaaagtctt atatactaca atggaagacc agacttgatg    9180
```

-continued

```
cgtgttcaca acaacacact gatcaattca acctcccaac gagtttgttg gcaaggacaa   9240
gagggtggac tggaaggtct acggcaaaaa ggatggagta tcctcaatct actggttatt   9300
caaagagagg ctaaaatcag aaacactgct gtcaaagtct tggcacaagg tgataatcaa   9360
gttatttgca cacagtataa aacgaagaaa tcgagaaacg ttgtagaatt acagggtgct   9420
ctcaatcaaa tggtttctaa taatgagaaa attatgactg caatcaaaat agggacaggg   9480
aagttaggac ttttgataaa tgacgatgag actatgcaat ctgcagatta cttgaattat   9540
ggaaaaatac cgattttccg tggagtgatt agagggttag agaccaagag atggtcacga   9600
gtgacttgtg tcaccaatga ccaaataccc acttgtgcta atataatgag ctcagtttcc   9660
acaaatgctc tcaccgtagc tcattttgct gagaacccaa tcaatgccat gatacagtac   9720
aattattttg ggacatttgc tagactcttg ttgatgatgc atgatcctgc tcttcgtcaa   9780
tcattgtatg aagttcaaga taagataccg ggcttgcaca gttctacttt caaatacgcc   9840
atgttgtatt tggacccttc cattggagga gtgtcgggca tgtctttgtc caggtttttg   9900
attagagcct tcccagatcc cgtaacagaa agtctctcat tctggagatt catccatgta   9960
catgctcgaa gtgagcatct gaaggagatg agtgcagtat ttggaaaccc cgagatagcc  10020
aagtttcgaa taactcacat agacaagcta gtagaagatc caacctctct gaacatcgct  10080
atgggaatga gtccagcgaa cttgttaaag actgaggtta aaaaatgctt aatcgaatca  10140
agacaaacca tcaggaacca ggtgattaag gatgcaacca tatatttgta tcatgaagag  10200
gatcggctca gaagtttctt atggtcaata aatcctctgt tccctagatt tttaagtgaa  10260
ttcaaatcag gcactttttt gggagtcgca gacgggctca tcagtctatt tcaaaattct  10320
cgtactattc ggaactcctt taagaaaaag tatcataggg aattggatga tttgattgtg  10380
aggagtgagg tatcctcttt gacacattta gggaaacttc atttgagaag gggatcatgt  10440
aaaatgtgga catgttcagc tactcatgct gacacattaa gatacaaatc ctggggccgt  10500
acagttattg ggacaactgt accccatcca ttagaaatgt tgggtccaca acatcgaaaa  10560
gagactcctt gtgcaccatg taacacatca gggttcaatt atgtttctgt gcattgtcca  10620
gacgggatcc atgacgtctt tagttcacgg ggaccattgc ctgcttatct agggtctaaa  10680
acatctgaat ctacatctat tttgcagcct tgggaaaggg aaagcaaagt cccactgatt  10740
aaaagagcta cacgtcttag agatgctatc tcttggtttg ttgaacccga ctctaaacta  10800
gcaatgacta tactttctaa catccactct ttaacaggcg aagaatggac caaaaggcag  10860
catgggttca aaagaacagg gtctgccctt cataggtttt cgacatctcg gatgagccat  10920
ggtgggttcg catctcagag cactgcagca ttgaccaggt tgatggcaac tacagacacc  10980
atgagggatc tgggagatca gaatttcgac tttttattcc aagcaacgtt gctctatgct  11040
caaattacca ccactgttgc aagagacgga tggatcacca gttgtacaga tcattatcat  11100
attgcctgta agtcctgttt gagacccata aagagagatc ccctggactc aagtatggac  11160
tacacgcccc cagatgtatc ccatgtgctg aagacatgga ggaatgggga aggttcgtgg  11220
ggacaagaga taaaacagat ctatccttta gaagggaatt ggaagaattt agcacctgct  11280
gagcaatcct atcaagtcgg cagatgtata ggttttctat atggagactt ggcgtataga  11340
aaatctactc atgccgagga cagttctcta tttcctctat ctatacaagg tcgtattaga  11400
ggtcgaggtt tcttaaaagg gttgctagac ggattaatga gagcaagttg ctgccaagta  11460
atacaccgga gaagtctggc tcatttgaag aggccggcca acgcagtgta cggaggtttg  11520
```

-continued

```
atttacttga ttgataaatt gagtgtatca cctccattcc tttctcttac tagatcagga   11580
cctattagag acgaattaga aacgattccc cacaagatcc caacctccta tccgacaagc   11640
aaccgtgata tgggggtgat tgtcagaaat tacttcaaat accaatgccg tctaattgaa   11700
aagggaaaat acagatcaca ttattcacaa ttatggttat tctcagatgt cttatccata   11760
gacttcattg gaccattctc tatttccacc accctcttgc aaatcctata caagccattt   11820
ttatctggga aagataagaa tgagttgaga gagctggcaa atctttcttc attgctaaga   11880
tcaggagagg ggtgggaaga catacatgtg aaattcttca ccaaggacat attattgtgt   11940
ccagaggaaa tcagacatgc ttgcaagttc gggattgcta aggataataa taaagacatg   12000
agctatcccc cttggggaag ggaatccaga gggacaatta caacaatccc tgtttattat   12060
acgaccaccc cttacccaaa gatgctagag atgcctccaa gaatccaaaa tcccctgctg   12120
tccggaatca ggttgggcca attaccaact ggcgctcatt ataaaattcg gagtatatta   12180
catggaatgg gaatccatta cagggacttc ttgagttgtg gagacggctc cggagggatg   12240
actgctgcat tactacgaga aaatgtgcat agcagaggaa tattcaatag tctgttagaa   12300
ttatcagggt cagtcatgcg aggcgcctct cctgagcccc ccagtgccct agaaacttta   12360
ggaggagata aatcgagatg tgtaaatggt gaaacatgtt gggaatatcc atctgactta   12420
tgtgacccaa ggacttggga ctatttcctc cgactcaaag caggcttggg gcttcaaatt   12480
gatttaattg taatggatat ggaagttcgg gattcttcta ctagcctgaa aattgagacg   12540
aatgttagaa attatgtgca ccggattttg gatgagcaag gagttttaat ctacaagact   12600
tatggaacat atatttgtga gagcgaaaag aatgcagtaa caatccttgg tcccatgttc   12660
aagacggtcg acttagttca aacagaattt agtagttctc aaacgtctga agtatatatg   12720
gtatgtaaag gtttgaagaa attaatcgat gaacccaatc ccgattggtc ttccatcaat   12780
gaatcctgga aaaacctgta cgcattccag tcatcagaac aggaatttgc cagagcaaag   12840
aaggttagta catactttac cttgacaggt attccctccc aattcattcc tgatcctttt   12900
gtaaacattg agactatgct acaaatattc ggagtaccca cgggtgtgtc tcatgcggct   12960
gccttaaaat catctgatag acctgcagat ttattgacca ttagcctttt ttatatggcg   13020
attatatcgt attataacat caatcatatc agagtaggac cgatacctcc gaacccccca   13080
tcagatggaa ttgcacaaaa tgtggggatc gctataactg gtataagctt ttggctgagt   13140
ttgatggaga aagacattcc actatatcaa cagtgtttag cagttatcca gcaatcattc   13200
ccgattaggt gggaggctgt ttcagtaaaa ggaggataca agcagaagtg gagtactaga   13260
ggtgatgggc tcccaaaaga tacccgaatt tcagactcct tggccccaat cgggaactgg   13320
atcagatctc tggaattggt ccgaaaccaa gttcgtctaa atccattcaa tgagatcttg   13380
ttcaatcagc tatgtcgtac agtggataat catttgaaat ggtcaaattt gcgaagaaac   13440
acaggaatga ttgaatggat caatagacga atttcaaaag aagaccggtc tatactgatg   13500
ttgaagagtg acctacacga ggaaaactct tggagagatt aaaaaatcat gaggagactc   13560
caaactttaa gtatgaaaaa aactttgatc cttaagaccc tcttgtggtt tttattttt   13620 atctggtttt gtggtcttcg t                                            13641
```

<210> SEQ ID NO 17
<211> LENGTH: 9
<212> TYPE: PRT
<213> ORGANISM: Homo sapiens

<400> SEQUENCE: 17

-continued

```
Met Ser Phe Asp Pro Asn Leu Leu His
1               5

<210> SEQ ID NO 18
<211> LENGTH: 9
<212> TYPE: PRT
<213> ORGANISM: Homo sapiens
<220> FEATURE:
<221> NAME/KEY: VARIANT
<222> LOCATION: (1)..(9)
<223> OTHER INFORMATION: mutant

<400> SEQUENCE: 18

Met Ser Phe Asp Ser Asn Leu Leu His
1               5
```